(12) United States Patent
    Tabakoff

(10) Patent No.: US 10,435,371 B2
(45) Date of Patent: *Oct. 8, 2019

(54) MULTIFUNCTIONAL AMINOQUINOLINE THERAPEUTIC AGENT

(71) Applicant: LOHOCLA RESEARCH CORPORATION, Evanston, IL (US)

(72) Inventor: Boris Tabakoff, Elizabeth, IL (US)

(73) Assignee: LOHOCLA RESEARCH CORPORATION, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/130,789

(22) Filed: Sep. 13, 2018

(65) Prior Publication Data

US 2019/0092731 A1    Mar. 28, 2019

Related U.S. Application Data

(63) Continuation of application No. 15/318,964, filed as application No. PCT/US2015/036473 on Jun. 18, 2015, now Pat. No. 10,112,905.

(60) Provisional application No. 62/015,152, filed on Jun. 20, 2014.

(51) Int. Cl.
| | |
|---|---|
| *C07D 215/48* | (2006.01) |
| *A61K 31/4706* | (2006.01) |
| *A61K 45/06* | (2006.01) |
| *A61K 31/485* | (2006.01) |
| *A61K 31/616* | (2006.01) |
| *C07D 215/46* | (2006.01) |
| *A61K 33/24* | (2019.01) |

(52) U.S. Cl.
CPC ........ *C07D 215/48* (2013.01); *A61K 31/4706* (2013.01); *A61K 31/485* (2013.01); *A61K 31/616* (2013.01); *A61K 45/06* (2013.01); *C07D 215/46* (2013.01); *A61K 33/24* (2013.01)

(58) Field of Classification Search
CPC  C07D 215/48; C07D 215/46; A61K 31/4706; A61K 31/485; A61K 31/616; A61K 33/24; A61K 45/06
See application file for complete search history.

(56) References Cited

U.S. PATENT DOCUMENTS

| | | |
|---|---|---|
| 5,783,700 A | 7/1998 | Nichols et al. |
| 5,863,922 A | 1/1999 | Mayer et al. |
| 5,914,403 A | 6/1999 | Nichols et al. |
| 6,962,930 B1 | 11/2005 | Tabakoff |
| 7,923,458 B2 | 4/2011 | Tabakoff |
| 10,112,905 B2 * | 10/2018 | Tabakoff ............. C07D 215/46 |
| 2009/0023773 A1 | 1/2009 | Vohra et al. |

FOREIGN PATENT DOCUMENTS

| | | |
|---|---|---|
| WO | WO-98/55125 A1 | 12/1998 |
| WO | WO-2007/044682 A2 | 4/2007 |
| WO | WO-2007/044682 A3 | 4/2007 |
| WO | WO-2009/000085 A1 | 12/2008 |
| WO | WO-2012/048894 A1 | 4/2012 |

OTHER PUBLICATIONS

Offord, The Scientist Magazine, Jan. 2018, 1-9. (Year: 2018).*
Becker, H.C. (2008). "Alcohol Dependence, Withdrawl, and Relapse," *Alcohol Research & Health* 31(4):348-361.
Cruz, M.T. et al. (Jan. 14, 2011). "Type 7 Adenylyl Cyclase is Involved in the Ethanol and CRF Sensitivity of GABAergic Synapses in Mouse Central Amygdala," *Front Neurosci* 4:207.
Davies, M. (Jul. 2003). "The role of GABAA receptors in mediating the effects of alcohol in the central nervous system," *J Psychiatry Neurosci* 28(4):263-274.
Enoch, M.A. (Jul. 2008, e-published Mar. 15, 2008). "The role of GABA(A) receptors in the development of alcoholism," *Pharmacol Biochem Behav* 90(1):95-104.
Enoch, M.A. et al. (May 22, 2013). "A factor analysis of global GABAergic gene expression in human brain identifies specificity in response to chronic alcohol and cocaine exposure," *PLoS One* 8(5):e64014.
Hoffman, P.L. et al. (Jul. 1996). "Alcohol dependence: a commentary on mechanisms," *Alcohol & Alcoholism* 31(4):333-340.
International Search Report dated Sep. 16, 2015, for PCT Application No. PCT/US2015/036473, filed on Jun. 18, 2015, 3 pages.
Krystal, J.H. et al. (2002). Ethanol Abuse, Dependence, and Withdrawal: Neurobiology and Clinical Implications, Chapter 100 in *Neuropsychopharmacology:The Fifth Generation of Progress*, Davis et al. ed, pp. 1425-1443.
Kumar, S. et al. (Mar. 2004). "Ethanol regulation of gamma-aminobutyric acid A receptors: genomic and nongenomic mechanisms," *Pharmacol Ther* 101(3):211-226.
Le, A.D. et al. (Jan. 1986). "Tolerance to and cross-tolerance among ethanol, pentobarbital and chlordiazepoxide," *Pharmacol Biochem Behav* 24(1):93-98.
Linnoila, M. et al. (1990). "Benzodiazepines and Alcohol," *J Psychiar Res* 24(Suppl 2):121-127.

(Continued)

*Primary Examiner* — D Margaret M Seaman
(74) *Attorney, Agent, or Firm* — Edward D. Grieff; Mintz, Levin, Cohn, Ferris, Glovsky and Popeo, P.C.

(57) ABSTRACT

Aminoquinoline compounds useful for treating chronic pain, addiction, and other conditions are provided. The aminoquinoline compound is represented by Formula (I):

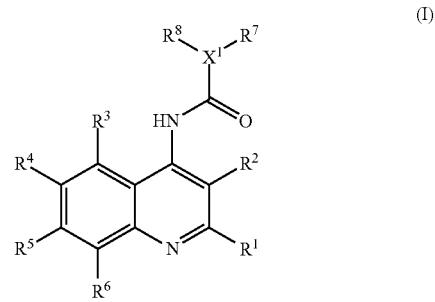

in which the substituents thereof are defined as set forth in the specification.

24 Claims, 20 Drawing Sheets

(56) References Cited

OTHER PUBLICATIONS

Mason, B.J. et al. (Jan. 2014). "Gabapentin treatment for alcohol dependence: a randomized clinical trial," *JAMA Intern Med* 174(1):70-77.

Snell, L.D. et al. (Jan. 2000). "Novel structure having antagonist actions at both the glycine site of the N-methyl-D-aspartate receptor and neuronal voltage-sensitive sodium channels: biochemical, electrophysiological, and behavioral characterization," *J Pharmacol Exp Ther* 292(1):215-227.

Spanagel, R. et al. (Mar.-Apr. 1999). "Long-term alcohol self-administration with repeated alcohol deprivation phases: an animal model of alcoholism?" *Alcohol & Alcoholism* 34(2):231-243.

Tabakoff, B. et al (Nov. 15, 2013, e-published Oct. 17, 2013). "The neurobiology of alcohol consumption and alcoholism: an integrative history," *Pharmacol Biochem Behav* 113:20-37.

Tabakoff, B. et al. (Aug. 5, 2016, e-published May 5, 2016). "A novel substituted aminoquinoline selectively targets voltage-sensitive sodium channel isoforms and NMDA receptor subtypes and alleviates chronic inflammatory and neuropathic pain," *Eur J Pharmacol* 784:1-14.

Voigt, R.M. et al. (Jan. 1, 2011, e-published Sep. 8, 2010). "Administration of GABA(B) receptor positive allosteric modulators inhibit the expression of previously established methamphetamine-induced conditioned place preference," *Behav Brain Res* 216(1):419-423.

Wang, Z.J. et al. (Nov. 2002). "Inhibition of neuronal Na+ channels by the novel antiepileptic compound DCUKA: identification of the diphenylureido moiety as an inactivation modifier," *Exp Neurol* 178(1):129-138.

Written Opinion dated Sep. 16, 2015, for PCT Application No. PCT/US2015/036473, filed on Jun. 18, 2015, 9 pages.

Adams et al, "CGP7930: A Positive Allosteric Modulator of the GABA-B Receptor," CNS Drug Reviews, 13(3):308-316 (2007).

Borghese et al, "GABA-A receptor transmembrane amino acids are critical for alcohol action: disulfide cross-linking and alkyl methanethiosulfonate labeling reveal relative location of binding sites," Journal of Neurochemistry, 128:363-375 (2014).

Borghese et al, "Novel Molecule Exhibiting Selective Affinity for GABA-A Receptor Subtypes," Nature (published on-line Jul. 24, 2017).

Campral® (acamprosate calcium) Package Insert, Forest Laboratories, Aug. 2005 (12 pages).

Chattopadhyay et al, "Vector-mediated release of GABA attenuates pain-related behaviors and reduces Na(V)1.7 in DRG neurons," European Journal of Pain, 15(9):913-920 (2011).

D'Hulst et al, "The complexity of the GABA-A receptor shapes unique pharmacological profiles," Drug Discovery Today, 14(17/18):866-875 (2009).

Grant et al, "Ethanol withdrawal seizures and the NMDA Receptor Complex," Eur. J. Pharmacol., 176:289-296 (1990).

Halbout et al, "The GABA-B positive modulator GS39783 decreases psychostimulant condition-reinforcement and conditioned-reward," Addiction Biology, 16:416-427 (2011).

Jembrek et al, "GABA Receptors: Pharmacological Potential and Pitfalls," Current Pharmaceutical Drugs, 21:4943-4959 (2015).

Kampman et al, "Initiating acamprosate within-detoxification versus post-detoxification in the treatment of alcohol dependence," Addict Behav, 34:6-7):581-586 (2009).

Margolis et al, "A novel opioid receptor-mediated enhancement of GABAA receptor function induced by stress in ventral tegmental area neurons," The Journal of Physiology, 589(Pt 17):4229-4242 (2011).

Muncie et al, "Outpatient management of alcohol withdrawal syndrome," Am Fam Physician, 88(9):589-595 (2013).

National Institute on Drug Abuse (NIDA), "Principles of drug addiction treatment: A research-based guide," Third Edition, National Institute on Drug Abuse; National Institutes of Health; US Department of Health and Human Services (2018) (67 pages).

Quednow et al, "Human pharmacology for addiction medicine: From evidence to clinical recommendations," Prog Brain Res, 224:227-250 (2016).

Saba et al, "A systems genetic analysis of alcohol drinking by mice, rats and men: influence of brain GABAergic transmission," Neuropharmacology, 60:1269-1280 (2010).

Tabakoff et al, "The neurochemistry of alcohol," Current Opinion in Psychiatry, 6:388-394 (1993).

Tabakoff et al, "Ethanol's action on the GABAA receptor: is there a requirement for parsimony?" Alcohol Clin Exp Res, 19:1597-1598 (1995).

Tabakoff et al, "Animal models in alcohol research," Alc Res & Health, 24:77-84 (2000).

Wallner et al, "Physiology and pharmacology of alcohol: the imidazobenzodiazepine alcohol antagonist site on subtypes of GABA-A receptors as an opportunity for drug development?" British Journal of Pharmacology, 154:288-298 (2008).

\* cited by examiner

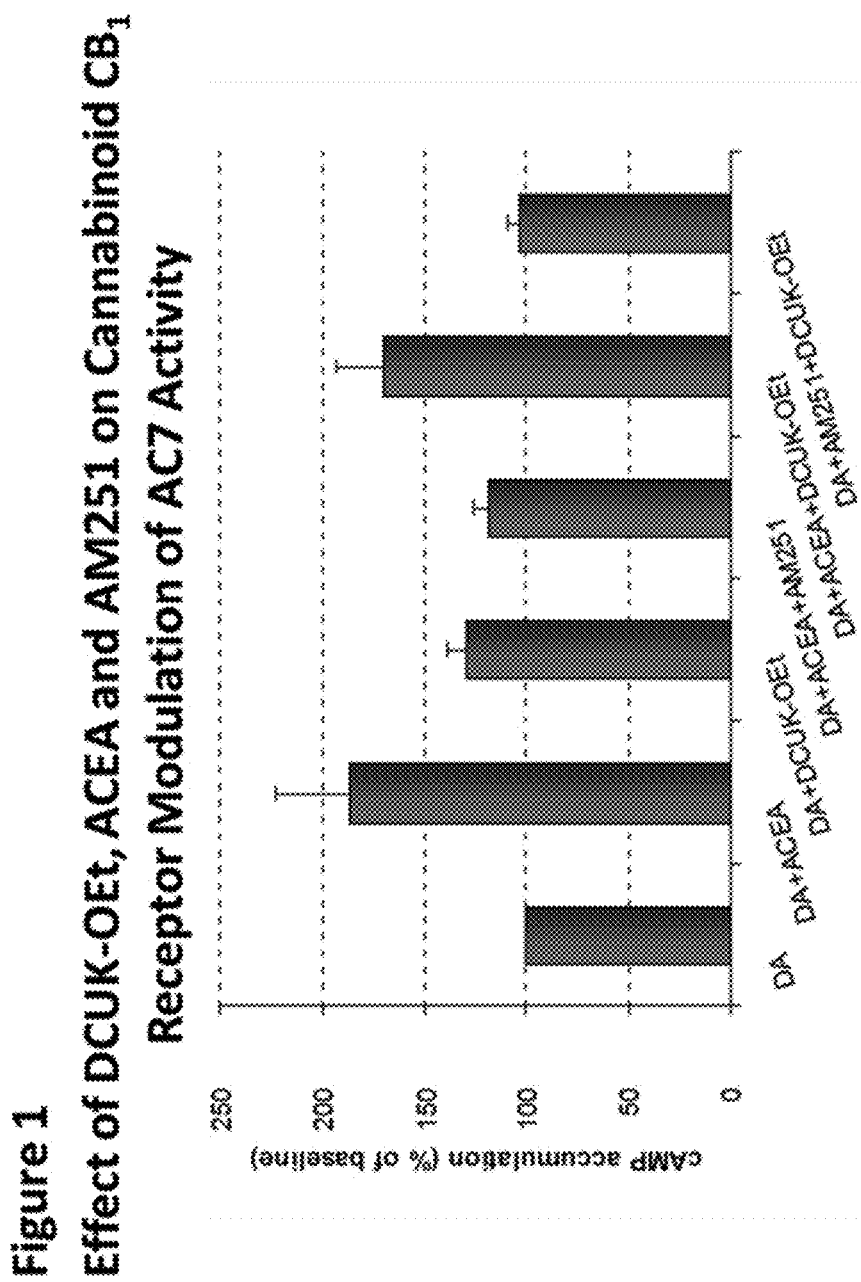

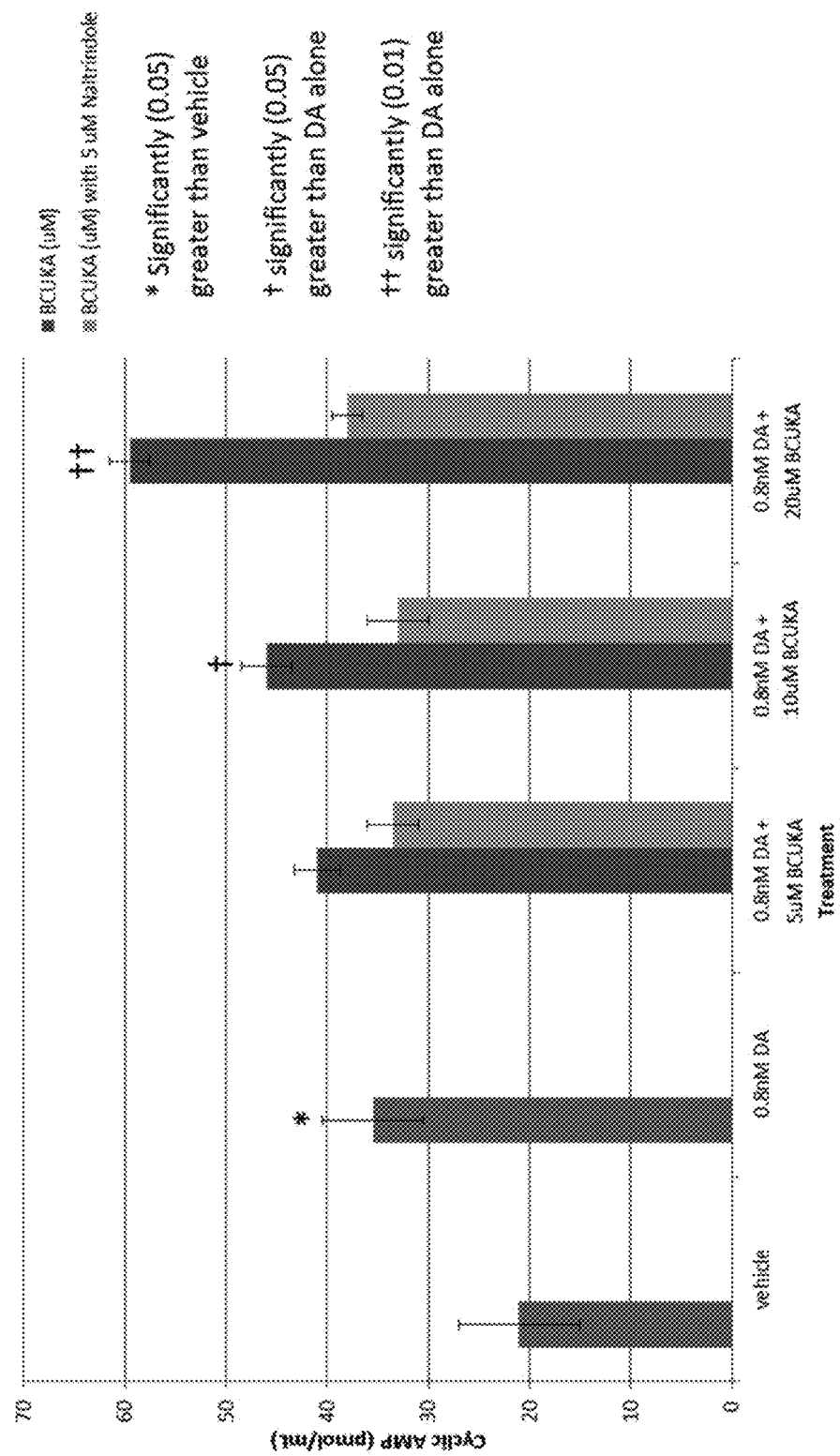

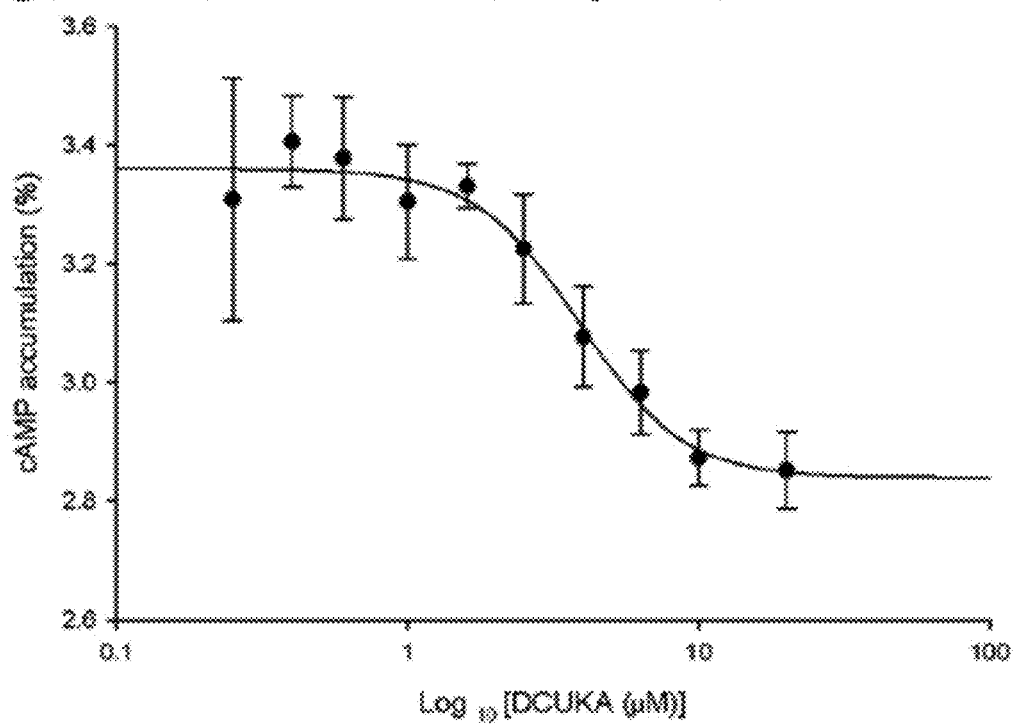
Figure 3. DCUKA concentration response curve

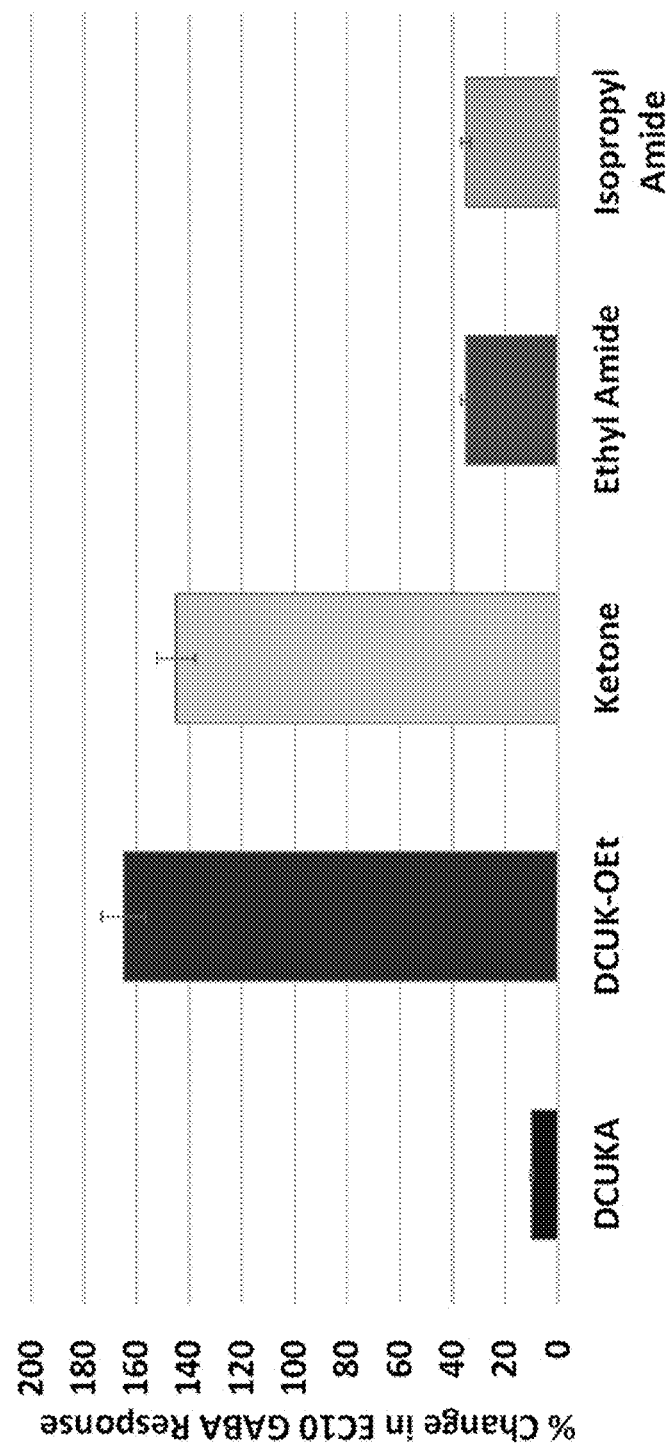

Figure 7. Effect of DCUKA on CFA-induced neuropathic pain

DCUKA (50 mg/kg) and BCUKA (50 mg/kg) reverse neuropathic pain in the CFA model

Naltrindole blocks DCUKA anti-allodynic effect in the CFA model

DCUKA prevention of the development of CFA induced inflammatory pain

DCUKA prevents the development of cisplatin-induced neuropathic pain

MULTIFUNCTIONAL AMINOQUINOLINE THERAPEUTIC AGENT

CROSS-REFERENCE TO RELATED APPLICATIONS

This application is a continuation of U.S. application Ser. No. 15/318,964 filed Dec. 14, 2016, issued as U.S. Pat. No. 10,112,905 which is a Section 371 US National Phase of PCT/US2015/036473 filed Jun. 18, 2015, which claims the benefit of US application Ser. No. 62/015,152 filed Jun. 20, 2014, the disclosures of which are incorporated by reference in their entirety.

GOVERNMENT SUPPORT

This invention was made with government support from the National Institutes of Health, Grant No. R44-AA-009930. The United States government has certain rights in this invention.

FIELD OF THE INVENTION

The present invention relates to aminoquinoline compounds and their use as therapeutic agents. In addition, the present invention relates to methods of treating and preventing chronic pain and treating addiction with certain aminoquinoline derivatives.

BACKGROUND OF THE INVENTION

Pharmaceutical science is undergoing changes in its perception of diagnostic criteria for categorization of disease and the value of medications that are engineered to simultaneously bind to and affect the function of more than one target. For a number of years, the pharmaceutical industry has diligently followed the paradigm of single target-based drug discovery, but the successes with this approach for generating novel medication have declined drastically, leading many to question this approach (Csermely et al., 2005; Sams-Dodd, 2005). More recently, there has been significant discussion that design of multi-target drugs (those in which a single molecule can effectively interact with more than one target in a disease-perturbed pathway) may be a more optimal approach to discovering new and more effective medications (Lu et al., 2012; Pang et al., 2012). In terms of categorization of various disease states it has become obvious that a number of diseases thought to be categorically different, may have etiologically similar pathways determining the pathology. This is particularly evident with neurodegenerative diseases where recent work indicates that cell-to-cell transmission of misfolded proteins may be the underlying cause of several, previously thought to be different, disease states (e.g., Parkinsonism, Alzheimer's disease, Huntington's Disease, etc.) (Guo and Lee, 2014).

In psychiatric disease areas such as schizophrenia and affective/cognitive disorders, similar neurotransmitter pathways consistently come to attention, as evidenced by the recent review on the glycine transporter (Harvey and Yee, 2013). In this review the authors also draw attention to the fact that the glycine receptor and transporter systems in the central nervous system (CNS) also are involved in alcohol dependence, pain and epilepsy. A more direct discussion of the similarities between alcohol dependence and chronic pain disorders can be found in a review authored by Egli, Koob and Edwards entitled "Alcohol Dependence as a Chronic Pain Disorder" (2012). The possible relationship between alcohol dependence and chronic pain syndromes is underscored by the current reports that drugs which have been used to treat chronic pain are now being found to be efficacious in preventing relapse in alcohol dependent subjects. A demonstration of this phenomenon is the use of gabapentin (which is a T-type calcium channel blocker) to treat chronic pain (Moore et al., 2014) and alcoholism (Mason et al., 2014).

Throughout the world millions of people suffer from chronic pain (e.g., 116 million in the U.S. alone (Institute of Medicine, 2011) and from alcohol abuse and dependence (e.g., 18 million in the U.S. (Grant et al., 2004)) or both, and similarities in the neurochemistry subsuming both chronic pain syndromes and alcohol dependence go well beyond the common involvement of T-type calcium channels. Three neurochemical systems have, in particular, been linked to both chronic pain and alcohol dependence. These systems are the GABA, cannabinoid and the opioid transmitter systems in brain and spinal cord (Zeilhofer et al., 2012). The GABA-A receptor system has been linked to both the acute and chronic actions of ethanol including the development of dependence and the generation of craving during periods of abstinence (Enoch et al., 2013; Kumar et al., 2004; Tabakoff and Hoffman, 2013). Chronic ethanol consumption by mice upregulates (increases expression of) delta opiate receptors in the CNS (van Rijn et al., 2012), and delta opiate receptor expression and function in certain areas of brain (e.g., ventral tegmental area) has been shown to modulate ethanol consumption by animals (Clapp et al., 2008). Some of the effects of agents which act as agonists at the delta opioid receptors have been proposed to be mediated via modulation of GABA neuron function (Kang-Park et al., 2007). The most informative recent description of how delta opiate receptors can modulate GABA-A receptor function is contained in (Margolis et al., 2011) and in that report, it is stressed that increases in delta receptor function "only appear following challenges such as inflammation, stress and administration of rewarding (addicting) drugs", and that such increases in function can change activity of other neurotransmitter systems (e.g., GABA).

The upregulation of delta opiate receptors is also a definitive aspect of the development of chronic pain (Cahill et al., 2003) and mice with genetic deletion of the delta opiate receptor are inherently more sensitive to painful stimuli (Gaveriaux-Ruff et al., 2011). Although it is rational to consider that delta opiate receptors are good targets for pharmaceuticals to treat chronic pain, there are currently no delta opiate receptor selective drugs approved by the Food and Drug Administration and some candidates have failed in Phase II clinical trials (van Rijn et al., 2013). A confound in the simplistic view that delta opiate receptors in and of themselves can reduce chronic pain, is that tolerance rapidly develops to the antihyperalgesic actions of delta opiate receptor agonists. Part of this "tolerance" mechanism is mediated via increased inhibition of GABA release in spinal cord and brain stem by upregulated delta opiate receptors which arise during development of chronic pain (Taylor, 2009; Zhang et al., 2006).

There also has been discussion in the literature that one should consider the possibility of preventing the development of chronic pain by medications administered in the early phase of the neuropathological process that produces chronic (neuropathic) pain syndromes (Kehlet et al., 2006; Van de Ven and John Hsia, 2012). One of the more accepted mechanisms for the progression of acute injury to chronic pain is an upregulation of voltage sensitive sodium channels (e.g., $Na_v1.7$ and $Na_v1.8$) in sensory neurons (Belkouch et al., 2014; Strickland et al., 2008). Studies performed with endogenous delta receptor agonists such as enkephalin have indicated that activation of delta opiate receptors can prevent the upregulation of $Na_v1.7$ in sensory neurons in rats treated to produce diabetic neuropathy (Chattopadhyay et al., 2008). Interestingly, the transfection of neurons with a vector, resulting in a constant release of GABA, also prevented the pathologic increase in $Na_v1.7$ resulting from chronic hyperglycemia (diabetes) (Chattopadhyay et al., 2011). Additionally, there is evidence that delta opiate receptors present in $Na_v1.8$-expressing nociceptive sensory neurons play a critical role in pain mechanisms (Gaveriaux-Ruff et al., 2011). Thus one can postulate that a novel medication that can activate both GABA receptors and delta opiate receptors may prevent the development of chronic (neuropathic) pain syndromes by interfering with the pathology induced upregulation of $Na_v1.7$ and 1.8 channels and/or other mechanisms. A medication that can simultaneously activate GABA receptors (Zeilhofer et al., 2012) and activate delta opiate receptors, as well as inhibiting the $Na_v$ 1.7 and 1.8 channels, can also be of benefit in reducing pain even after the development of a chronic pain syndrome.

The cannabinoid neurotransmitter system of the brain and spinal cord, in many ways resembles the opioid transmitter system. The endogenous agonists for cannabinoid and opiate receptors differ (i.e., anandamide is the agonist at the cannabinoid (CB1) receptors, while enkephalins are the agonists at the delta opiate receptors), but the receptor characteristics and physiologic function of the cannabinoid (CB1) receptor and the delta opiate receptor are quite similar. Both are G protein coupled receptors (GPCRs) that signal through the $G_i/G_o$ proteins and affect the function of the same set of neuronal enzymes and channels which carry out the CB1 and delta opioid receptor effects (Howlett et al., 2002). Both CB1 receptors and delta opiate receptors have been designated as targets for control of chronic pain syndromes (Normandin et al., 2013; Pernia-Andrade et al., 2009), and for reducing craving and high levels of alcohol consumption in alcohol dependent animals (Femenia et al., 2010; van Rijn et al., 2010). It is notable that pharmacological and direct interactions between delta opiate receptors have also been noted (Manzanares et al., 1999; Vigano et al., 2005). Particularly in the control of pain, delta 9-tetrahydrocannabinol (THC, a CB1 receptor agonist) has been shown to have synergistic effects with opiates, and these effects of THC have been stated to result from its actions at the delta opiate receptor, as well as CB1 receptors (Cichewicz, 2004). A more current theory of CB1 receptor and delta opiate receptor interactions is that there is a physical interaction (heterodimerization) between these receptors (Rios et al., 2006). Therefore, medications that affect the function of the CB1 cannabinoid receptor or the delta opiate receptor can modulate the activity of the interacting partner receptor system and have similar end effects on GABA release (Olive, 2010).

A joint, beneficial effect of multi-modal medications may as well be seen in preventing and treating relapse in alcoholics. By simultaneously enhancing GABA-A receptor function during a period of alcohol withdrawal in an alcohol dependent animal and modulating of cannabinoid or delta opiate receptors in a dependent subject (Bie et al., 2009a), control of craving and a reduction of relapse can be achieved.

The recent revision (the fifth) of the Diagnostic and Statistical Manual of the American Psychiatric Association (DSM V) defines alcoholism (Alcohol Use Disorder, AUD) by eleven criteria, of which two have to be met during the same 12 month period for an individual to be diagnosed as suffering from AUD (NIH Publication No. 13-7999, 2013). A novel addition to DSM V is a criterion of craving to the list of criteria that can define AUD. Craving was not a component of earlier DSM diagnostic criteria, but over recent years, the concept and phenomenon of craving has become a primary reason for individuals to relapse to alcohol use after a period of sobriety (Anton, 1999). Craving in the context of DSM V, is distinguished from attempts by an individual to control withdrawal signs which occur early (within a day or two) after an individual stops consuming ethanol, and alcohol or a closely related substance such as benzodiazepines may be taken to relieve withdrawal signs. The overt signs of alcohol withdrawal in humans last for five days to a week, and in terms of treatment, constitute the detoxification stage of treating alcoholism. The manifestations of craving as defined by DSM V and in other publications (Kavanagh et al., 2013) are cognitive-emotional events over a period of years rather than days, and are manifestations of limbic system function (Heinz et al., 2009). The early withdrawal signs are a neural hyperactivity syndrome exhibited over most of the brain with particular involvement of the cerebral cortex (Coutin-Churchman et al., 2006). One of the most significant distinctions between the biologic characteristics of the withdrawal syndrome and the later manifestations of craving is in terms of pharmacologic treatments. For instance, benzodiazepines are commonly used to advantage in treating the acute stages of the alcohol withdrawal syndrome, but are contraindicated for more prolonged use in allay craving (Licata and Rowlett, 2008). On the other hand, the drugs most currently used in the U.S.A. for treating craving and preventing relapse, i.e., acamprosate and naltrexone, are significantly more effective if given after detoxification or after a prescribed period (weeks) of abstinence.

There is an ongoing need for medications that can treat chronic pain, addiction, addiction relapse, and the like. Methods of synthesis of substituted quinolone ureas are disclosed herein, which significantly expands on the series of chemical entities which have substitutions on the terminal nitrogen of 4-ureido-5,7-dihalo-2-carboxy-quinolines and in which the 2-position is a carboxy group, an ester, a ketone, an ether or an amide. Certain of the compounds synthesized by the methods described herein unexpectedly have affinity for and pharmacological actions at the mammalian GABA-A receptor, the cannabinoid (CB1) receptor, the voltage sensitive sodium channels ($Na_v$ 1.7 and 1.8) and/or the delta opiate receptor while having little or no affinity for a large number of other receptors/channels/enzymes.

GABA-A receptors are agonist gated ion channels which respond to the presence of the neurotransmitter GABA by increasing permeability to chloride ions and thus generating hyperpolarization and inhibition of ongoing activity in neurons. The GABA-A receptors are composed of five distinct protein subunits with the majority of the GABA-A receptors in brain having a composition consisting of two alpha (α) subunits, two beta (β) subunits and one gamma (γ), delta (δ), theta (θ) or pi (π) subunit. Currently 19 GABA-A receptor subunits are known (α 1-6, β 1-3, γ 1-3, δ, ε, θ, π and 3 rho (ρ) subunits).

GABA-A receptors are the site of action of a number of clinically important drugs such as benzodiazepines, barbiturates, anesthetics, analeptics, neuroactive steroids, etc. and all of these drugs interact with binding sites that are partially or completely distinct from one another. These binding sites, including the binding sites for GABA itself, are generated by the interactions of various subunits and are formed at the interface of the various subunits that come together to produce the pentameric combination that characterizes the native GABA-A receptors in brain and spinal cord. Given the large number of subunit combinations that are possible (although not all have been demonstrated) it is not surprising that the GABA-A receptor demonstrates a complex pharmacologic profile.

A large number of molecules have been synthesized and shown to interact with GABA-A receptors of a particular subunit combination, and these molecules display a variety of pharmacologic characteristics including sedation, anesthesia, anxiolysis, anticonvulsant effects, muscle relaxation, analgesia, antipsychotic actions and even modulation of immune system function depending on the subunits present in particular GABA-A receptors and the way in which the subunits interact.

The most common type of GABA-A receptor present in brain consists of two $\alpha_1$ subunits, two $\beta_2$ subunits and a $\gamma_2$ subunit and these receptors are mostly located within the membrane of the post-synaptic neuron at the synapse. These and other synaptically located GABA-A receptors are mediators of phasic GABA signals in response to GABA release from the pre-synaptic terminal. On the other hand, GABA-A receptors that contain a $\delta$ subunit instead of a $\gamma$ subunit are located extra-synaptically (outside of the synapse) and generate a tonic inhibition of the post-synaptic neuron in response to GABA that "leaks" out of the synaptic cleft. These extra-synaptic GABA-A receptors, not only are distinguished by their $\delta$ subunit but also by $\alpha$ subunits. The extra-synaptic GABA-A receptors can contain only $\alpha_1$, $\alpha_4$ or $\alpha_6$ subunits in association with the $\delta$ subunit.

The $\alpha_1$ subunit in association with the $\delta$ subunit is primarily found in the interneurons and pyramidal cells of the hippocampus, the $\alpha_4$ together with $\delta$ is expressed in the thalamic relay neurons and dentate gyrus granule cells and the $\alpha_6$ and $\delta$ subunit containing GABA-A receptors are primarily localized to the cerebellar granule cells. The different anatomical distribution of particular $\alpha$ subunits in conjunction with the $\delta$ subunit bespeaks different function and further physiologic differences exist between the different $\alpha$ and $\delta$ subunit combinations. For instance, the extra-synaptic GABA-A receptors composed of the $\alpha_1$ $\beta_2$ or $\beta_3$, and $\delta$ subunits have very low permeability for chloride ions even in the presence of high concentrations of GABA. On the other hand, these "silent" receptors are quite active when GABA is applied together with a positive allosteric modulator which is effective at $\delta$ subunit containing GABA-A receptors. It is therefore clear that discovery of molecular entities that have selectivity for particular subunit combinations within the GABA-A receptor can generate novel medications either with predicted or unanticipated spectra of physiologic or anti-pathologic effects.

Given the above described literature on the involvement of GABA-A, CB1 and delta opiate receptors in relapse drinking in alcohol dependent subjects and in the etiology of chronic pain syndromes, a series of the compounds described herein were tested in animal models of relapse drinking and chronic pain syndromes. A pattern of effects was observed that can predict that particular N-substituted-4-ureido-5,7-dichloro-2-carboxy (or carboxyester)-quinolines can be effective in preventing relapse in addicted humans and also can be effective in treatment and prevention of chronic neuropathic pain in humans.

SUMMARY OF THE INVENTION

The present invention provides multifunctional aminoquinoline compounds that are useful for treatment of one or more conditions such as alcohol or drug dependence, addiction relapse, chronic pain, and other conditions that can benefit from activation of GABA-A, CB1, and delta opiate receptors and inhibition of voltage sensitive sodium channels ($Na_v$, 1.7 and 1.8).

In a first embodiment, aminoquinoline compound is represented by Formula (I):

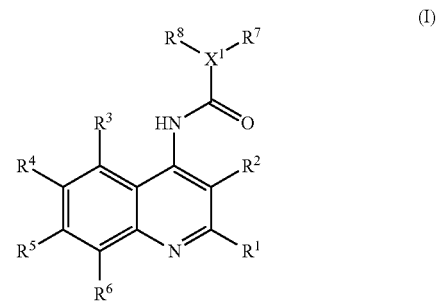

in which the substituents thereof are defined as follows: $R^1$ is H, $C_2$-$C_4$ alkyl, $C_2$-$C_4$ alkenyl, halo, $Z^1R^9$, or $N(R^{10})(R^{11})$. $R^2$ is H, $C_1$-$C_4$ alkyl, $C_2$-$C_4$ alkenyl, halo, $Z^2R^{12}$, $N(R^{13})(R^{14})$, or $C_1$-$C_4$ alkyl substituted with one or more moiety selected from the group consisting of $C_1$-$C_4$ alkyl, $C_2$-$C_4$ alkenyl, halo, $Z^3R^{15}$, $N(R^{16})(R^{17})$; each $R^3$, $R^4$, $R^5$, and $R^6$ independently is H, $C_1$-$C_4$ alkyl, $C_2$-$C_4$ alkenyl, halo, $Z^3R^{18}$, or $N(R^{19})(R^{20})$; $X^1$ is N or CH; each $R^7$ and $R^8$ independently is H, $C_1$-$C_6$ alkyl, $C_2$-$C_4$ alkenyl, $C_2$-$C_4$ alkynyl, aryl, or $C_1$-$C_6$ alkyl substituted with one or more moiety selected from the group consisting of $C_1$-$C_4$ alkyl, $C_2$-$C_4$ alkenyl, nitro, halo, $Z^4R^{21}$, and $N(R^{22})(R^{23})$; or $R^7$ and $R^8$ together with $X^1$ form a 5 to 8 member saturated, unsaturated, or aromatic organic cyclic or heterocyclic moiety; each $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, and $R^{23}$ independently is H, $C_1$-$C_4$ alkyl, or $C_1$-$C_4$ alkyl substituted with one or more moiety selected from the group consisting of $C_1$-$C_4$ alkyl, $C_2$-$C_4$ alkenyl, $C_2$-$C_4$ alkynyl, halo, heteroaryl, $Z^5R^{24}$, and $N(R^{25})(R^{26})$. Each of $Z^1$, $Z^2$, $Z^3$, $Z^4$, and $Z^5$ independently is O, S, NH, C(=O)O, O—C (=O), C(=O), or C(=O)NH. Each $R^{24}$, $R^{25}$, and $R^{26}$ independently is $C_1$-$C_4$ alkyl with the proviso that when $R^1$ is $Z^1R^9$, $Z^1$ is C(=O)O, $R^9$ is H or $C_1$-$C_2$ alkyl, each of $R^3$ and $R^5$ is halo, $X^1$ is N, and each of $R^4$ and $R^6$ is H, then at least one of $R^7$ and $R^8$ is not a phenyl, alkoxy-substituted phenyl, or $C_1$-$C_6$ alkyl group.

In a second embodiment, the aminoquinoline compound is a compound of Formula (II):

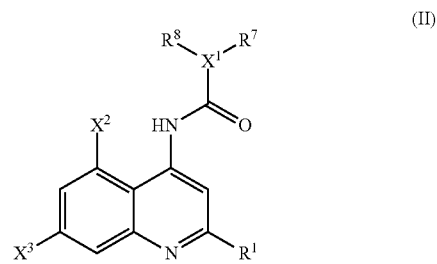

wherein $X^1$, $R^1$, $R^7$ and $R^8$ are as defined in Formula (I) above, and each $X^2$ and $X^3$ independently is an electron withdrawing group such as halo, nitro, and the like, with the proviso that when $R^1$ is $Z^1R^9$, $Z^1$ is C(=O)O or C(=O), $R^9$ is H or $C_1$-$C_4$ alkyl, and $X^1$ is N, then at least one of $R^7$ and $R^8$ is not a phenyl or alkoxy-substituted group.

In a third embodiment, the aminoquinoline compound is an aminodihaloquinoline compound of Formula (III):

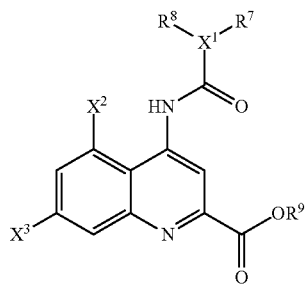

(III)

wherein $X^2$ and $X^3$ each independently is halo, and each of $X^1$, $R^1$, $R^7$, $R^8$ and $R^9$ are as defined in Formulas (I) and (II) described above, with the proviso that when $R^9$ is H or $C_1$-$C_2$ alkyl, and $X^1$ is N, then at least one of $R^7$ and $R^8$ is not a phenyl or alkoxy-substituted phenyl group.

In a fourth embodiment, the aminoquinoline compound is a compound of Formula (IV):

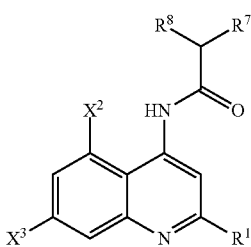

(IV)

wherein each of $X^2$, $X^3$, $R^1$, $R^7$, and $R^8$ are as defined in Formulas (I) and (II) above.

In a fifth embodiment, the aminoquinoline compound is an aminodihaloquinoline compound of Formula (V):

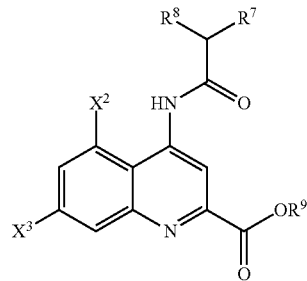

(V)

wherein each of $X^2$, $X^3$, $R^7$, $R^8$ and $R^9$ are as defined in Formulas (I) and (II) above.

In a sixth embodiment, the aminoquinoline compound is represented by Formula (VI):

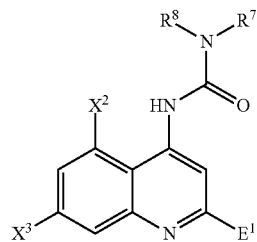

(VI)

wherein $R^7$ is alkyl (preferably a 3 to 6 carbon alkyl), cycloalkyl (preferably a 3 to 6 carbon cycloalkyl), aminoalkyl or phenyl; $R^8$ is H, alkyl (preferably a 3 to 6 carbon alkyl), cycloalkyl (preferably a 3 to 6 carbon cycloalkyl), aminoalkyl, or phenyl; $E^1$ is —C(═O)$OR^9$, —C(═O)$R^9$, —C(═O)N($R^9$)$_2$, and —[C($R^9$)$_2$]$_n$—$OR^9$; "n" is 1, 2, 3, or 4; each $R^9$ independently is H, $C_1$-$C_4$ alkyl, or $C_1$-$C_4$ alkyl substituted with one or more moiety selected from the group consisting of $C_1$-$C_4$ alkyl, $C_2$-$C_4$ alkenyl, $C_2$-$C_4$ alkynyl, halo, heteroaryl, $Z^5R^{24}$, and N($R^{25}$)($R^{26}$); $Z^5$ is O, S, C(═O)O or O—C(═O); each $R^{24}$, $R^{25}$, and $R^{26}$ independently is $C_1$-$C_4$ alkyl the alkyl; each $X^2$ and $X^3$ independently is an electron withdrawing group (preferably halogen or nitro); the alkyl, cycloalkyl, amino alkyl, and phenyl groups can be unsubstituted or substituted one or more times with an alkyl (1-3 carbons) group or an alkyloxy group (e.g., a 1 to 3 carbon alkyl or alkoxy group); and when acidic or basic functional groups are present, the compound can be in the free acid form, free base form, or can be a pharmacologically acceptable addition salt. When $E^1$ is C(═O)$OR^9$, at least one of $R^7$ and $R^8$ is not phenyl. Preferably $R^9$ is H or 1 to 3 carbon alkyl. In some preferred embodiments of the compounds of Formula (VI), $E^1$ is C(═O)$OR^9$ and $R^9$ preferably is H or 1 to 4 carbon alkyl or cycloalkyl.

Administration of the compounds of Formula (VI) can be by oral, subcutaneous, intravenous, intramuscular, intraperitoneal, transdermal or buccal routes for therapeutic treatment.

Non-limiting examples of compounds of the general Formula (VI) are derivatives of the 2-carboxy-quinolines, e.g., (N, N-dibutyl)-4-ureido-5,7-dichloro-2-carboxy-quinoline (BCUKA) N,N-diphenyl-4-ureido-5,7-dichloro-2-butanone, quinoline and the like. These compounds demonstrate affinity for the GABA-A receptor, the CB1 cannabinoid receptor and the delta opiate receptor.

The di-substituted-4-ureido-5,7-dichloro-2-carboxy-quinoline and 2-butanone-quinoline compounds of Formula (VI) and their methyl and ethyl esters possess affinity for GABA-A, cannabinoid CB1, and delta opiate receptors. These compounds can also act as positive allosteric modifiers of GABA action at the GABA-A receptor and as partial agonists at the cannabinoid CB1 receptors. These compounds possess beneficial activity in treating chronic pain syndromes arising from inflammatory and mechanical damage to peripheral nerves with particular compounds being more effective in ameliorating mechanical allodynia/hyperalgesia, while other derivatives more effectively ameliorate thermal hyperalgesia. Additionally, these compounds have dose related activity in reducing or completely blocking abstinence-induced craving and reducing escalated ethanol consumption by animals which are made dependent on ethanol.

In some embodiments, the aminoquinoline compound of Formula (I), (II), (III), (IV) (V), or (VI) is administered to the subject in conjunction with an additional therapeutic agent different from the aminoquinoline compound, e.g. opiates, opiate agonists, or opiate antagonists.

In another aspect, the present invention provides a method for the treatment of chronic pain (e.g., chronic neuropathic pain, such as peripheral neuropathic pain). The method comprises administering an aminoquinoline compound to a subject suffering from chronic pain, wherein the aminoquinoline compound is a compound of Formula (I), (II), (III) (IV), (V) or (VI) as defined above, with the proviso for compounds of Formula (I), (II) and (III) that when $R^1$ is $Z^1R^9$, $Z^1$ is C(=O)O, $R^9$ is H or $C_1$-$C_2$ alkyl, each of $R^3$, $R^5$, $X^2$, and $X^3$ is halogen, $X^1$ is N, and each of $R^4$ and $R^6$ is H, then at least one of $R^7$ and $R^8$ is not a phenyl or alkoxy-substituted phenyl group.

In another aspect, the present invention also provides pharmaceutical compositions, e.g., for treating chronic pain and of addiction relapse, comprising an aminoquinoline compound of Formula (I), (II), (III) (IV), (V), or (VI) as defined herein in combination with a pharmaceutically acceptable carrier. In the case of pharmaceutical compositions for treating chronic pain (e.g., neuropathic pain) with the compounds of Formula (I), (II) or (III), when $R^1$ is $Z^1R^9$, $Z^1$ is C(=O)O, $R^9$ is H or $C_1$-$C_2$ alkyl, each of $R^3$, $R^5$, $X^2$, and $X^3$ is halogen, $X^1$ is N, and each of $R^4$ and $R^6$ is H, then at least one of $R^7$ and $R^8$ is not a phenyl or alkoxy-substituted phenyl group.

In another aspect a method of preparing a compound of Formula (VI) is provided, which comprises amidation of a 5,7-dichloroquinolone-2-carboxylate intermediate (e.g., obtainable by Michael addition of 3,5-dichloroaniline to dimethyl acetylene dicarboxylate, followed by thermal cyclization of the resultant aryl maleate) with chlorosulfonyl isocyanate to generate (4-amino)-5,7-dichloro-2-carboxyquinoline ethyl ester (a key intermediate), which can be functionalized through reactions with relevant electrophiles. For preparation of monosubstituted ureas, a reactive urea intermediate is prepared through the reaction of a primary amine with carbonyldiimidazole. Reacting the resulting imidazoleurea with the amino-5,7-dichloro-2-carboxy-quinoline ethyl ester in the presence of sodium hydroxide yields a target mono-substituted urea at the 4 position of the quinoline, with concomitant ester hydrolysis. Removal of a protecting group, such as a tert-butoxycarbonyl (BOC)-protecting group, if such is used in the synthesis of the reactive urea intermediate, can be achieved with trifluoroacetic acid (TFA), to produce a desired TFA salt.

For preparation of disubstituted urea derivatives, the (4-amino)-5,7-dichloro-2-carboxy-quinoline methyl or ethyl ester is acetylated at the 4-amino position with a disubstituted carbamoyl chloride to form a (N, N-disubstituted)-4-ureido-5,7-dichloro-2-carboxy-quinoline ester. Optionally, the (N, N-disubstituted)-4-ureido-5,7-dichloro-2-carboxy-quinoline-ester can be hydrolyzed to an (N, N-disubstituted)-4-ureido-5,7-dichloro-2-carboxy-quinoline.

For the preparation of compounds in which $R^1$ is an amide (i.e., C(=O)NHR$^9$), the corresponding carboxylic acid (i.e., where $R^1$ is C(=O)OH) can be amidated by any convenient amidation reaction, e.g., by conversion of the carboxylic acid to an activated carbonyl (e.g., an acid chloride or through the use of a coupling agent such as N,N-dicyclohexylcarbodimide, DCC) and subsequent reaction with an amine.

For the preparation of compounds in which $R^1$ is a ketone (i.e., C(=O)R$^9$), the corresponding carboxylic acid (i.e., where $R^1$ is C(=O)OH) can be amidated with N,O-dimethylhydroxylamine by any convenient amidation reaction, as described above, and subsequent reaction of the resulting N-methoxyamide a Grignard reagent to form the ketone.

In another aspect, a method of allosterically modulating the activity of GABA-A receptors is provided, which comprises contacting the receptor with a compound having the formula: (N,N-dibutyl)-4-ureido-5,7-dichloro-2 carboxy quinoline (BCUKA), N,N-diphenyl-4-ureido-5,7-dichloro-2-butanone quinoline (DCVK-butanone), and the like.

In another aspect, a method of directly activating the delta opiate receptor is provided, which comprises contacting the receptor with DCUKA and/or BCUKA.

In another aspect, a method of directly activating the cannabinoid (CB1) receptor is provided, which comprises contacting the receptor with DCUK-OEt.

In another aspect, a method for treating a drug and/or alcohol-dependent individual to prevent relapse is provided, which comprises administering to a patient in need of such treatment an effective amount of DCUK-OEt, DCUKA, DCUK-butanone (3-(2-Butyryl-5,7-dichloroquinolin-4-yl)-1,1-diphenylurea) or a DCUK-amide (e.g., 5,7-dichloro-4-(3,3-diphenylureido)-N-ethylquinoline-2-carboxamide, or 5,7-dichloro-4-(3,3-diphenylureido)-N-isopropylquinoline-2-carboxamide).

In another aspect, a method for treating a patient suffering from chronic pain (neuropathic pain) and ameliorating such pain is provided, which comprises administering an effective amount of DCUKA, BCUKA and/or DCUK-OEt.

In another aspect, a method of preventing the development of chronic (neuropathic) pain after an individual sustains an injury or suffers from chemically or pathologically-induced nerve damage is provided, which comprises administering an effective amount of DCUKA and/or BCUKA to the individual prior to the time that chronic (neuropathic) pain is evident.

In another aspect, a method for potentiating the effects of other analgesic compounds, such as aspirin and opiates (e.g., morphine), in patients suffering from chronic pain is provided, which comprises administering, together with sub-therapeutic doses of aspirin or opiate, an effective amount of DCUKA and/or DCUK-OEt.

Advantageously, DCUKA, BCUKA and DCUK-OEt each exhibit affinity (Ki<10 µM) for at least two of the following receptors: the GABA-A receptor, the delta opiate receptor, the cannabinoid (CB1) receptor, and the voltage sensitive sodium channels ($Na_v$ 1.7 and 1.8).

BRIEF DESCRIPTION OF THE DRAWINGS

FIG. 1 illustrates the agonist properties of DCUK-OEt in cells transfected with the cannabinoid CB1 receptor. These cells also express dopamine (D1) receptors and Type 7 adenylyl cyclase; both the combination of dopamine (DA) and ACEA, and the combination of DA/ACEA/DCUK-OEt, provided statistically significant (p<0.05) increases in cAMP accumulation compared to DA alone.

FIG. 2 illustrates the agonist properties of BCUKA in cells transfected with delta opiate receptors. These cells also express dopamine (D1) receptors and Type 7 adenylyl cyclase.

FIG. 3 illustrates the agonist properties of DCUKA in cells transfected with delta opiate receptors. These cells also express dopamine (D1) receptors and Type 5 adenylyl cyclase. HeLa cells were transfected with the dopamine D1 receptor, DOR and AC5 isoform. The assay included 10 µM DA, and DCUKA concentrations ranging from 0.25-20 µM.

FIG. 4C illustrates the structure/activity relationship on the efficacy of five DCUK derivatives. This data indicates that DCUK-OEt and DCUK-butanone were most efficacious and suggests that an ester or amide substituent at the 2-position of DCUK is important for the positive allosteric properties of the DCUK compounds.

FIG. 4D provides a graphic representation of a rank ordering of the effects of DCUK-OEt on GABA-A receptors having different subunit compositions, beginning with the most responsive receptor.

DETAILED DESCRIPTION OF PREFERRED EMBODIMENTS

Figure 4A:
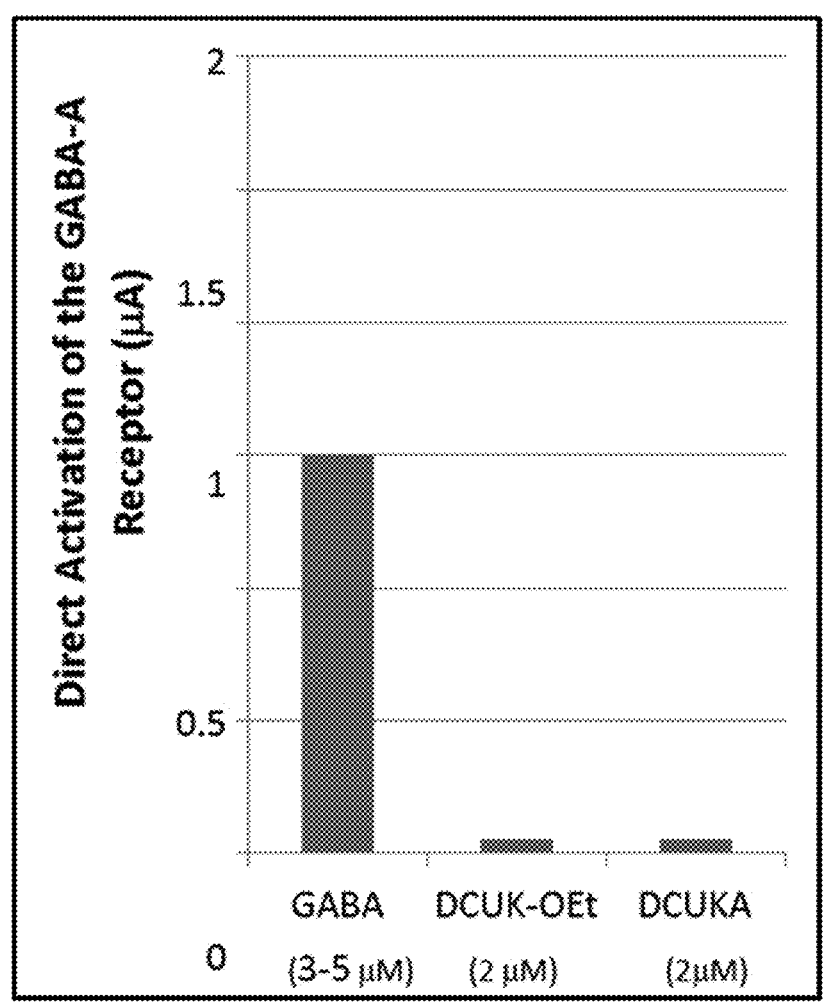
FIG. 4A compares the effects of DCUKA and DCUK-OEt alone or in the presence of GABA on chloride currents generated by activation of GABA-A receptors. DCUKA and DCUK-OEt had no effect on chloride currents by themselves, but significantly enhanced GABA-induced currents. The results indicate that DCUKA and DCUK-OEt are allosteric modulators of the actions of GABA.

The present invention provides multifunctional aminoquinoline compounds that activate the delta opioid receptor, cannabinoid CB1 receptor, and GABA-A (i.e., act as a positive allosteric modulator, PAM, and inhibit voltage sensitive sodium channels $Na_v$ 1.7 and 1.8). Compounds having such properties provide significant opportunities for treatment of chronic (neuropathic) pain syndrome and prevention of relapse in patients recovering from alcohol and/or drug addiction.

Some methods described herein comprise treating a subject (e.g., a human or animal patient) with the aminoquinoline compound (e.g., in a pharmaceutical composition as described herein). The compound is administered to the patient at a dosage and in a dosage form suitable for the intended use and administration, as described herein. The aminoquinoline compounds and pharmaceutical compositions comprising the compounds can be administered as a stand-alone treatment or, optionally, the compounds and compositions can be administered in conjunction with (i.e., in combination with or concurrently with) additional therapeutic agents. For example, in the case of treating chronic pain, the aminoquinoline compounds and compositions comprising the compounds can be administered in conjunction with an analgesic or anti-inflammatory agent which is different from the aminoquinoline compound, e.g., an opiate, an opioid agonist, or antagonist, a non-steroidal anti-inflammatory drug (NSAID), a corticosteroid, a serotonin reuptake inhibitor (SSRI), a calcium channel blocker (CCB), an anticonvulsant, a therapeutic agent for treating a disease (e.g., a disease associated with chronic pain, such as arthritis), and the like. Some specific combinations include, for example combinations of a compound of Formula (I), (II), (III), (IV), (V) and/or (VI) with an NSAID such as aspirin, ibuprofen, or naproxen; with an SSRI such as duloxetine (e.g., CYMBALTA® brand SSRI) or fluoxetine (PROZAC® brand SSRI); with a CCB such as gabapentin or clonidine; or with an opiate or opioid such as morphine or oxycodone; or with an anticonvulsant such as pregabalin (e.g., LYRICA® brand anticonvulsant). In the case of preventing relapse in alcohol addicted individuals, the aminoquinoline compounds and compositions containing same can be used with other active agents used for the treatment of alcoholism such as opiate antagonists, anticonvulsants, antidepressants, chronic pain medications, and the like.

The aminoquinoline compounds of Formula (I), (II), (III), (IV), (V) and (VI) can be prepared by any convenient method known to those skilled in the art. For example, U.S. Pat. No. 6,962,930 to Tabakoff et al. and U.S. Pat. No. 7,923,458 to Tabakoff, which are incorporated herein by reference in their entirety, describe the preparation of certain quinoline compounds analogous to those of the present invention, which readily can be adapted to the preparation of the aminoquinoline compounds of Formula (I), (II), (III), (IV) and (V). Scheme 1 provides a general scheme for preparing aminoquinoline compounds of Formula (I) and structurally related or analogous compounds from a 4-amino-substituted quinoline Compound (A), in which the R substituents are the same as those in Formula (I). The amino group of Compound (A) is reacted with an activated acylating Compound (B), comprising a leaving group (LG) that is reactive toward aromatic amino groups, to form a compound of Formula (I). Substituted quinoline compounds having an amino group in the 4-position of the quinoline ring structure, such as Compound (A), having various substitution patterns on the quinoline ring system, and the preparation thereof, are well known to those of ordinary skill in the chemical arts. Protective groups, such as those disclosed in *Protective Groups in Organic Synthesis,* 3rd Ed., Green and Wuts, Eds., John Wiley & Sons, Inc. (1999), which is incorporated herein by reference, can be utilized in the preparation of Compound (A), Compound (B) and/or in the coupling of Compound (A) and Compound (B), as needed or desired to facilitate the preparation and/or isolation of the compounds of Formula (I).

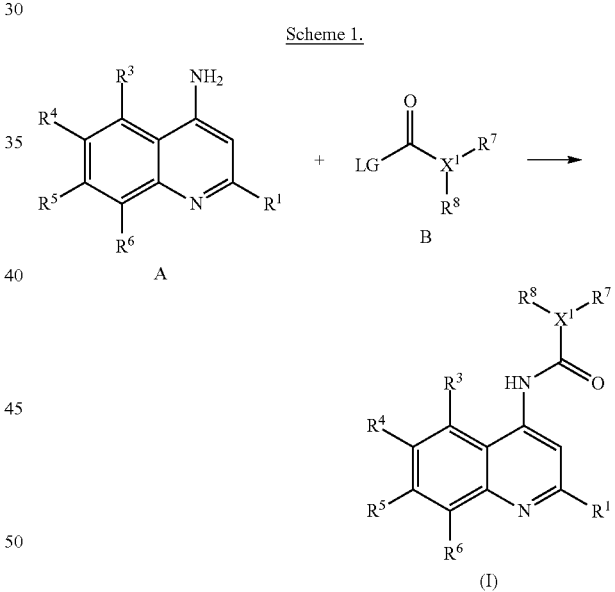

Scheme 1.

As used herein, the term "aminoquinoline compound" refers to compounds as set forth in Formulas (I), (II), (III), (IV), (V) and (VI) as described herein. The aminoquinoline compounds are useful for chronic pain and a variety of other conditions.

The term "alkyl" as used herein is directed to a saturated hydrocarbon group (designated by the formula $C_nH_{2n+1}$) which is straight-chained, branched or cyclized ("cycloalkyl") and which is unsubstituted or substituted, i.e., has had one or more of its hydrogens replaced by another atom or molecule.

"Aryl" designates either the 6-carbon benzene ring or the condensed 6-carbon rings of other aromatic derivatives (see, e.g., *Hawley's Condensed Chemical Dictionary* (13 ed.), R.

J. Lewis, ed., J. Wiley & Sons, Inc., New York (1997)). Aryl groups include, without limitation, phenyl and naphthyl.

"Heteroaryl" rings are aromatic rings including at least one carbon atom in the ring and one or more, typically from 1-4, atoms forming the ring is an atom other than a carbon atom, i.e., a heteroatom (typically O, N or S). Heteroaryl includes, without limitation: morpholinyl, piperazinyl, piperidinyl, pyridyl, pyrrolidinyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, indolinyl, indolyl-4,7-dione, 1,2-dialkyl-indolyl, 1,2-dimethyl-indolyl, and 1,2-dialkyl-indolyl-4,7-dione.

"Alkoxy" means —OR where R is alkyl as defined above, e.g., methoxy, ethoxy, propoxy, 2-propoxy and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched divalent hydrocarbon radical of three to six carbon atoms, containing at least one triple bond, e.g., ethynyl, propynyl, and the like.

"Halide" and "halo" refer to a halogen atom including fluorine, chlorine, bromine, and iodine.

Substituent groupings, e.g., $C_{1-6}$ alkyl, are known, and are hereby stated, to include each of their individual substituent members, e.g., $C_1$ alkyl, $C_2$ alkyl, $C_3$ alkyl and $C_4$ alkyl.

"Substituted" means that one or more hydrogen atoms on the designated atom is/are replaced with a selection from the indicated group, provided that the designated atom's normal valency is not exceeded, and that the substitution results in a stable compound.

"Unsubstituted" atoms bear all of the hydrogen atoms dictated by their valency. When a substituent is, for example, "keto" then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

"Pharmaceutically acceptable", when used in reference to salts or carriers, refer to materials that are generally accepted as being suitable for administration to or contact with the human body or portions thereof. Pharmaceutically acceptable salts are materials in which the parent compound (e.g., an aminoquinoline compound of Formula (I) or some other therapeutic agent or excipient is modified by making acid or base salts thereof. Examples of pharmaceutically-acceptable salts include, but are not limited to, mineral or organic acid salts of basic residues such as amines, or alkali or organic salts of acidic residues such as carboxylic acids. Pharmaceutically acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without causing excessive toxicity, irritation, allergic response, or other problems or complication, commensurate with a reasonable benefit/risk ratio.

Pharmaceutically acceptable salt forms of the aminoquinoline compounds provided herein are synthesized from the parent compound which contains a basic or acidic moiety by conventional chemical methods. Generally, such salts are prepared, for example, by reacting the free acid or base forms of these compounds with a stoichiometric amount of the appropriate base or acid in water or in an organic solvent, or in a mixture of the two. Generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is incorporated herein by this reference.

"Prodrugs" are considered to be any covalently bonded carriers which release the active parent drug of the aminoquinoline compounds in vivo when such prodrug is administered to a mammalian subject. Prodrugs of the aminoquinoline compounds of the present invention are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples or prodrugs include, but are not limited to, acetate, formate and benzoate derivatives of alcohol and amine functional groups in the aminoquinoline compounds of the present invention, and the like. Compounds that function effectively as prodrugs of the aminoquinoline compounds of the present invention may be identified using routine techniques known in the art. For examples of such prodrug derivatives, see, for example, (a) *Design of Prodrugs,* edited by H. Bundgaard, (Elsevier, 1985) and *Methods in Enzymology,* Vol. 42, p. 309-396, edited by K. Widder, et al. (Academic Press, 1985); (b) *A Textbook of Drug Design and Development,* edited by Krogsgaard-Larsen and H. Bundgaard, Chapter 5 "Design and Application of Prodrugs," by H. Bundgaard p. 113-191 (1991); (c) H. Bundgaard, *Advanced Drug Delivery Reviews,* 8, 1-38 (1992); (d) H. Bundgaard, et al., *Journal of Pharmaceutical Sciences,* 77:285 (1988); and (e) N. Kakeya, et al., *Chem. Pharm. Bull.,* 32: 692 (1984), each of which is specifically incorporated herein by reference.

In addition, the invention also includes solvates, metabolites, and pharmaceutically acceptable salts of the aminoquinoline compounds.

The term "solvate" refers to an aggregate of a molecule with one or more solvent molecules. A "metabolite" is a pharmacologically active product produced through in vivo metabolism in the body of a specified compound or salt thereof. Such products may result for example from the oxidation, reduction, hydrolysis, amidation, deamidation, esterification, deesterification, enzymatic cleavage, and the like, of the administered compound. Accordingly, the invention includes metabolites of the aminoquinoline compounds, including compounds produced by a process comprising contacting a compound of this invention with a mammal for a period of time sufficient to yield a metabolic product thereof.

Pharmaceutical Compositions and Treatment Regimens.

In one aspect, the instant invention provides pharmaceutical compositions which contain a pharmaceutically effective amount of the aminoquinoline compound in a pharmaceutically acceptable carrier (e.g., a diluent, complexing agent, additive, excipient, adjuvant and the like). The aminoquinoline compound can be present for example in a salt form, a micro-crystalline form, a nano-crystalline form, a co-crystalline form, a nanoparticulate form, a mirocparticulate form, and/or an amphiphilic form. The carrier can be an organic or inorganic carrier that is suitable for external, enteral or parenteral applications. The aminoquinoline compounds of the present invention can be compounded, for example, with the usual non-toxic, pharmaceutically acceptable carriers for tablets, pellets, capsules, liposomes, suppositories, intranasal sprays, solutions, emulsions, suspensions, aerosols, targeted chemical delivery systems, and any other form suitable for such use, which are well known in the pharmaceutical formulation arts. Non-limiting examples of carriers that can be used include water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, liquid or aerosol form. In addition auxiliary, stabilizing, thickening and coloring agents and perfumes can be used.

In particular, the present invention provides pharmaceutical compositions useful for treating chronic pain and for prevention of addiction relapse, as described herein. The pharmaceutical compositions comprise at least one aminoquinoline compound as described herein in combination with a pharmaceutically acceptable carrier, vehicle, or diluent, such as an aqueous buffer at a physiologically acceptable pH (e.g., pH 7 to 8.5), a polymer-based nanoparticle vehicle, a liposome, and the like. The pharmaceutical compositions can be delivered in any suitable dosage form, such as a liquid, gel, solid, cream, or paste dosage form. In one embodiment, the compositions can be adapted to give sustained release of the aminoquinoline compound.

In some embodiments, the pharmaceutical compositions include, but are not limited to, those forms suitable for oral, rectal, nasal, topical, (including buccal and sublingual), transdermal, vaginal, parenteral (including intramuscular, intraperitoneal, subcutaneous, and intravenous), spinal (epidural, intrathecal), and central (intracerebroventricular) administration. The compositions can, where appropriate, be conveniently provided in discrete dosage units. The pharmaceutical compositions of the invention can be prepared by any of the methods well known in the pharmaceutical arts. Some preferred modes of administration include intravenous (iv), topical, subcutaneous, oral and spinal. For systemic administration, the aminoquinoline compound generally will be administered the subject at a dosage in the range of about 1 milligram of aminoquinoline compound per kilogram of body mass (mg/kg) to about 200 mg/kg. Typically, the administered dosage should be sufficient to provide a concentration of aminoquinoline compound in the subject of about 1 nanomolar (nM) to about 100 millimolar (mM).

Pharmaceutical formulations suitable for oral administration include capsules, cachets, or tablets, each containing a predetermined amount of one or more of the aminoquinoline compounds, as a powder or granules. In another embodiment, the oral composition is a solution, a suspension, or an emulsion. Alternatively, the aminoquinoline compounds can be provided as a bolus, electuary, or paste. Tablets and capsules for oral administration can contain conventional excipients such as binding agents, fillers, lubricants, disintegrants, colorants, flavoring agents, preservatives, or wetting agents. The tablets can be coated according to methods well known in the art, if desired. Oral liquid preparations include, for example, aqueous or oily suspensions, solutions, emulsions, syrups, or elixirs. Alternatively, the compositions can be provided as a dry product for constitution with water or another suitable vehicle before use. Such liquid preparations can contain conventional additives such as suspending agents, emulsifying agents, non-aqueous vehicles (which may include edible oils), preservatives, and the like. The additives, excipients, and the like typically will be included in the compositions for oral administration within a range of concentrations suitable for their intended use or function in the composition, and which are well known in the pharmaceutical formulation art. The aminoquinoline compounds of the present invention will be included in the compositions within a therapeutically useful and effective concentration range, as determined by routine methods that are well known in the medical and pharmaceutical arts.

Pharmaceutical compositions for parenteral, spinal, or central administration (e.g. by bolus injection or continuous infusion) or injection into amniotic fluid can be provided in unit dose form in ampoules, pre-filled syringes, small volume infusion, or in multi-dose containers, and preferably include an added preservative. The compositions for parenteral administration can be suspensions, solutions, or emulsions, and can contain excipients such as suspending agents, stabilizing agents, and dispersing agents. Alternatively, the aminoquinoline compounds can be provided in powder form, obtained by aseptic isolation of sterile solid or by lyophilization from solution, for constitution with a suitable vehicle, e.g. sterile, pyrogen-free water, before use. The additives, excipients, and the like typically will be included in the compositions for parenteral administration within a range of concentrations suitable for their intended use or function in the composition, and which are well known in the pharmaceutical formulation art. The aminoquinoline compounds of the present invention will be included in the compositions within a therapeutically useful and effective concentration range, as determined by routine methods that are well known in the medical and pharmaceutical arts.

Pharmaceutical compositions for topical administration of the aminoquinoline compounds to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like. The additives, excipients, and the like typically will be included in the compositions for topical administration to the epidermis within a range of concentrations suitable for their intended use or function in the composition, and which are well known in the pharmaceutical formulation art. The aminoquinoline compounds of the present invention will be included in the compositions within a therapeutically useful and effective concentration range, as determined by routine methods that are well known in the medical and pharmaceutical arts.

Pharmaceutical compositions suitable for topical administration in the mouth (e.g., buccal or sublingual administration) include lozenges comprising the aminoquinoline compound in a flavored base, such as sucrose, acacia, or tragacanth; pastilles comprising the aminoquinoline compound in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired. The additives, excipients, and the like typically will be included in the compositions of topical oral administration within a range of concentrations suitable for their intended use or function in the composition, and which are well known in the pharmaceutical formulation art. The aminoquinoline compounds of the present invention will be included in the compositions within a therapeutically useful and effective concentration range, as determined by routine methods that are well known in the medical and pharmaceutical arts.

A pharmaceutical composition suitable for rectal administration comprises a aminoquinoline compound of the present invention in combination with a solid or semisolid (e.g., cream or paste) carrier or vehicle. For example, such rectal compositions can be provided as unit dose suppositories. Suitable carriers or vehicles include cocoa butter and other materials commonly used in the art. The additives, excipients, and the like typically will be included in the compositions of rectal administration within a range of concentrations suitable for their intended use or function in the composition, and which are well known in the pharmaceutical formulation art. The aminoquinoline compounds of the present invention will be included in the compositions within a therapeutically useful and effective concentration range, as determined by routine methods that are well known in the medical and pharmaceutical arts.

According to one embodiment, pharmaceutical compositions of the present invention suitable for vaginal administration are provided as pessaries, tampons, creams, gels, pastes, foams, or sprays containing a peptide of the invention in combination with carriers as are known in the art. Alternatively, compositions suitable for vaginal administration can be delivered in a liquid or solid dosage form. The additives, excipients, and the like typically will be included in the compositions of vaginal administration within a range of concentrations suitable for their intended use or function in the composition, and which are well known in the pharmaceutical formulation art. The aminoquinoline compounds of the present invention will be included in the compositions within a therapeutically useful and effective concentration range, as determined by routine methods that are well known in the medical and pharmaceutical arts.

Pharmaceutical compositions suitable for intra-nasal administration are also encompassed by the present invention. Such intra-nasal compositions comprise a aminoquinoline compound of the invention in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising the peptide. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of the peptide. Alternatively, pharmaceutical compositions for administration by inhalation or insufflation can be provided in the form of a dry powder composition, for example, a powder mix of the aminoquinoline compound and a suitable powder base such as lactose or starch. Such powder composition can be provided in unit dosage form, for example, in capsules, cartridges, gelatin packs, or blister packs, from which the powder can be administered with the aid of an inhalator or insufflator. The additives, excipients, and the like typically will be included in the compositions of intra-nasal administration within a range of concentrations suitable for their intended use or function in the composition, and which are well known in the pharmaceutical formulation art. The aminoquinoline compounds of the present invention will be included in the compositions within a therapeutically useful and effective concentration range, as determined by routine methods that are well known in the medical and pharmaceutical arts.

Optionally, the pharmaceutical compositions of the present invention can include one or more other therapeutic agent, e.g., as a combination therapy. The additional therapeutic agent will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with an aminoquinoline compound of the present invention. For example, the aminoquinoline compound or a composition comprising the compound can be administered in conjunction with an anti-cancer chemotherapeutic agent, an antineoplastic agent, and the like (including materials utilized for the treatment and prevention of metastases), for treating chronic pain associated with cancer therapies. In the case of treating chronic pain, the amino the aminoquinoline compound or a composition comprising the compound can advantageously be administered in conjunction with an analgesic or anti-inflammatory agent (e.g., an opiate, opioid, a non-steroidal anti-inflammatory drug (NSAID), or a steroid), a therapeutic agent for treating a disease (e.g., a disease associated with chronic pain, such as arthritis), and the like, which is different from the aminoquinoline compound.

In another aspect, the present invention provides for the use of the aminoquinoline compounds for treatment of chronic pain. Methods for alleviating chronic pain (e.g., neuropathic pain) comprise administering to a patient suffering from one of the aforementioned conditions an effective amount of a aminoquinoline compound. Preferably, the aminoquinoline compound is administered parenterally or enterally. The dosage of the effective amount of the aminoquinoline compounds can vary depending upon the age and condition of each individual patient to be treated. However, suitable dosages typically range from about 1 mg/kg to about 200 mg/kg, as discussed above. Such a dose can be administered one or more times a day, one or more times a week, one or more times per month, and the like.

As used herein, the terms "reducing", "inhibiting", "blocking", "preventing", "alleviating", "relieving", and "antagonist", when referring to a compound (e.g., a peptide), mean that the compound brings down the occurrence, severity, size, volume, or associated symptoms of a condition, event, or activity by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, or 100% compared to how the condition, event, or activity would normally exist without application of the compound or a composition comprising the compound. The terms "increasing", "elevating", "enhancing", "upregulating", "improving", "activating" and "agonist", when referring to a compound mean that the compound increases the occurrence or activity of a condition, event, or activity by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, 100%, 150%, 200%, 250%, 300%, 400%, 500%, 750%, or 1000% compared to how the condition, event, or activity would normally exist without application of the compound or a composition comprising the compound.

EXAMPLES

The following examples are included to demonstrate certain aspects of the invention. It should be appreciated by those of skill in the art that the techniques disclosed in the examples, which represent techniques known to function well in practicing the invention, can be considered to constitute preferred modes for its practice. However, those of skill in the art should, in light of the present disclosure, appreciate that many changes can be made in the specific disclosed embodiments and still obtain a like or similar result without departing from the spirit and scope of the invention. The examples are provided for illustration purposes only and are not intended to be limiting.

Example 1. Preparation of Compounds of Formula (VI)

Derivatives of kynurenic acid containing a tertiary ureido group, including 5,7-dichloro-4-(3,3-diphenylureido)quinoline-2-carboxylic acid (DCUKA, 7a), may be synthesized, as previously described (Snell et al., 2000) through the use of a reactive carbamoyl chloride intermediate (6a-b). However, it is possible to achieve an improvement on this synthesis due to concomitant ester hydrolysis during the final acylation reaction. One compound embodiment, 5,7-dichloro-4-(3,3-dibutylureido)quinoline-2-carboxylic acid (BCUKA, 7b), was synthesized via this method in the synthesis phases I-IV as explained and illustrated in Scheme 2 (*Reagents and conditions* (I): MeOH, reflux, 16 h. (II): Ph$_2$O, 250° C., 2 h. (III): (a) ClSO$_2$NCO, MeCN, reflux, 2 h. (b) HCl, MeOH, RT, 30 min. (IV): NaH, DMF, 0° C. to RT, 16 h).

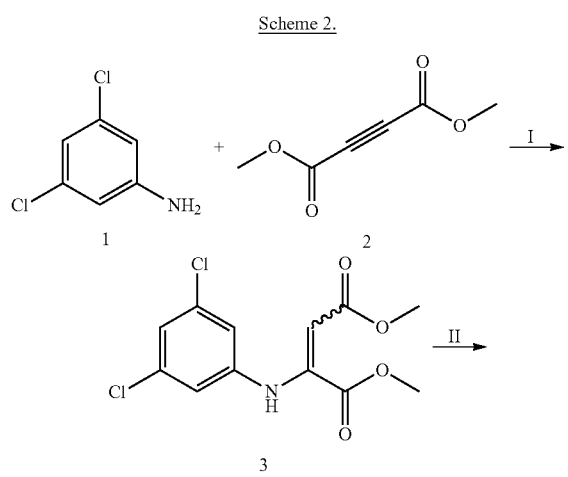

Scheme 2.

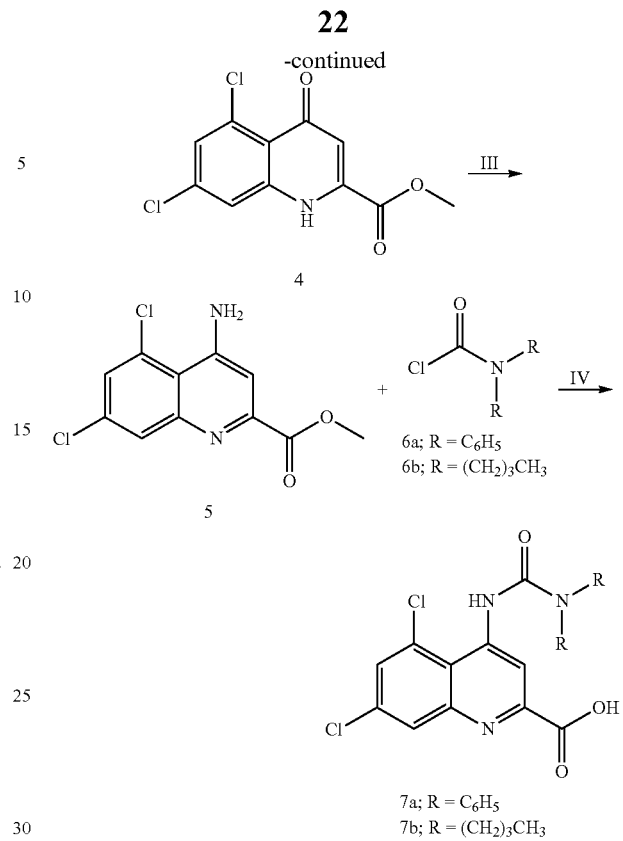

Synthesis Phase I.

3,5-Dichloroaniline (1, 5.00 g, 30.9 mmol) and dimethyl acetylenedicarboxylate (2, 3.80 ml, 30.9 mmol) were combined in anhydrous MeOH (60 ml) under nitrogen, and refluxed for 16 hours. The reaction mixture was cooled to room temperature and evaporated to dryness. The resulting yellow solid was recrystallized from MeOH (twice) to give a mixture of cis and trans isomers of the target dimethyl anilinomaleate (3) as thin yellow crystals (5.23 g, 17.2 mmol). The absorption peak values (in ppm) found in the $^1$H NMR spectrum performed in deuterated DMSO were 3.57 & 3.67 (3H, s), 3.72 & 3.80 (3H, s), 5.35 & 5.58 (1H, s), 6.98 & 7.12 (2H, s$_{app}$), 7.23 & 7.31 (1H, s$_{app}$), 9.52 & 9.64 (1H, br, s).

Synthesis Phase II.

Dimethyl anilinomaleate (3, 3.50 g, 11.5 mmol) was added portion-wise to diphenyl ether (70 ml) at 250° C. The temperature of the resulting solution was maintained at 250° C. for 2 hours, before being cooled to room temperature and diluted with hexanes (100 ml). The resultant precipitate was removed by filtration, washed with hexanes (50 ml), and suspended in refluxing ethanol, before being filtered to remove soluble impurities. The solid filtrand was dried under vacuum to give the desired quinolone carboxylate (4) as an off-white solid (3.10 g, 11.4 mmol). The absorption peak values (in ppm) found in the $^1$H NMR spectrum performed in deuterated DMSO were 3.96 (3H, s), 6.59 (1H, s), 7.42 (1H, s), 7.97 (1H, s), 12.05 (1H, br).

Synthesis Phase III.

Chlorosulfonyl isocyanate (1.20 ml, 13.8 mmol) was added to a slurry of quinoline carboxylate (4, 2.50 g, 9.19 mmol) in anhydrous MeCN (35 ml) at room temperature. The mixture was brought to reflux for 1.5 hours, at which point the heating was stopped and a 1.0M solution of HCl in anhydrous MeOH (20 ml) was added. The reaction mixture was allowed to cool to room temperature with stirring until a precipitate formed after 1 hour. The precipitate was removed via filtration, washed with MeCN, and air dried. The filter cake was suspended in water (50 ml) to which saturated sodium carbonate solution (~5 ml) was added to pH 10, causing thickening of the suspension. The resultant solid was collected by filtration, washed with cold water and dried under vacuum (40° C.) to give the target aminoquinoline (5) as an off-white solid (1.82 g, 6.71 mmol). The absorption peak values (in ppm) found in the $^1$H NMR spectrum performed in deuterated DMSO were 4.05 (3H, s), 6.04 (2H, s), 7.33 (1H, s), 7.47 (1H, d, J=1.9 Hz), 8.10 (1H, d, J=1.9 Hz).

Synthesis Phase IV.

The acylation of aminoquinoline (5), with concomitant ester hydrolysis, to yield 5,7-dichloro-4-(3,3-dibutylureido)quinoline-2-carboxylic acid (DBCUKA, 7b) was performed as follows; N,N-dibutylcarbamoyl chloride (6b, 96 mg, 0.50 mmol) and aminoquinoline (5, 113 mg, 0.42 mmol) were dissolved in anhydrous DMF (2 ml) and cooled to 0° C. Sodium hydride dispersion in mineral oil (60%, 35 mg, 0.83 mmol) was added and the mixture was allowed to warm to room temperature and stirred for 16 hours. The reaction was quenched via addition to saturated NH$_4$Cl solution (1 ml), followed by adjustment to pH 3 with 1.0M aqueous HCl. Extraction with EtOAc (2×10 ml) followed by washing with saturated brine (5 ml) and drying (Na$_2$SO$_4$) gave the crude product as a pale yellow oil. Compound purification via silica gel chromatography (9:1 DCM:MeOH) gave 5,7-dichloro-4-(3,3-dibutylureido)quinoline-2-carboxylic acid (DBCUKA, 7b) as a pale yellow solid (82 mg, 0.20 mmol). The absorption peak values (in ppm) found in the $^1$H NMR spectrum performed in CDCl$_3$ were 1.00 (6H, t, J=7.4 Hz), 1.36-1.45 (4H, m), 1.64-1.72 (4H, m), 3.39-3.45 (4H, m), 5.17 (1H, s), 7.69 (1H, s), 8.30 (1H, s), 9.16 (1H, s).

Carbamoyl chlorides are limited in their commercial availability, and, furthermore, are characterized by high reactivity, especially to hydrolysis, and subsequent poor stability. This is particularly evident in the case of mono-n-substituted carbamoyl chlorides. Therefore, in order to prepare mono-n-substituted analogues of kynurenic acid it was advantageous to utilize alternative carbamoyl cation equivalents, with attenuated reactivity. Carbamoyl imidazoles (e.g. 9a-d) have been shown to be suitable reactive species for the synthesis of a variety of functional groups including ureas, thioureas, carbamates, thiocarbamates and amides. (Grzyb et al., 2005) Derivatives of kynurenic acid containing a secondary ureido group were prepared using this approach in synthesis phases V-VII as explained and illustrated in Scheme 3 (*Reagents and conditions*: (V): CDI, DCM, 0° C. to RT, 16 h. (VI): 5, NaH, DMF, 0° C. to RT, 16 h. (VII) TFA, DCM, RT, 16 h.).

Scheme 3.

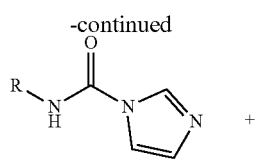

8a; R = CH$_2$CH$_2$CH$_2$CH$_3$
8b; R = CH$_2$CH$_2$CH$_2$N(CH$_3$)$_2$
8c; R = CH$_2$CH$_2$CH$_2$NHBoc
8d; R = CH$_2$CH$_2$CH$_2$N(CH$_3$)Boc

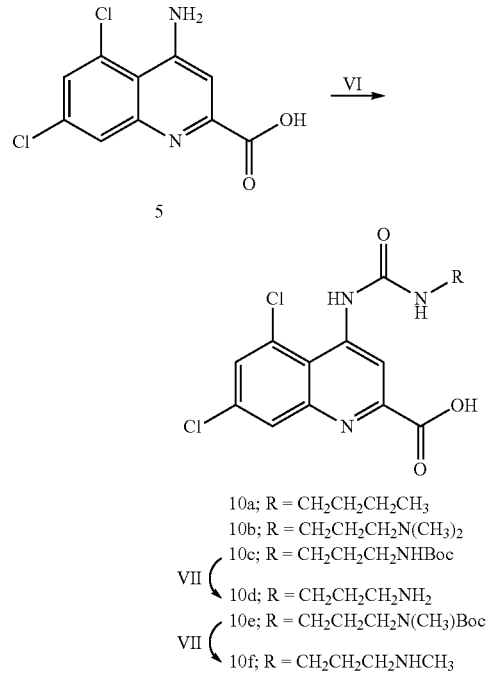

-continued

9a; R = CH$_2$CH$_2$CH$_2$CH$_3$
9b; R = CH$_2$CH$_2$CH$_2$N(CH$_3$)$_2$
9c; R = CH$_2$CH$_2$CH$_2$NHBoc
9d; R = CH$_2$CH$_2$CH$_2$N(CH$_3$)Boc

10a; R = CH$_2$CH$_2$CH$_2$CH$_3$
10b; R = CH$_2$CH$_2$CH$_2$N(CH$_3$)$_2$
10c; R = CH$_2$CH$_2$CH$_2$NHBoc
10d; R = CH$_2$CH$_2$CH$_2$NH$_2$
10e; R = CH$_2$CH$_2$CH$_2$N(CH$_3$)Boc
10f; R = CH$_2$CH$_2$CH$_2$NHCH$_3$

General Example of Synthesis Phase V.

n-Butylamine (8a, 100 µl, 74 mg, 1.01 mmol) in DCM (1 ml) was added to a solution of CDI (0.197 g, 1.21 mmol) in DCM (5 ml) at 0° C., before the reaction mixture was allowed to warm to RT and stirred overnight. The solution was diluted with DCM (10 ml) washed with water (2×10 ml) and brine (10 ml), dried (Na$_2$SO$_4$) and evaporated to dryness to give the target carbamoyl imidazole (9a) as a colorless oil (115 mg, 0.69 mmol). The absorption peak values (in ppm) found in the $^1$H NMR spectrum performed in CDCl$_3$ were 0.97 (3H, t, J=7.4 Hz), 1.42 (2H, qt, J=7.6, 7.3 Hz), 1.63 (2H, tt, J=7.3, 7.0 Hz), 3.44 (2H, dt, J=7.0, 6.7 Hz), 6.75 (1H, br), 7.07 (1H, s), 7.42 (1H, s), 8.17 (1H, s).

N-(3-(Dimethylamino)propyl)-1H-imidazole-1-carboxamide (9b) was prepared from 3-dimethylaminopropylamine (8b) as described in synthesis phase V. The absorption peak values (in ppm) found in the $^1$H NMR spectrum performed in CDCl$_3$ were 1.77 (2H, tt, J=5.7, 5.5 Hz), 2.32 (6H, s), 2.56 (2H, t, J=5.5 Hz), 3.54 (2H, dt, J=5.9, 5.5 Hz), 7.07 (11, s), 7.27 (11, s), 8.04 (1H, s), 9.34 (1H, br).

tert-Butyl (3-(1H-imidazole-1-carboxamido)propyl)carbamate (9c) was prepared from tert-butyl (3-aminopropyl)carbamate (8c) as described in synthesis phase V. The absorption peak values (in ppm) found in the $^1$H NMR spectrum performed in CDCl$_3$ were 1.49 (9H, s), 1.73 (2H, tt, J=5.8, 5.7 Hz), 3.30 (2H, dt, J=6.4, 5.7 Hz), 3.48 (2H, dt, J=6.0, 5.8 Hz), 4.91 (1H, br), 7.11 (1H, s), 7.52 (1H, s), 7.92 (1H, br), 8.25 (1H, s).

tert-Butyl (3-(1H-imidazole-1-carboxamido)propyl)(methyl)carbamate (9d) was prepared from N-(3-aminopropyl)-N-methylcarbamic acid tert-butyl ester (8d) as described in synthesis phase V. The absorption peak values (in ppm) found in the $^1$H NMR spectrum performed in CDCl$_3$ were 1.49 (9H, s), 1.74-1.80 (2H, br), 2.87 (3H, s), 3.35-3.43 (4H, m), 7.09 (1H, s), 7.53 (1H, s), 8.11 (1H, br), 8.25 (1H, s).

General Example of Synthesis Phase VI.

It was possible to use carbamoyl imidazoles (9a-d) in a manner analogous to carbamoyl chlorides in synthesis phase IV, allowing for a single step involving acylation of the amino quinoline (5) and simultaneous ester hydrolysis. The approach was utilized for the synthesis of 4-(3-butylureido)-5,7-dichloroquinoline-2-carboxylic acid (10a) as follows; N-butyl-1H-imidazole-1-carboxamide (9a, 125 mg, 0.95 mmol) and aminoquinoline (5, 215 mg, 0.79 mmol) were dissolved in anhydrous DMF (4 ml) and cooled to 0° C. Sodium hydride dispersion in mineral oil (60%/a, 63 mg, 1.58 mmol) was added and the mixture was allowed to warm to room temperature and stirred for 16 hours. The reaction was quenched via addition to saturated NH$_4$Cl solution (3 ml), followed by adjustment to pH 3 with 1.0M aqueous HCl. Extraction with EtOAc (2×20 ml) followed by washing with saturated brine (10 ml) and drying (Na$_2$SO$_4$) gave the crude product as a pale orange residue. Compound purification via reverse phase (C18) silica gel chromatography (1:1 H$_2$O:MeCN) gave 4-(3-butylureido)-5,7-dichloroquinoline-2-carboxylic acid (10a) as a beige solid (142 mg, 0.39 mmol). The absorption peak values (in ppm) found in the $^1$H NMR spectrum performed in deuterated DMSO were 0.92 (3H, t, J=7.3 Hz), 1.31-1.38 (2H, m), 1.44-1.52 (2H, m), 3.16 (2H, dt, J=6.6, 6.0 Hz), 7.47 (1H, br), 7.87 (1H, d, J=2.2 Hz), 8.11 (1H, d, J=2.2 Hz), 8.68 (1H, s), 9.12 (1H, br).

5,7-Dichloro-4-(3-(3-(dimethylamino)propyl)ureido)quinoline-2-carboxylic acid (10b) was prepared from N-(3-(dimethylamino)propyl)-1H-imidazole-1-carboxamide (9b) as described in synthesis phase VI. Due to the zwitterionic nature of the target compound, acidification to pH 1/2 was performed with TFA prior to reverse phase (C18) chromatography to afford the product as the TFA salt form. The absorption peak values (in ppm) found in the $^1$H NMR spectrum performed in D$_2$O were 1.87-2.00 (2H, m), 2.87 (6H, s), 3.12-3.20 (2H, m), 3.21-3.31 (2H, m), 7.13 (1H, s), 7.48 (1H, s), 8.06 (1H, s). The absorption peak value (in ppm) found in the $^{19}$F NMR spectrum performed in D$_2$O was −75.6.

4-(3-(3-((tert-Butoxycarbonyl)amino)propyl)ureido)-5,7-dichloroquinoline-2-carboxylic acid (10c) was prepared from tert-butyl (3-(1H-imidazole-1-carboxamido)propyl)carbamate (9c) as described in synthesis phase VI. The absorption peak values (in ppm) found in the $^1$H NMR spectrum performed in deuterated DMSO were 1.39 (9H, s), 1.60 (2H, tt, J=6.8, 6.6 Hz), 2.95-3.02 (2H, m), 3.12-3.18 (2H, m), 6.83 (1H, br), 7.45 (1H, br), 7.85 (1H, s), 8.10 (1H, s), 8.65 (1H, s), 9.15 (1H, br).

4-(3-(3-((tert-Butoxycarbonyl)(methyl)amino)propyl)ureido)-5,7-dichloroquinoline-2-carboxylic acid (10e) was prepared from tert-butyl (3-(1H-imidazole-1-carboxamido)propyl)methyl carbamate (9d) as described in synthesis phase VI. The absorption peak values (in ppm) found in the $^1$H NMR spectrum performed in deuterated DMSO were 1.39 (9H, s), 1.63-1.71 (2H, m), 2.79 (3H, s), 3.08-3.16 (2H, m), 3.19-3.26 (2H, m), 7.27 (1H, br), 7.68 (1H, d, J=1.8 Hz), 8.29 (1H, d, J=1.8 Hz), 8.40 (11, br), 8.97 (1H, br).

General Example of Synthesis Phase VII.

TFA (173 µL, 2.25 mmol) was added to a solution of Boc-protected amine (10c, 103 mg, 0.23 mmol) in DCM (4 ml). After stirring at room temperature for 16 hours, the solvent was removed under reduced pressure and the residue was purified directly by reverse phase chromatography (C18, 1:1 H$_2$O:MeCN) to give the TFA salt form of 4-(3-(3-aminopropyl)ureido)-5,7-dichloroquinoline-2-carboxylic acid (10d) as a white solid (64 mg, 0.14 mmol). The absorption peak values (in ppm) found in the $^1$H NMR spectrum performed in D$_2$O (1.0% TFA) were 1.61 (2H, tt, J=6.9, 7.1 Hz), 2.72 (2H, t, J=7.1 Hz), 3.04 (2H, t, J=6.9 Hz), 7.62 (1H, s), 7.89 (1H, s), 8.71 (1H, s).

5,7-Dichloro-4-(3-(3-(methylamino)propyl)ureido)quinoline-2-carboxylic acid (10f) was prepared from 4-(3-(3-((tert-Butoxycarbonyl)(methyl)amino)propyl)ureido)-5,7-dichloroquinoline-2-carboxylic acid (10e) as described in synthesis phase VI. The absorption peak values (in ppm) found in the $^1$H NMR spectrum performed in D$_2$O (1.0% TFA) were 1.81 (2H, tt, J=6.8, 7.7 Hz), 2.55 (3H, s), 2.94 (2H, t, J=7.8 Hz), 3.22 (2H, t, J=6.8 Hz), 7.78 (1H, d, J=1.9 Hz), 8.01 (1H, d, J=1.9 Hz), 8.77 (1H, s). The absorption peak value (in ppm) found in the $^{19}$F NMR spectrum performed in D$_2$O was −73.4. The compound structures are shown in Scheme 4.

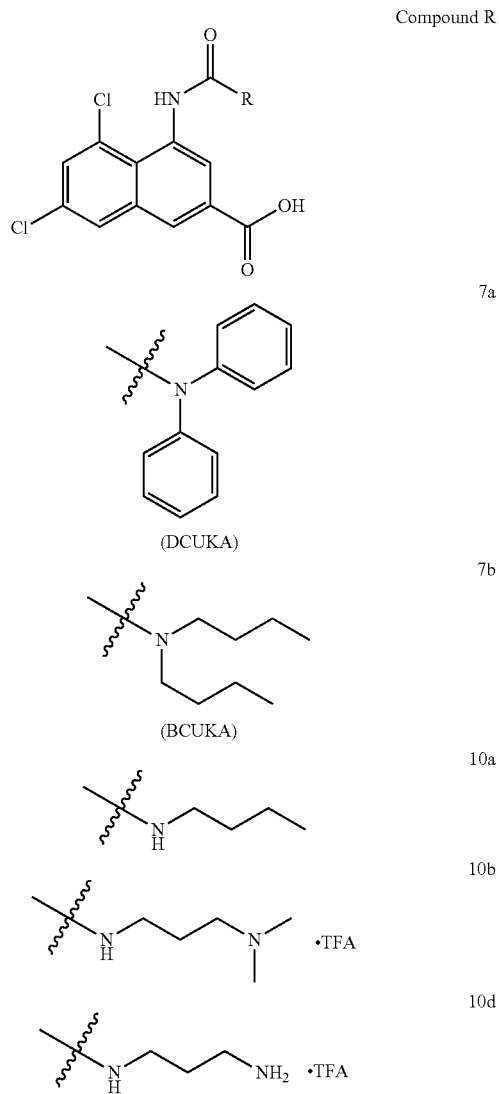

Scheme 4.

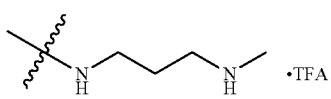

Synthesis of 3-(2-butyryl-5,7-dichloroquinolin-4-yl)-1,1-diphenylurea

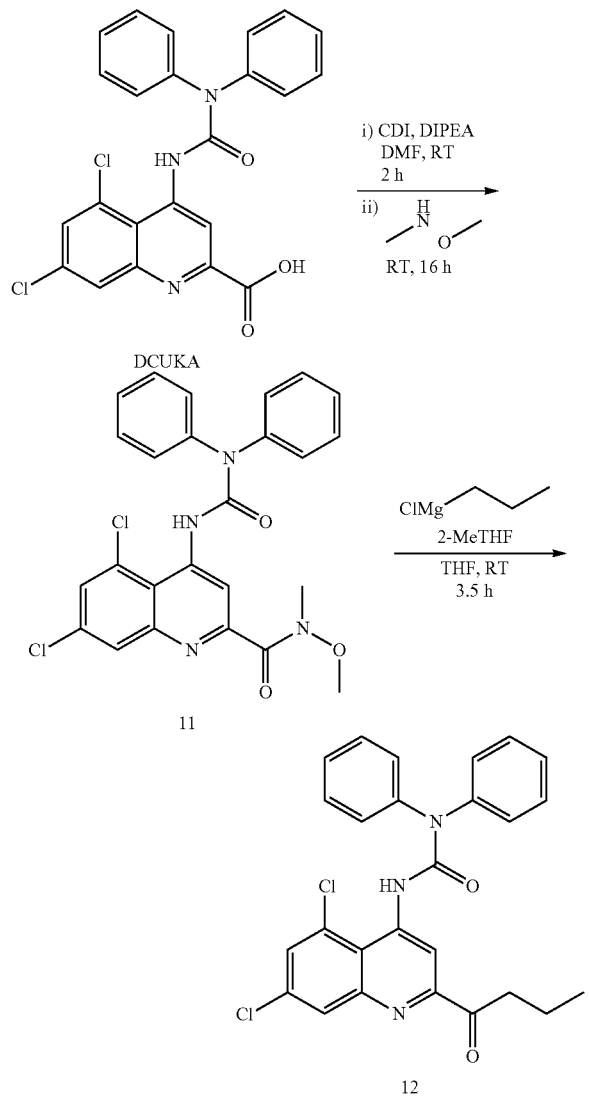

A. 5,7-Dichloro-4-(3,3-diphenylureido)-N-methoxy-N-methylquinoline-2-carboxamide (11). Carbonyldiimidazole (72 mg, 0.44 mmol) and diisopropylethylamine (115 uL, 0.66 mmol) were added to a solution of 5,7-dichloro-4-(3,3-diphenylureido)quinoline-2-carboxylic acid (DCUKA; 100 mg, 0.22 mmol) in dry N,N-dimethylformamide (15 mL). The reaction mixture was stirred at room temperature under nitrogen for 2 hours, before N,O-dimethylhydroxylamine hydrochloride (86 mg, 0.88 mmol) was added. The resulting pale yellow solution was stirred at room temperature for a further 16 hours, at which point the solvent was removed under reduced pressure and the residue was dissolved in ethyl acetate (20 mL) and washed with saturated sodium hydrogen carbonate solution (2×15 mL) and 0.1M HCl (2×15 mL), followed by water (15 mL) and brine (10 mL). The organic phase was dried (MgSO$_4$) and evaporated to dryness. The target compound was obtained following purification by chromatography on silica (1:1 Hexanes:EtOAc) as a white solid (81 mg, 0.16 mmol, 73%). Rf 0.33 (1:1 Hexanes:EtOAc); M.p. 207-210° C.; 1H NMR (400 MHz, CDCl$_3$) 3.40 (3H, s), 3.75 (3H, br), 7.28 (1H, s), 7.34-7.37 (2H, m), 7.41-7.49 (8H, m), 8.03 (1H, d, J=2.0 Hz), 8.87 (1H, s), 9.39 (1H, s).

B. 3-(2-Butyryl-5,7-dichloroquinolin-4-yl)-1,1-diphenylurea (12). A n-Propylmagnesium chloride solution in 2-methyltetrahydroduran (1.0M, 1.12 mL, 1.12 mmol) was added dropwise to a solution of 5,7-dichloro-4-(3,3-diphenylureido)-N-methoxy-N-methylquinoline-2-carboxamide (11, 70 mg, 0.14 mmol) in dry tetrahydrofuran (10 mL) at −10° C., under nitrogen. Following addition, the reaction mixture was stirred at −10° C. for 30 min, before being allowed to warm to room temperature and stirred for an additional 3 hrs. The reaction was quenched with saturated ammonium chloride solution (10 mL) and the product, ketone 12, was extracted with ethyl acetate (3×15 mL). The organic extract was washed with brine (10 mL) and dried (MgSO$_4$) before being evaporated to dryness. The residue was purified via chromatography on silica (4:1 Hexanes:EtOAc) to afford the target compound as a pale yellow solid (32 mg, 0.07 mmol, 47%). Rf 0.45 (4:1 Hexanes:EtOAc); M.p. 161-164° C.; 1H NMR (400 MHz, CDCl$_3$) 1.03 (3H, t, J=7.4 Hz), 1.80 (21, qt, J=7.3, 7.4 Hz), 3.24 (21, t, J=7.3 Hz), 7.28 (1H, s), 7.34-7.38 (2H, m), 7.42-7.49 (8H, m), 8.09 (1H, d, J=2.1 Hz), 9.15 (1H, s), 9.31 (1H, s).

Synthesis of 5,7-dichloro-4-(3,3-diphenylureido)-N-ethylquinoline-2-carboxamide (13)

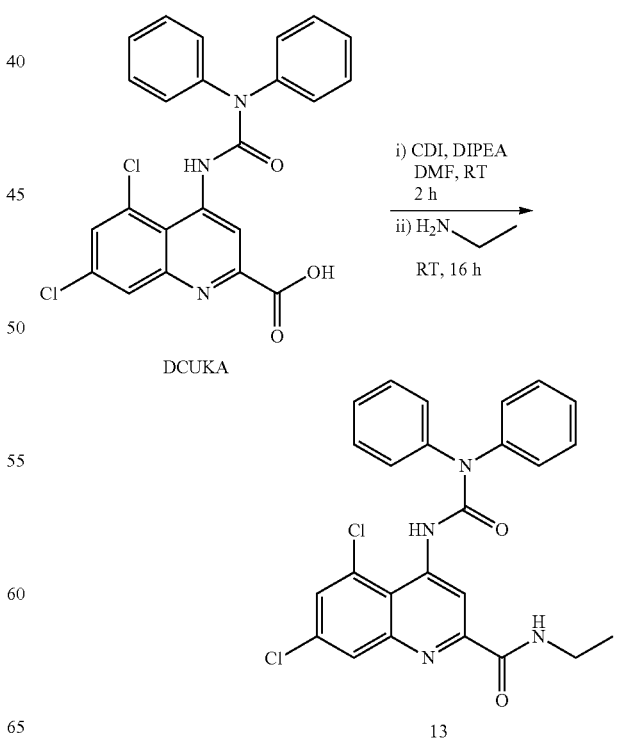

Carbonyldiimidazole (143 mg, 0.88 mmol) and diisoproylethylamine (230 uL, 1.32 mmol) were added to a solution of 5,7-dichloro-4-(3,3-diphenylureido)quinoline-2-carboxylic acid (DCUKA; 200 mg, 0.44 mmol) in dry N,N-dimethylformamide (25 mL). The reaction mixture was stirred at room temperature under nitrogen for 2 hours, before ethylamine in THF (2.0M, 0.66 mL, 1.32 mmol) was added. The resulting pale yellow solution was stirred at room temperature for a further 16 hours, at which point the reaction was complete. The solvent was removed under reduced pressure and the residue was dissolved in ethyl acetate (50 mL) and washed with saturated sodium hydrogen carbonate solution (2×30 mL) and 0.1M HCl (2×30 mL), followed by water (25 mL) and brine (25 mL). The organic phase was dried (MgSO$_4$) and evaporated to dryness. The target ethylamide 13 was via silica gel chromatography (1:1 Hexanes:EtOAc) as an off-white solid (148 mg, 0.31 mmol, 71%). Rf 0.43 (1:1 Hexanes:EtOAc); M.p. 202-205° C.; 1H NMR (400 MHz, CDCl$_3$) 1.31 (3H, t, J=7.2 Hz), 3.56 (2H, q, J=7.2 Hz), 7.28 (1H, s), 7.32-7.37 (2H, m), 7.41-7.49 (8H, m), 7.99 (1H, s), 8.01 (1H, br), 9.28 (1H, s), 9.32 (1H, s).

Synthesis of 5,7-dichloro-4-(3,3-diphenylureido)-N-isopropylquinoline-2-carboxamide (14)

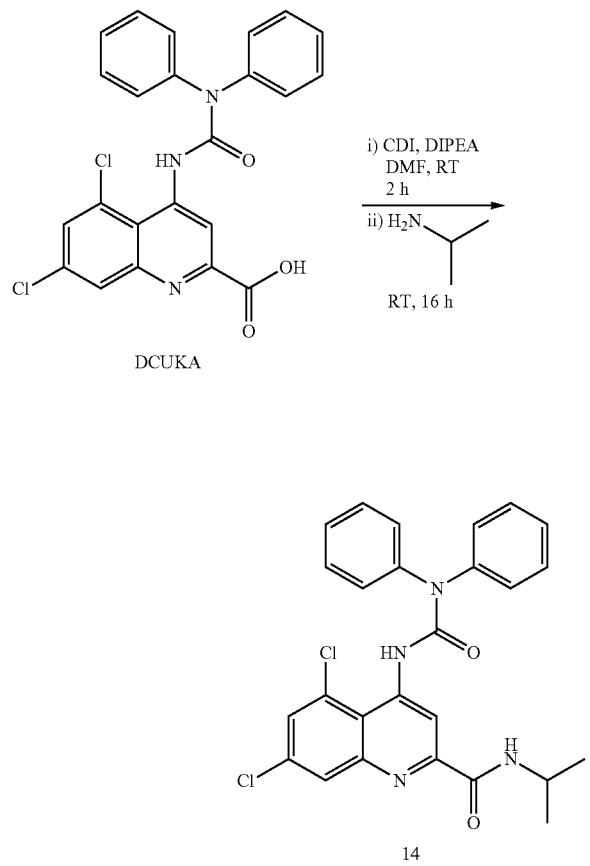

Carbonyldiimidazole (146 mg, 0.88 mmol) and diisoproylethylamine (230 uL, 1.32 mmol) were added to a solution of 5,7-dichloro-4-(3,3-diphenylureido)quinoline-2-carboxylic acid (DCUKA; 200 mg, 0.44 mmol) in dry N,N-dimethylformamide (25 mL). The reaction mixture was stirred at room temperature under nitrogen for 2 hours, before isopropylamine (110 µL, 1.32 mmol) was added. The resulting pale yellow solution was stirred at room temperature for a further 16 hours, at which point the solvent was removed under reduced pressure and the residue was dissolved in ethyl acetate (50 mL) and washed with saturated sodium hydrogen carbonate solution (2×30 mL) and 0.1M HCl (2×30 mL), followed by water (25 mL) and brine (25 mL). The organic phase was dried (MgSO$_4$) and evaporated to dryness. The target isopropylamide 14 was via silica gel chromatography (1:1 Hexanes:EtOAc) as a white solid (182 mg, 0.37 mmol, 84%). Rf 0.52 (1:1 Hexanes:EtOAc); M.p. 197-199° C.; 1H NMR (400 MHz, DMSO-d6) 1.23 (6H, d, J=6.8 Hz), 4.15 (1H, m), 7.34-7.39 (2H, m), 7.46-7.55 (8H, m), 7.76 (1H, d, J=1.9 Hz), 8.11 (1H, d, J=1.9 Hz), 8.55 (1H, d, J=8.2 Hz), 9.00 (1H, s), 9.21 (1H, s).

Example 2. Effect of DCUK Compounds on Ligand Binding to Delta Opiate Receptor, Cannabinoid CB1 Receptor and GABA-A Receptor and Other Neurotransmitter Receptors, Ion Channels and Transporters This example compares the effect of DCUKA, BCUKA, or DCUK-OEt on the binding of ligands defining the delta opiate receptor, the cannabinoid CB1 receptor, and the agonist and benzodiazepine sites on the GABA-receptor, as well as other receptors and neurotransmitter transporters, performed using membrane preparations from cultured cells or from rat brain.

These assays were performed by the Psychoactive Drug Screening Program (PDSP) (NIMH). Detailed methods can be found at the PDSP website PDSP(dot)med(dot)unc(dot)edu/pdspw/binding(dot)php. Table 1 is taken from the PDSP website, as well as the lists the cell lines used for binding assays in Tables A, B, and C. The following brief description, including Tables 1, A, B, and C, is quoted from the website.

"To make membrane fractions from stably transfected cell lines, cells are subcultured in 15-cm dishes and grown to 90% confluency. The next day, the cells are rinsed with PBS, scraped off into 50 ml conical tubes, and pelleted by centrifugation (1000×g, 10 min at 4° C.). The cell pellet is resuspended in chilled (4° C.) lysis buffer (50 mM Tris HCl buffer, pH 7.4) and triturated gently for hypotonic lysis. The suspension is then centrifuged at 21,000×g for 20 min at 4° C. to obtain a crude membrane fraction pellet. The fresh membrane pellet is then resuspended in 3 volumes of cold lysis buffer, and is immediately subjected to the Bradford protein assay to determine protein concentration, followed by a saturation binding assay (see following section for detail) to determine receptor expression level and the affinity of a selected radioligand (K$_d$). Based on the receptor expression level and the K$_d$ value, the fresh membrane suspension is stored at −80° C. freezer in small aliquots, such that one aliquot is sufficient for one 96-well plate to have at least 500 cpm/well when assayed at 0.5-1.0×K$_d$ value of the appropriate radioligand."

TABLE 1

List of cell lines and targets used by the PDSP to make membrane pellets for binding assays.

| Receptor | Note | Parental cells | Media (see detail below the table) |
|---|---|---|---|
| Serotonin (5HT) | | | |
| 5-HT1A | | stable CHO | 500 G418 |
| 5-HT1B | | stable HEK | 500 G418 |
| 5-HT1D | * | HEKT | COS/HEK |
| 5-HT1E | | stable HEK | 500 G418 |
| 5-HT2A (rat) | | stable 3T3 | 500 G418 |
| 5-HT2A | * | HEKT | COS/HEK |
| 5-HT2B | | stable HEK | 2 µg/ml Puromycin |
| 5-HT2C | | Flp-IN HEK | DMEM 100 µg/ml Hygromycin B |
| 5-HT3 | * | HEKT | COS/HEK |
| 5-HT5A | | Flp-In CHO | DMEM/F-12 200 µg/ml Hygromycin B |
| 5-HT6 | | stable HEK | 500 G418 |
| 5-HT7A | | stable HEK | 2 µg/ml Puromycin |
| Dopamine | | | |
| D1 | * | HEKT | COS/HEK |
| D2 | | stable fibroblast | COS/HEK |
| D2L | | stable CHO | F-12/10% FBS 400G418 |
| D3 (rat) | * | HEKT | COS/HEK |
| D3 | * | HEKT | COS/HEK |
| D4 | | stable | DMEM/F12 10% CS Fe+ |
| D5 | * | HEKT | COS/HEK |
| Opioid | | | |
| Mu, MOR | | stable HEK | 200 G418 |
| Delta, DOR | | stable HEK | 200 G418 |
| Kappa, KOR (rat) | | stable HEK | 500 G418 |
| Kappa, KOR | | stable HEK | 500 G418 |
| Nociceptin, NOP | * | HEKT | COS/HEK |
| Neurotransmitter Transporters | | | |
| SERT | | stable HEK | 500 G418 |
| NET | | stable HEK | hNET (250 G418) |
| DAT | | stable HEK | hDAT (350 G418) |
| Vasopressin and Oxytocin | | | |
| V1A | | stable CHO | V1A & OT media |
| V2 | | stable CHO | V2 & V1B media |
| V1B | | stable CHO | V2 & V1B media |
| OT | | stable CHO | V1A & OT media |
| Prostaglandin | | | |
| EP-3 | * | HEKT | COS/HEK |
| EP-4 | * | HEKT | COS/HEK |
| Adrenergic | | | |
| alpha 1A | | stable | 500 G418 |
| alpha 1B | * | HEKT | |
| alpha 1D | | stable | 500 G418 |
| alpha 2A | | stable MDCK | 500 G418 |
| alpha 2B | * | HEKT | COS/HEK |
| alpha 2C | | stable MDCK | 500 G418 |
| beta 1 | | CHO Flp-In | DMEM/F12 200 µg/ml Hygromycin B |
| beta 2 | | HEK Flp-In | DMEM 100 µg/ml Hygromycin B |
| beta 3 | | HEK Flp-In | DMEM 100 µg/ml Hygromycin B |
| Muscarinic acetylcholine | | | |
| M1 | | stable CHO | 500 G418 |
| M2 | | stable CHO | 500 G418 |
| M3 | | stable CHO | 500 G418 |
| M3D | | CHO Flp-In | DMEM/F12 100 µg/ml Hygromycin B |
| M4 | | stable CHO | 10% FBS F12 |
| M5 | | stable CHO | 500 G418 |
| Nicotinic acetylcholine | | | |
| α2β3 | | HEK | 500 G418 |
| α2β4 | | HEK | 500 G418 |
| α3β2 | | HEK | 500 G418 |
| α3β4 | | HEK | 500 G418 |
| α4β2 | | HEK | 500 G418 |
| α4β4 | | HEK | 500 G418 |
| α7 | | HEK | 500 G418 |

TABLE 1-continued

List of cell lines and targets used by the PDSP to make membrane pellets for binding assays.

Histamine

| | | |
|---|---|---|
| H1 | stable HEK | 500 G418 |
| H2 (in progress) | stable HEK | 500 G418 |
| H3 | HEK Flp-In | DMEM 100 µg/ml Hygromycin B |
| H4 (in progress) | | 500 G418 |

Cannabinoid

| | | |
|---|---|---|
| CB1 (in progress) | HEK | 500 G418 |
| CB1 | HEK Flp-In | DMEM 100 µg/ml Hygromycin B |
| CB2 | HEK Flp-In | DMEM 100 µg/ml Hygromycin B |

Adenosine

| | | | |
|---|---|---|---|
| A1 | * | HEKT | COS/HEK |
| A2A | * | HEKT | COS/HEK |
| A2A | | HEK | 500 G418 |
| A2B | * | HEKT | COS/HEK |
| A3 | * | HEKT | COS/HEK |

Melanocortin

| | | | |
|---|---|---|---|
| MC-1 | * | HEKT | COS/HEK |
| MC-2 | * | HEKT | COS/HEK |
| MC-3 | * | HEKT | COS/HEK |
| MC-4 | * | HEKT | COS/HEK |
| MC-5 | * | HEKT | COS/HEK |

Purinergic P2Y

| | | |
|---|---|---|
| P2Y1 | Astrocyte line | 500 G418 |
| P2Y2 | Astrocyte line | 500 G418 |
| P2Y4 | Astrocyte line | 500 G418 |
| P2Y6 | Astrocyte line | 500 G418 |
| P2Y11 | Astrocyte line | 500 G418 |
| P2Y12 | Astrocyte line | 500 G418 |

Trace Amine

| | | | |
|---|---|---|---|
| TA-1 | * | HEKT | COS/HEK |
| TA-3 | * | HEKT | COS/HEK |
| TA-4 | * | HEKT | COS/HEK |
| TA-5 | * | HEKT | COS/HEK |

| Receptor | Note | Parental cells Media (see detail below the table) | Media (see detail below the table) |
|---|---|---|---|

Lysophospholide (LPA)

| | | | |
|---|---|---|---|
| LPA1 | * | HEKT | COS/HEK |
| LPA2 | * | HEKT | COS/HEK |
| LPA3 | * | HEKT | COS/HEK |

Tachykinin (NK)

| | | |
|---|---|---|
| NK1 | HEK | 500 G418 |
| NK2 | HEK | 500 G418 |
| NK3 | HEK | 500 G418 | mGluRs

| | | | |
|---|---|---|---|
| mGluR1 (in progress) | * | HEKT | 500 G418 |
| mGluR2 (in progress) | * | HEKT | 500 G418 |
| mGluR3 (in progress) | * | HEKT | 500 G418 |
| mGluR4 (in progress) | * | HEKT | 500 G418 |
| mGluR5 | | CHO | 2 µg/ml Puromycin |
| mGluR5 (in progress) | * | HEKT | 500 G418 |
| mGluR6 (in progress) | * | HEKT | 500 G418 |
| mGluR7 (in progress) | * | HEKT | 500 G418 |
| mGluR8 (in progress) | * | HEKT | 500 G418 |

Others

| | | | |
|---|---|---|---|
| Ghrelin | | HEK Flp-In | DMEM 100 µg/ml Hygromycin B |
| PAR1 | | Lung Fibroblast, PAR1 KO | 500 G418 |
| SMO | * | HEKT | COS/HEK |
| SMO (in progress) | | HEK | 500 G418 |
| CCK2 | | CHO | 500 G418 |
| Orexin-2 | * | HEKT | COS/HEK |
| GPR58 | * | HEKT | COS/HEK |
| GPR61 | * | HEKT | COS/HEK |
| GPR62 | * | HEKT | COS/HEK |
| GPR40 | * | HEKT | COS/HEK |
| GPR41 | * | HEKT | COS/HEK |
| GPR43 | * | HEKT | COS/HEK |

TABLE 1-continued

List of cell lines and targets used by the PDSP to make membrane pellets for binding assays.

| | | | |
|---|---|---|---|
| I1-1 imidazoline | * | HEKT | COS/HEK |
| HERG-K+ Channel | | HEK | 500 ug/ml G418 |
| PC12 | | | COS/HEK |

All clones are stable lines, whereas transiently transfected cells are marked with "*". Clones are human unless noted. From PDSP website.

"Radioligands and their concentrations, reference compounds, and buffers for radioligand binding assays are listed in Tables A, B, and C. The concentrations of radioligand used for competition binding assay are usually at or near the $K_d$ value or as listed. Historical reference $K_i$ values from the last 6 months are also included."

TABLE A

Opioid receptors. From PDSP website

| Target | Radioligand | $K_d$ for [$^3$H] Compound binding in nM (N) | References | Reference $K_i$ (nM) |
|---|---|---|---|---|
| DOR | [$^3$H]DADLE | 1.85 ± 0.15 (2) | Naltrindole | 0.81 ± 0.08 |
| KOR | [$^3$H]U69593 | 1.07 ± 0.10 (21) | Salvinorin A | 1.93 ± 0.45 |
| MOR | [$^3$H]DAMGO | 1.73 ± 0.14 (6) | DAMGO, Morphine | 2.62 ± 0.22 |
| NOP | [$^3$H]N/OFQ | 0.74 ± 0.22 (4) | JDTiC B612111 | 12.05 ± 1.47 |
| | | | | 6.58 ± 1.42 |

Standard binding buffer: 50 mM Tris HCl, 10 mM MgCl$_2$, 0.1 mM EDTA, pH 7.4, RT
Standard wash buffer: 50 mM Tris HCl, pH 7.4, 4° C. to 8° C.

TABLE B

Cannabinoid receptors From PDSP website

| Target | Radioligand | $K_d$ for [$^3$H] Compound binding in nM (N) | References | Reference Ki (nM) |
|---|---|---|---|---|
| CB1 (rat brain) | [$^3$H]CP55940 | 1 nM | WIN55212-3 | 18.5 ± 3.0 |
| CB2 | [$^3$H]CP55940 | 2 nM | WIN55212-3 | 9.4 ± 2.6 |
| | | | CP55940 | 4.95 ± 0.55 |

Cannabinoid Binding Buffer: 50 mM Tris HCl, 5 mM MgCl$_2$, 1 mM EDTA, 1 mg/ml BSA, pH 7.4, RT
Cannabinoid Wash Buffer: cannabinoid binding buffer + 1 mg/ml BSA, pH 7.4, cold

TABLE C

GABA receptors From PDSP website

| Target | Radioligand | $K_d$ for [$^3$H] Compound binding in nM (N) | References | Reference $K_i$ (nM) |
|---|---|---|---|---|
| GABA/PBR (rat brain) | [$^3$H]PK11195 | 1 | PK11195 Ro5-4864 | 27.6 ± 2.3 |
| GABAA (rat brain) | [$^3$H]Muscimol | 5.0 | GABA | 241 ± 26 |
| GABAA/BZP (rat brain) | [$^3$H]Flunitrazepam | 0.5 | Diazepam Clonazepam | 1.50 ± 0.08 |

GABA/PBR binding buffer: 50 mM Tris Acetate, pH 7.4, RT
Benzodiazepine (BZP) binding buffer: 50 mM Tris HCl, 2.5 mM CaCl$_2$, pH 7.4, RT
Standard wash buffer: 50 mM Tris HCl, pH 7.4, cold "Saturation binding assays are usually performed immediately after the membrane fraction is obtained and protein concentration is determined (see above section for membrane preparations) to measure receptor expression level ($B_{max}$) and binding affinity ($K_d$) of a selected radioligand. Saturation binding assays are carried out in 96-well plates in a final volume of 125 μl per well. In brief, 25 μl of radioligand is added to each well of a 96-well plate, followed by addition of 25 μl binding buffer (for total binding) or 25 μl reference compound at final concentration of 10 μM (for nonspecific binding). The reaction starts upon addition of 75 μl of fresh membrane protein (typically 25 to 50 μg per well) and the reaction is usually incubated in the dark at room temperature for 90 min. The reaction is stopped by vacuum filtration onto cold 0.3% polyethyleneimine (PEI) soaked 96-well filter mats using a 96-well FILTERMATE harvester, followed by three washes with cold wash buffers . . . . Scintillation cocktail is then melted onto the microwave-dried filters on a hot plate and radioactivity is counted in a MICROBETA counter. IC$_{50}$ values are calculated and converted to $K_i$ values by standard methods (Cheng and Prusoff, 1973)."

Results obtained for effects of compounds derived from Formula (VI) at cannabinoid (CB1) receptors, delta opiate receptors and GABA-A receptors are shown in Table 2.

TABLE 2

Radioligand Displacement Studies: Binding Constants
($K_i$ in μM) for DCUKA, BCUKA, and DCUK-OEt

| Compound | Delta Opiate Receptor | CB1 Receptor | GABAsite, GABA-A Receptor | BDZsite, GABA-A Receptor |
|---|---|---|---|---|
| DCUKA | 4.5 ± 0.73 | 11.0 ± 2.7 | 6.6 ± 1.8 | >10 |
| BCUKA | 1.7 ± 0.41 | N.D. | N.D. | 0.63 ± 0.04 |
| DCUK-OEt | >10 | 7.4 ± 2.4 | 1.7 ± 0.3 | N.D. |

N.D. = not determined

Table 3 lists receptors, ion channels and transporters that were found to have low or no affinity (Ki>10 μM) for DCUKA, BCUKA, and DCUK-OEt.

TABLE 3

Lack of Affinity ($K_i$ > 10 μM) for DCUKA and BCUKA and DCUK-OEt across 26 Receptor/Transporter/Channel Proteins

| Serotonin Rs | Dopamine Rs |
|---|---|
| 5-HT1A | D1 |
| 5-HT1B | D2 |
| 5-HT2A | |
| 5-HT2B | Opiate Rs |
| 5-HT3 | μ |
| | κ |
| Adrenergic Rs (alpha adrenergic) | Prostaglandin Rs |
| α2β2 | EP2 |
| α2β4 | Muscarinic Cholinergic Rs |
| α3β2 | M1 |
| α3β4 | M2 |
| α4β2 | Metabotropic Glutamate Rs |
| α4β2 | mGluR5 |
| Adrenergic Rs (beta adrenergic) | Ionotropic glutamate Rs |
| β1 | NMDA channel binding site |
| β2 | Kainate |
| Voltage sensitive Ca** channel (L-type) | Serotonin Transporter |
| CaV1.2 | Vasopressin |
| | V1A |

Example 3: Effect of DCUKA, BCUKA and DCUK-OEt on Delta Opiate Receptor or Cannabinoid CB1 Receptor Function This example illustrates the effect of DCUK compounds on cyclic AMP production in cells (HeLA or HEK293) transfected with the cannabinoid CB1 receptor or the delta opiate receptor, dopamine $D_1$ receptor, and Type 5 adenylyl cyclase or Type 7 adenylyl cyclase.

HeLa cells and HEK293 cells were obtained from American Type Culture Collection (Manassas, Va.). Cells were cultured in flasks (225 cm$^2$) containing 39 ml of MEM containing 10% fetal bovine serum, penicillin (50 μg/ml), streptomycin (50 μl), and neomycin (100 μg/ml). The flasks were maintained in a humidified atmosphere of 95% air and 5% CO$_2$ at 37° C. Transfection was performed by the method of DNA precipitation with calcium phosphate (Chen and Okayama, 1987) 1 day after HeLa cells or HEK293 cells were transferred to small flasks (75 cm$^2$) at the density of approximately 60 to 80% confluence. Plasmid DNA containing adenylyl cyclase (AC) cDNA (11.5 μg), plasmid DNA carrying the human $D_{1A}$ dopamine receptor cDNA or any other receptor plasmid used in this study (3 μg), and pCMS-EGFP (1 μg) were used for each small flask (75 cm$^2$) containing 13 ml of the culture medium. The amount of DNA per flask was adjusted to a total of 26 gig using vector DNA. Transfection efficiency was routinely monitored by observing the expression of enhanced green fluorescent protein by a epifluorescence microscope equipped with a filter set (excitation, 480/40 nm; emission, 535/50 nm) and a dichroic mirror (T89002bs; Chroma Technology, Rockingham, Vt.). After transfection, cells were harvested and transferred into 24-well culture plates. The transfected cells were cultured for 1 to 2 days before cyclic AMP (cAMP) accumulation experiments were carried out.

The drugs used for the pharmacological treatment were prepared as stock solution. DCUK-OEt, DCUKA and BCUKA were dissolved in dimethyl sulfoxide (DSMO, 10 mM). $D_{1A}$ receptor agonist, dopamine (DA, Sigma) was dissolved in 0.9% Na$_2$S$_2$O$_5$, 1 mM HCl (10 mM); delta opiate receptor (DOR) agonist, DPDPE (Sigma) was dissolved in 1 M acetic acid (1 mM); DOR antagonist Naltrindole (Sigma) was dissolved in H$_2$O (10 mM).

The activity of AC in the transfected cells was assessed by the cAMP accumulation assay as described previously (Kou and Yoshimura, 2007). Briefly, after labeling the intracellular ATP pool with 3.0 μCi/ml of [2,8-$^3$H]adenine, cells were incubated in DMEM (0.5 ml/well) without phenol red, buffered to pH 7.1 with 20 mM 4-(2-hydroxyethyl)-1-piperazineethanesulfonic acid (HEPES) for 30 minutes at 37° C.

To determine the effect of the DCUK-OEt on CB$_1$R or DCUKA and BCUKA on DOR, the cells were treated with the phosphodiesterase inhibitor, IBMX (500 μM) for 10 minutes at 37° C., followed by the addition of DIA receptor agonist, DA (1 μM or 10 μM), in the presence of the appropriate receptor agonist or agonist plus antagonist for 5 minutes. The following agonists and antagonists are used: DCUKA (0.25-20 μM); DCUK-OEt (10 μM); BCUKA (5, 10, 20 μM); CB1 receptor agonist, ACEA (10 μM); CB1 receptor antagonist, AM251 (10 μM); DOR agonist, DPDPE (1 μM); DOR antagonist Naltrindole (10 μM).

The reaction was terminated by adding 50 μl of 100% (w/v) trichloroacetic acid. Cells were exposed to the same amount (10 μl) of DMSO regardless of the DCUKA analog employed. This amount of DMSO did not have any significant effect on the cAMP accumulation (Kou and Yoshimura, 2007). ATP and cAMP contents of each well were separated through DOWEX 50 and neutral alumina columns as described previously (Salomon et al., 1974) and quantified by liquid scintillation spectrometry. [α-$^{32}$P]ATP and [8-$^{14}$C] cAMP were added as internal standards to monitor the recovery of ATP and cAMP through column chromatography. Conversion of [$^3$H] ATP into [$^3$H]cAMP was calculated as follows: [$^3$H]cAMP (%)=[$^3$H]cAMP (cpm)/([$^3$H]ATP (cpm)+[$^3$H]cAMP (cpm))–100. To obtain cAMP accumulation during the 1-minute DA-stimulation period, [$^3$H]cAMP (%) values obtained from cells which underwent only the 10-minute 1BMX±DCUKA incubation period before the addition of trichloroacetic acid, were subtracted from the values obtained from cells which underwent the 1-minute DA-stimulation period. The effect of DCUK-OEt, DCUKA or BCUKA was calculated as the percent change of cAMP accumulation in the presence of DCUK-OEt or BCUKA over that in its absence. The experiments were carried out in triplicate.

In these experiments, the agonist activity of DCUKA, BCUKA or DCUK-OEt at cannabinoid CB1 and delta opiate receptors (DOR) is determined by measuring the effect of DCUKA, BCUKA or DCUK-OEt, in the presence of dopamine (acting at the D1 receptor), on modulation of adenylyl cyclase (AC) activity, which produces changes in cyclic AMP (cAMP) levels. Dopamine stimulates the activity of Type 5 and Type 7 adenylyl cyclases (AC5, AC7). Under conditions of DA-stimulated AC activity, activation of DOR or CB1 receptors by agonists leads to increased activity of AC7 (increased cAMP), but inhibition of activity of AC5 (decreased cAMP).

For the experiments with BCUKA and DCUK-OEt (FIGS. 1 and 2), the value of cAMP accumulation was compared among all treatment groups by one-way ANOVA followed by the Student-Newman-Keuls pairwise comparison method. Significance level was determined as p<0.05.

FIG. 1 demonstrates the effect on cAMP accumulation of the CB1 receptor agonist ACEA and DCUK-OEt in HeLa cells transfected with the AC7 isoform. One way ANOVA revealed an overall significant effect on cAMP accumulation (F (5,18)=3.999, P=0.013). ACEA increased the accumulation of cAMP (P<0.001), and this effect was reversed by AM251, the antagonist of the CB1 receptor (P=0.065 vs DA+ACEA group and P=0.75 vs DA group). Like the CB1 receptor agonist, DCUK-OEt produced a significant increase in cAMP accumulation (P=0.05) in cells which were activated by DA, and the CB1 receptor antagonist AM251 eliminated the DCUK-OEt effect. However, when ACEA and DCUK-OEt were added together, the accumulation of cAMP was noted to be less than in the presence of ACEA above. This result illustrates that DCUK-OEt acts as weak partial agonist at the CB1 cannabinoid receptor.

FIG. 2 illustrates the effect on cAMP accumulation of BCUKA in HEK293 cells transfected with the DA receptor, the delta opiate receptor, and the AC7 isoform. One way ANOVA revealed an overall significant effect on cAMP accumulation (F (6,14)=25.94, P<0.001). BCUKA (10 and 20 µM), in the presence of dopamine, increased cyclic AMP accumulation (P=0.05), and this effect was reversed by the delta opiate receptor antagonist, naltrindole. In addition to the data in the figure, cAMP accumulation in the presence of DA was significantly increased by DPDPE (P<0.001) and this effect was reversed by naltrindole. Taken together, these results illustrate that BCUKA acts as an agonist at the delta opiate receptor.

FIG. 3 illustrates the concentration related inhibitory effect on cAMP accumulation by DCUKA in HeLa cells transfected with delta opiate receptor and the AC5 isoform. Regression analysis determined that the ICso for DCUKA was 3.90±0.47 µM. The effect of DCUKA was reversed by the delta opiate receptor antagonist Naltrindole (not shown). This result illustrates that DCUKA acts as an agonist at the delta opiate receptor.

Example 4: Effect of DCUKA and DCUK-OEt on GABA-A Receptor Function

This example illustrates the effect of DCUKA, DCUK-OEt, DCUK-butanone, DCUK-ethylamide, and DCUK-isopropyl amide on chloride fluxes resulting from activation of GABA-A receptors expressed in *Xenopus* oocytes.

*Xenopus laevis* oocytes were injected with mRNA encoding various GABA-A subunits. Responses to GABA and modulators were recorded 3-5 days later, using two-electrode voltage clamp (Borghese et al., 2014). *Xenopus laevis* frogs were obtained from Nasco (Fort Atkinson, Wis., USA). The complementary DNAs encoding the $GABA_A$ subunits rat α1 and γ2s and human β2 were provided by Dr. M. H. Akabas and Dr. Paul Whiting, respectively. The in vitro transcription of α1, β2, and γ2s subunits was performed using mMessage mMachine® (Life Technologies, Grand Island, N.Y.). After isolation of *Xenopus laevis* oocytes, they were injected with capped complementary RNAs encoding α1, β2, and γ2s subunits in a ratio 2:2:20 ng. The injected oocytes were incubated at 15° C. in sterilized Barth's solution [MBS; composition: 88 mM NaCl, 1 mM KCl, 10 mM HEPES, 0.82 mM $MgSO_4$, 2.4 mM $NaHCO_3$, 0.91 mM $CaCl_2$), and 0.33 mM $Ca(NO_3)_2$, pH 7.5] for 3-5 days before recording. All surgery was performed according to an approved institutional protocol. The responses of $GABA_ARs$ expressed in oocytes were studied through two-electrode voltage clamp (Oocyte Clamp OC-725C, Warner Instruments, Hamden, Conn.), recording through a POWERLAB 4/30 system (ADInstruments, Colorado Springs, Colo.). The oocyte was placed in a chamber perfused with MBS, and voltage-clamped at −70 mV. GABA applications lasted for 20-30 s and the interval between them was 5-15 min. In order to test modulation, the agents were first pre-applied for 1 min and then co-applied with GABA. The application sequence was as follows: Maximal GABA, $EC_{10}$ GABA, $EC_{10}$ GABA, pre-application of the drug immediately followed by a co-application with $EC_{10}$ GABA, $EC_{10}$ GABA.

FIG. 4A compares the effects of DCUKA and DCUK-OEt alone or in the presence of GABA on chloride currents generated by activation of GABA-A receptors. DCUKA and DCUK-OEt had no effect on chloride currents by themselves, but significantly enhanced GABA-induced currents. The results indicate that DCUKA and DCUK-OEt are positive allosteric modulators (PAM) of the actions of GABA.

Figure 4B:
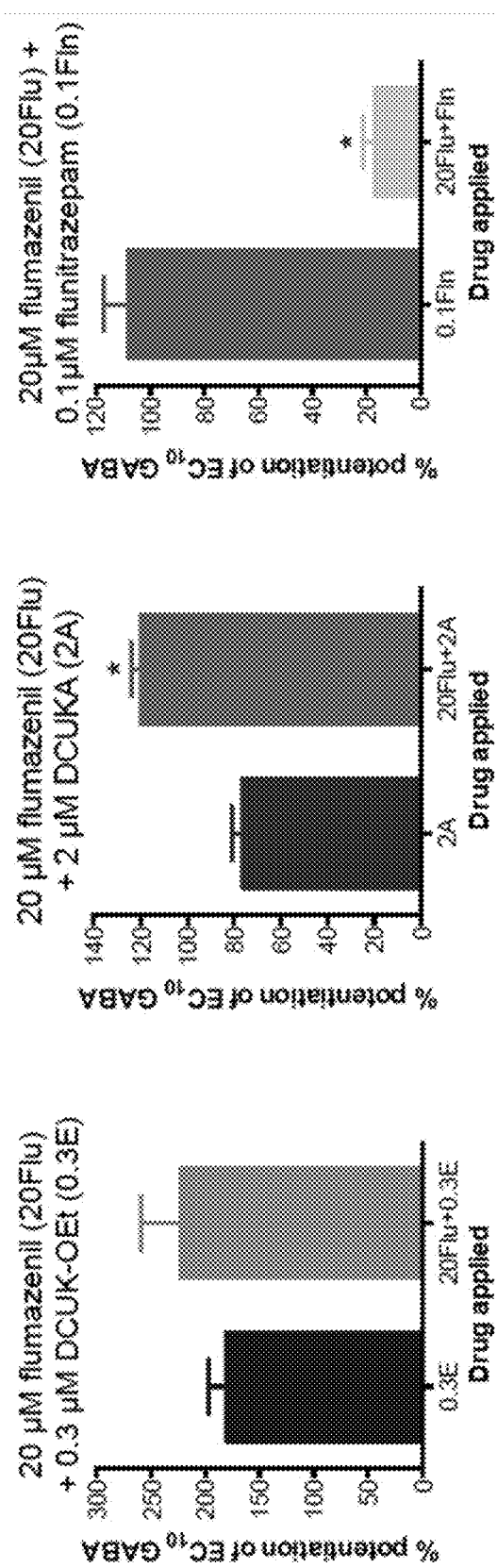
FIG. 4B demonstrates that the DCUK compounds are not acting by binding to the benzodiazepine site on the GABA-A receptor since the specific benzodiazepine antagonist (flumanzenil) had no significant effect on the potentiation of the GABA response either by DCUK-OEt or DCUKA.

FIG. 4B demonstrates that the DCUK compounds are not acting by binding to the benzodiazepine site on the GABA-A receptor since the specific benzodiazepine antagonist had no significant inhibitory effect on the potentiation of the GABA response either by DCUK-OEt or DCUKA.

FIG. 4C illustrates the structure/activity relationship on the efficacy of five DCUK derivatives. This data indicates that DCUK-OEt and DCUK-butanone were most efficacious and suggests that an ester or amide substituent at the 2-position of DCUK is important for the positive allosteric properties of the DCUK compounds.

FIG. 4D provides a graphic representation of the effects of DCUK-OEt on GABA-A receptors having different subunit compositions which are important in the magnitude of the positive allosteric modulation achieved by DCUK-OEt. The tested subunit combinations are listed starting with the most responsive to DCUK-OEt. This rank order, as shown in FIG. 4D does not mirror any currently known positive allosteric modulator of the GABA-A receptor.

Example 5. Effect of DCUKA, BCUKA and DCUK-OEt on Reversal of Neuropathic Pain

This example illustrates the ability of DCUKA, BCUKA and DCUK-OEt to reverse neuropathic pain, measured as mechanical or thermal pain, induced by cisplatin (cancer chemotherapy), Complete Freund's Adjuvant (CFA) (inflammatory pain), or diabetes (streptozotocin-induced pain).

All studies were performed in accordance with the NIH Guide for the Care and Use of Laboratory Animals.

Drugs. For in vivo studies, DCUKA or BCUKA or DCUK-OEt, or gabapentin, were prepared in a 50% gelatin/50% canola oil emulsion (this emulsion was used as vehicle). The gelatin was prepared by adding 0.8 g of gelatin (Knox, Kraft Foods North America, Tarrytown, N.Y.) and 0.06 g tartaric acid (McCormick and Co., Inc., Hunt Valley, Md.) to 30 ml of purified water. The solution was heated at 98° C. for 20 minutes, then cooled to 50° C. Six ml of 95% alcohol and water were added to make 50 ml of gelatin. Various amounts of DCUKA or BCUKA or DCUK-OEt, or gabapentin, were added to 5 ml of canola oil (Safeway Inc., Pleasanton, Calif.) with stirring and sonication (VWR BIO-SONIK IV, 70%) for 5 minutes, and the drug suspensions were then added to 5 ml of gelatin with stirring and sonication. The emulsions were diluted with vehicle as needed and warmed to 37° C. for oral administration to animals. Immediately prior to oral gavage, the emulsion was stirred using a vortex mixer.

Three different agents were used to produce neuropathic pain. Cisplatin (Sigma-Aldrich, St. Louis, Mo.) was dissolved in 0.9% saline solution. Streptozotocin (Sigma-Aldrich) was dissolved in 20 mM sodium citrate buffer, pH=4.5. Complete Freund's Adjuvant (CFA) was obtained from Sigma-Aldrich.

Measurement of Mechanical Hyperalgesia. These studies were performed on male Sprague-Dawley rats (Taconic, Germantown Pa.) at approximately eight weeks of age. Rats were housed in an AAALAC-accredited facility with regulated lighting, temperature and humidity. Pain was tested using an electronic von Frey anesthesiometer (IITC Life Science), Woodland Hills, Calif.). Rats were placed in suspended chambers with a metal mesh floor and were allowed to acclimate for approximately 20 minutes. Mechanical stimuli were applied to the mid-plantar surface of the hind paw(s). Two different methods were used. In the first, a set of von Frey filaments with different strength ranges (g) was used, and filaments of increasing strength were applied to the paw. The force generated with each filament application was displayed on the electronic sensor. Each filament was applied five times, until a paw withdrawal response occurred ("flinch" after filament application). When a filament produced paw withdrawal in four out of five tests, or the maximal stimulus (10% of body weight) was reached, testing was stopped. The average of the four values was used to calculate the paw withdrawal threshold in g. In the second method, a semi-flexible filament was placed against the mid plantar surface of the paw with escalating pressure, until paw withdrawal was observed. The pressure (force in g) at paw withdrawal (paw withdrawal threshold) was recorded by an electronic transducer. Five measurements were taken per test, and the average value was calculated. In both methods, to avoid sensitization, a three-minute interval was imposed between measurements.

Acute Effects of DCUKA, BCUKA, DCUK-OEt and Gabapentin to Reverse Neuropathic Pain (Mechanical Hyperalgesia) Caused by Cisplatin, Complete Freund's Adjuvant (CFA) or Streptozotocin (STZ).

Acute Effect of DCUKA on Cisplatin-Induced Pain: Two methods were used for cisplatin administration. 1) Cisplatin was dissolved in 0.9% saline (1 mg/ml) and injected into the tail vein in a volume of 1.5 or 2.5 ml/kg of body weight. The intravenous injection of cisplatin was followed by an injection of the same amount of saline (Joseph and Levine, 2009). The cisplatin doses were 1.5 or 2.5 mg/kg in individual experiments. 2) Cisplatin was dissolved in 0.9% saline and administered by intraperitoneal injection on days 1, 4, 8 and 12. The cisplatin doses were 2 mg/kg, 1 mg/kg, 2 mg/kg and 2 mg/kg, respectively, for a total dose of 7 mg/kg. A fresh solution of cisplatin was prepared every day before injection, and 0.9% saline (2 ml) was injected subcutaneously after the cisplatin injection (to avoid nephrotoxicity). In all experiments, rats were tested for baseline pain sensitivity (mechanical pain threshold) prior to any cisplatin treatment. The experimental designs for the studies using intravenous injections were as follows: (1) Starting at one hour after cisplatin injection, rats were given vehicle (canola oil/gelatin) orally (by intragastric gavage) twice daily (every 12 hours) for three days (these rats are controls for the study on prevention of cisplatin-induced pain, see below). On the fourth day, rats were again tested for mechanical pain threshold. On the fifth day, rats were given 50 mg/kg DCUKA or vehicle and mechanical pain threshold was tested one hour later. 2) On day 4 after cisplatin treatment, rats were given various doses of DCUKA (12.5, 25, 50, or 75 mg/kg), or vehicle, by intragastric gavage, and mechanical pain threshold was tested one hour later. 3) On day 6 after cisplatin treatment, the mechanical pain threshold was measured, and rats were given 50 mg/kg DCUKA, or vehicle, orally. The mechanical pain threshold was tested one hour later. 4) On day 6 after cisplatin treatment, rats were given various doses of DCUKA (25, 50 or 75 mg/kg) or vehicle, and one hour later, mechanical pain threshold was measured. The experimental design for experiments in which cisplatin was administered intraperitoneally were as follows: on day 14, following the cisplatin treatments (days 1, 4, 8, 12), mechanical pain threshold was tested. Rats were then given 50 mg/kg DCUKA, or vehicle, orally and the mechanical pain threshold was measured one hour later. Data are reported as the ratio of the mechanical pain threshold measured after DCUKA treatment to the baseline pre-cisplatin mechanical pain threshold (measured on the same paw).

Data Analysis of Cisplatin Experiments: Acute Effect of DCUKA and Meta-Analysis: Depending on the experimental design, analysis consisted of either 1-way ANOVA with repeated measures or 2-way ANOVA with repeated measures (Proc Mixed, SAS v9.3, Cary, N.C.). Treatment and time are the main fixed independent effects tested. In one experiment treatment, time and the interaction between the two were assessed. The animal identification number was used as a repeated measure as there are multiple measurements on one animal, including pre and post treatment and left and right paw. All models were tested for equal variances among treatment groups (Barlett's test for homogeneity of variances) and normality (Kolmogorov-Smirnov goodness of fit test). If the data did not pass these assumptions, we adjusted accordingly in the mixed model. Some analyses used Fisher's LSD post hoc tests to compare statistical significance (p-value<0.05) between the different treatment doses and all analyses used Fisher's LSD post hoc tests to compare statistical significance between treatment group and the baseline value.

Experiments were included in the meta-analysis (van Houwelingen et al., 2001) if they met the following requirements: 1. Mechanical pain was measured using a von Frey test, 2. Cisplatin treatment successfully induced pain (25% decrease of mechanical pain threshold) and 3. Mechanical pain was measured within 90 minutes after DCUKA administration. A mixed-model using DCUKA dose as a fixed independent variable with 5 different class levels, study identification as both a random and a repeated measure and rat identification as a random effect was used to determine the overall effectiveness of DCUKA on neuropathic pain (Proc Mixed, SAS v9.3, Cory, N.C.). Fisher's LSD post-hoc tests were used for pairwise comparisons of the DCUKA doses.

Comparison of the Effects of DCUKA, BCUKA and Gabapentin on Cisplatin-Induced Pain. Cisplatin was administered intraperitoneally on days 1 (2 mg/kg), 4 (1 mg/kg), 8 (2 mg/kg) and 12 (2 mg/kg) (7 mg/kg total dose). Cisplatin was prepared daily and 2 ml of 0.9% saline was administered subcutaneously after each cisplatin injection. On day 14, the mechanical pain threshold was measured, and rats received vehicle (canola oil/gelatin), DCUKA (50 mg/kg), BCUKA (50 mg/kg) or gabapentin (30 mg/kg, a dose equimolar to DCUKA and BCUKA). One and two hours later, the mechanical pain threshold was again tested. Data are reported as the ratio of the mechanical pain threshold measured after DCUKA, BCUKA or gabapentin treatment to the baseline mechanical pain threshold (measured on the same paw). Statistical analysis was a 2-way ANOVA with repeated measures (Proc Mixed, SAS v9.3). Treatment and time were the main fixed independent effects, and the interaction was also tested. The animal identification number was used as a repeated measure. Fisher's LSD post hoc tests were used to compare significance (p<0.05) between the different times within treatment groups.

Acute Effect of DCUKA on Compete Freund's Adjuvant (CFA)-Induced Neuropathic Pain. After measurement of the baseline paw withdrawal threshold, CFA (0.1 ml) was administered subcutaneously into the plantar surface of the left hind paw of the rat under light isoflurane anesthesia (5% for induction and 2% for maintenance). Rats were left in their home cage for 48 hours. Paper bedding was used to avoid pressure neuropathies caused by hard bedding. At 48 or 60 hours after CFA injection, rats were given vehicle (canola oil/gelatin) orally, or various doses of DCUKA orally, by intragastric gavage, and the mechanical pain threshold was determined one hour later. Data are presented as the ratio of the mechanical pain threshold measured after DCUKA treatment to the baseline mechanical pain threshold.

Data Analysis of CFA Experiments: Acute Effect of 50 mg/kg DCUKA and Meta-Analysis of DCUKA Dose-Response. Each experiment was analyzed with a 1-way ANOVA (Proc Glm or Proc Mixed, SAS v9.3, Cary, N.C.). Treatment group was the fixed independent effect tested. All models were tested for equal variances among treatment groups (Barlett's test for homogeneity of variances) and normality (Kolmogorov-Smirnov goodness of fit test). If the data did not pass these assumptions, a mixed model was used. All analyses used Fisher's LSD post hoc tests to compare statistical significance (p-value<0.05) among the different treatment groups.

Comparison of the Effect of DCUKA and BCUKA on CFA-Induced Neuropathic Pain. The baseline mechanical pain threshold was determined, and animals were treated with CFA as described above. At 48 hours after CFA treatment, rats were given vehicle (canola oil/gelatin) (n=17), 50 mg/kg DCUKA (n=17) or 50 mg/kg BCUKA (n=6). The mechanical pain threshold was tested one hour later, and data are reported as the ratio of the pain threshold after vehicle, DCUKA or BCUKA treatment to the baseline pain threshold, measured on the same paw. A one-way ANOVA followed by Fisher's LSD post hoc test was used to determine statistical significance (p<0.05).

Acute Effect of DCUKA on Streptozotocin (STZ)-Induced Neuropathic Pain (Model of Diabetic Neuropathic Pain). After measurement of the baseline paw withdrawal threshold, baseline body weight and blood glucose concentrations were determined (blood glucose measured on tail blood, using the ASCENSIA CONTOUR Blood Glucose Monitoring System, Bayer, Pittsburgh, Pa.). Rats were fasted overnight and injected intraperitoneally with vehicle (20 mM sodium citrate, pH 4.5, Sigma-Aldrich), or 50 mg/kg STZ in vehicle. The STZ solution was prepared each day and used within 10 minutes. Food was given to the rats 30 minutes after STZ treatment. Three days after STZ treatment, blood glucose levels were again measured, and rats with a blood glucose level above 350 mg/dl were considered "diabetic". If the blood glucose level was below 350 mg/dl, the rat was given a second dose of STZ (45 mg/kg), using the same procedure. Fourteen days after the first STZ treatment, rats were given vehicle (canola oil/gelatin) or various doses of DCUKA orally, and the mechanical pain threshold was tested at various times after these treatments. Data are presented as the ratio of the mechanical pain threshold following DCUKA treatment to the baseline mechanical pain threshold (measured on the same paw).

Individual Experimental Analysis. Data points were considered as outliers and removed from the dataset if the ratio of the mechanical pain threshold to baseline was outside the corresponding treatment group mean±2 standard deviations. Each experiment was analyzed with a 1-way ANOVA (Proc Glm or Proc Mixed, SAS v9.3, Cary, N.C.). Treatment group was the fixed independent effect tested. All models were tested for equal variances among treatment groups (Barlett's test for homogeneity of variances) and normality (Kolmogorov-Smirnov goodness of fit test). If the data did not pass these assumptions, a mixed model was used. All analyses used Fisher's LSD post hoc tests to compare statistical significance (p-value<0.05) between the different treatments.

Figure 5:
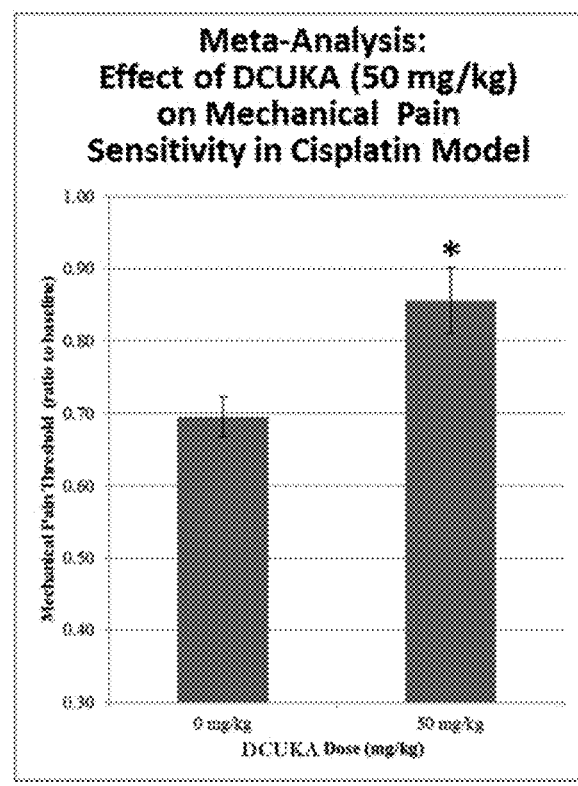
FIG. 5 graphically illustrates the reversal of cisplatin-induced neuropathic pain by DCUKA (50 mg/kg). In rats treated with the cancer chemotherapy agent, cisplatin, the cisplatin treatment reduces the mechanical pain threshold and DCUKA treatment reverses this effect and increases the mechanical pain threshold to control levels. The data show the ratio of the mechanical pain threshold after cisplatin or cisplatin plus DCUKA treatment to the pre-cisplatin treatment mechanical pain threshold. Combined analysis of the effect of 50 mg/kg DCUKA on mechanical pain threshold in a Cisplatin-induced pain model. Treatment means+/−1 SEM plotted. *P-value<0.0001 compared to control (0 mg/kg DCUKA).

FIG. 5 illustrates that DCUKA (50 mg/kg) treatment reverses neuropathic pain caused by treatment of rats with the cancer chemotherapeutic agent, cisplatin. Combined results from six experiments are shown. In all experiments, rats were tested for baseline mechanical pain threshold prior to cisplatin treatment. Following cisplatin treatments described earlier, rats were given DCUKA, and one hour later, the mechanical pain threshold was again determined. The results show the ratio of the mechanical pain threshold measured at one hour after vehicle or DCUKA administration compared to the baseline (pre-cisplatin treatment) mechanical pain threshold.

Figure 6:
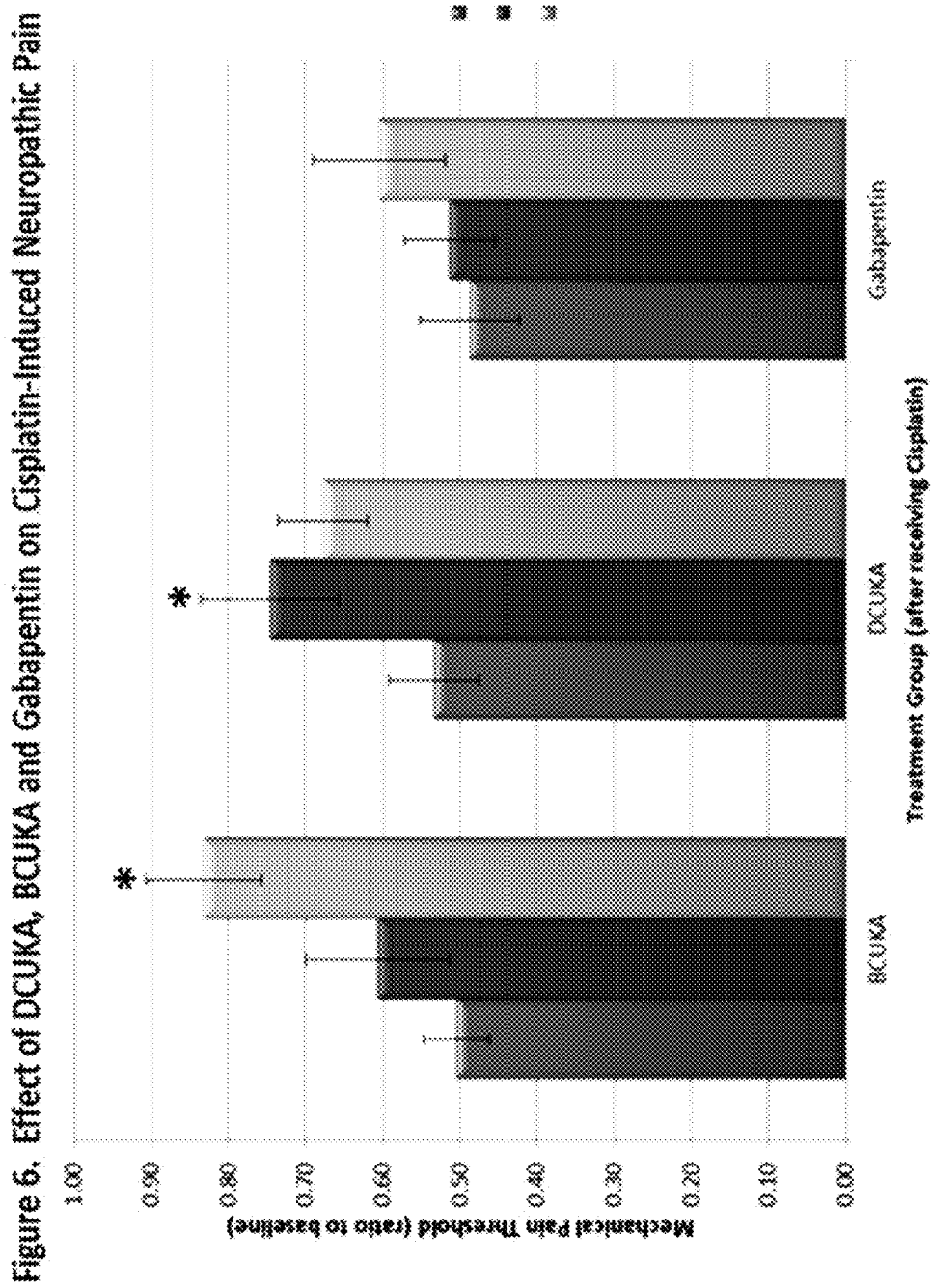
FIG. 6 graphically illustrates a comparison of the effects of equimolar doses of DCUKA, BCUKA and gabapentin to reverse cisplatin-induced neuropathic pain, measured by changes in the mechanical pain threshold. Mechanical pain threshold for each animal is represented by the ratio to baseline. The mean mechanical pain threshold ±1 standard error is plotted for each treatment group and time. *p<0.05 compared to the corresponding pre-treatment group.

FIG. 6 graphically compares the effect of DCUKA (50 mg/kg), BCUKA (50 mg/kg) and gabapentin (Neurontin, 30 mg/kg) on neuropathic pain induced by the chemotherapeutic agent, cisplatin. Rats were tested for baseline mechanical pain threshold prior to cisplatin treatment, and were treated with cisplatin as described earlier. Following cisplatin treatment the mechanical pain threshold was measured, and rats were given oral doses of vehicle, DCUKA, BCUKA, or gabapentin. The mechanical pain threshold was again measured at 1 and 2 hours after these treatments. Data are the ratio of the mechanical pain threshold measured prior to DCUKA, BCUKA or gabapentin administration, and 1 and 2 hours later. Cisplatin treatment alone ("pretreatment") significantly reduced the mechanical pain threshold, compared to baseline, and DCUKA and BCUKA significantly reversed the drop in mechanical pain threshold. Gabapentin, at a dose equimolar to DCUKA and BCUKA, did not significantly reverse the cisplatin-induced decrease in the mechanical pain threshold.

Figure 7:
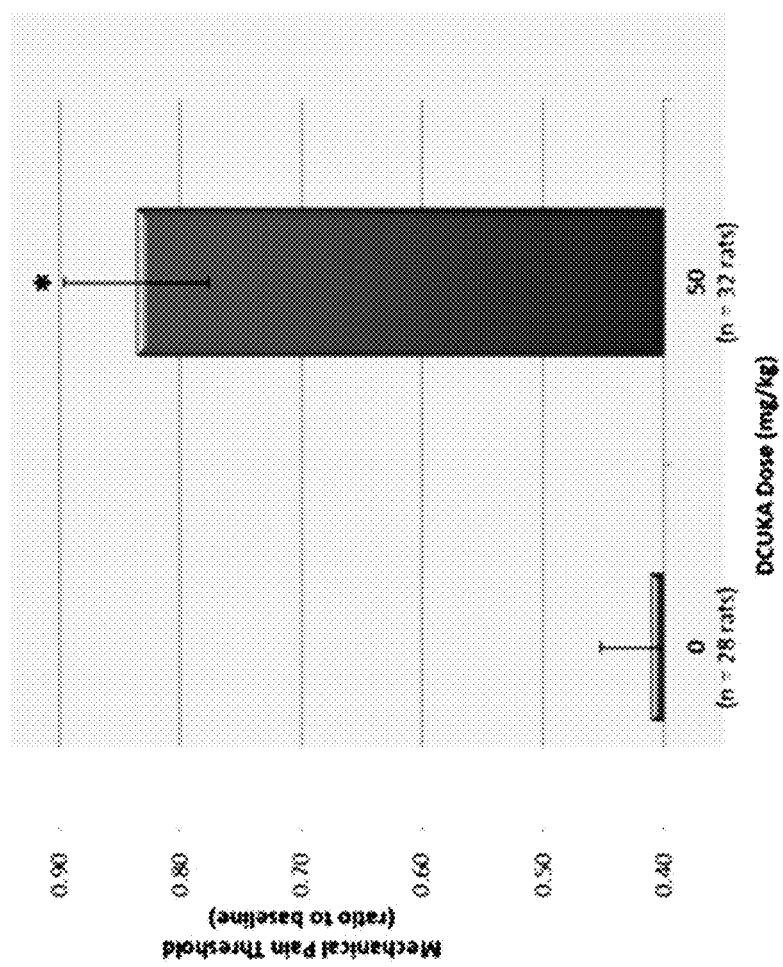
FIG. 7 graphically illustrates the reversal by DCUKA (50 mg/kg) of neuropathic pain induced by treatment of rats with Complete Freund's Adjuvant (CFA). CFA treatment induces inflammation and reduces the mechanical pain threshold. DCUKA treatment reverses the drop in the mechanical pain threshold in CFA-treated rats and returns the threshold toward the baseline level. The data show the ratio of the mechanical pain threshold after CFA or CFA plus DCUKA treatment to the mechanical pain threshold prior to CFA treatment. A post-hoc Fisher's LSD t-test for pairwise comparisons showed a significant (*) difference between 50 mg/kg DCUKA and 0 mg/kg DCUKA (p-value<0.0001).

FIG. 7 graphically illustrates that DCUKA reverses the neuropathic pain induced by treatment of rats with Complete Freund's Adjuvant (CFA) to produce an inflammatory response. Data are combined from three experiments. In each experiment, the baseline mechanical pain threshold (force, in g, causing paw withdrawal) was first measured using an electronic von Frey anesthesiometer. Rats were then injected with 0.1 ml complete Freund's Adjuvant (CFA) into the plantar surface of the left hind paw. Forty-eight to 60 hours later, when CFA-induced pain had developed, rats received oral administration of vehicle (gelatin/canola oil emulsion) or 50 mg/kg DCUKA. One hour later, mechanical pain threshold was again measured. The results show the ratio of mechanical pain threshold measured one hour after vehicle or DCUKA treatment to the baseline mechanical pain threshold. CFA treatment reduced the mechanical pain threshold by approximately 60%, and DCUKA treatment reversed this effect and increased the mechanical pain threshold in the CFA-treated paw to a level not significantly different from the baseline level.

Figure 8:
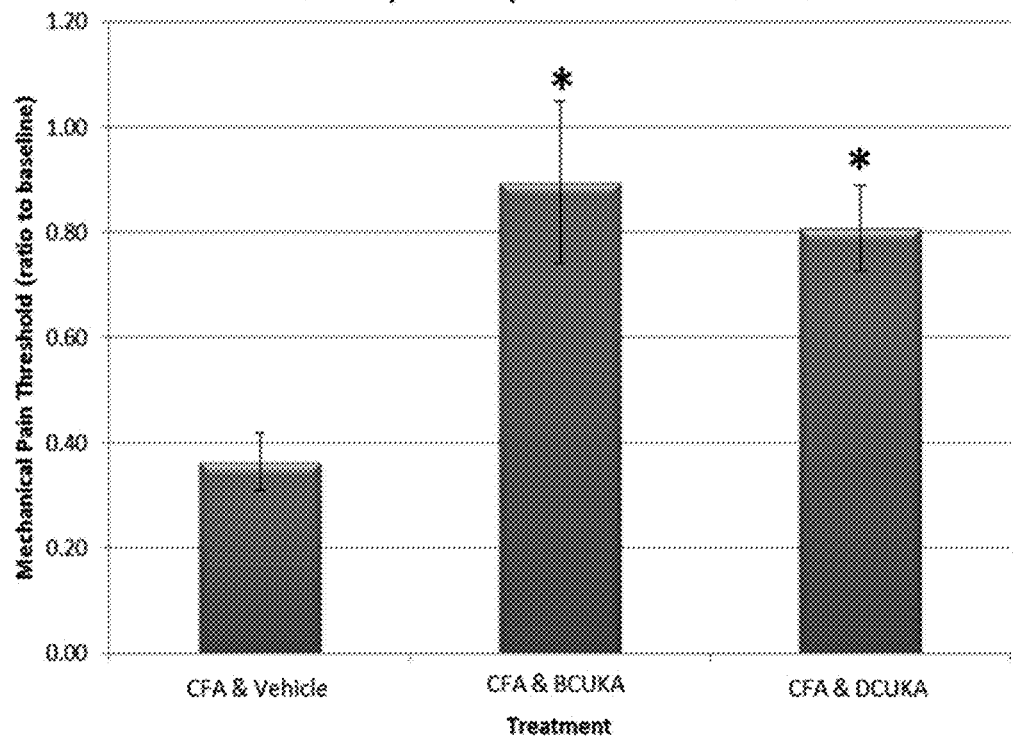
FIG. 8 illustrates a comparison of the effect of DCUKA (50 mg/kg) and BCUKA (50 mg/kg) to reverse neuropathic pain induced by treatment of rats with CFA. The data show the ratio of the mechanical pain threshold after CFA treatment, or CFA plus DCUKA or BCUKA treatment, to the baseline (pre-CFA) mechanical pain threshold. Mechanical pain threshold for each animal is represented by the ration to baseline for the injected paw only. The mean mechanical pain threshold ±1 standard error is plotted for each treatment group. *P<0.05 compared to vehicle.

FIG. 8 graphically illustrates a comparison of the effect of DCUKA (50 mg/kg) and BCUKA (50 mg/kg) to reverse neuropathic pain produced by CFA treatment. Baseline mechanical pain threshold was measured, and rats were treated with CFA as described earlier. Forty-eight hours later, rats were given vehicle (canola oil/gelatin), DCUKA or BCUKA, and one hour later the mechanical pain threshold was measured. CFA treatment reduced the mechanical pain threshold to about 40% of baseline, and treatment with DCUKA (n=17) or BCUKA (n=6) reversed the mechanical pain threshold to a level not significantly different from baseline.

Figure 9:
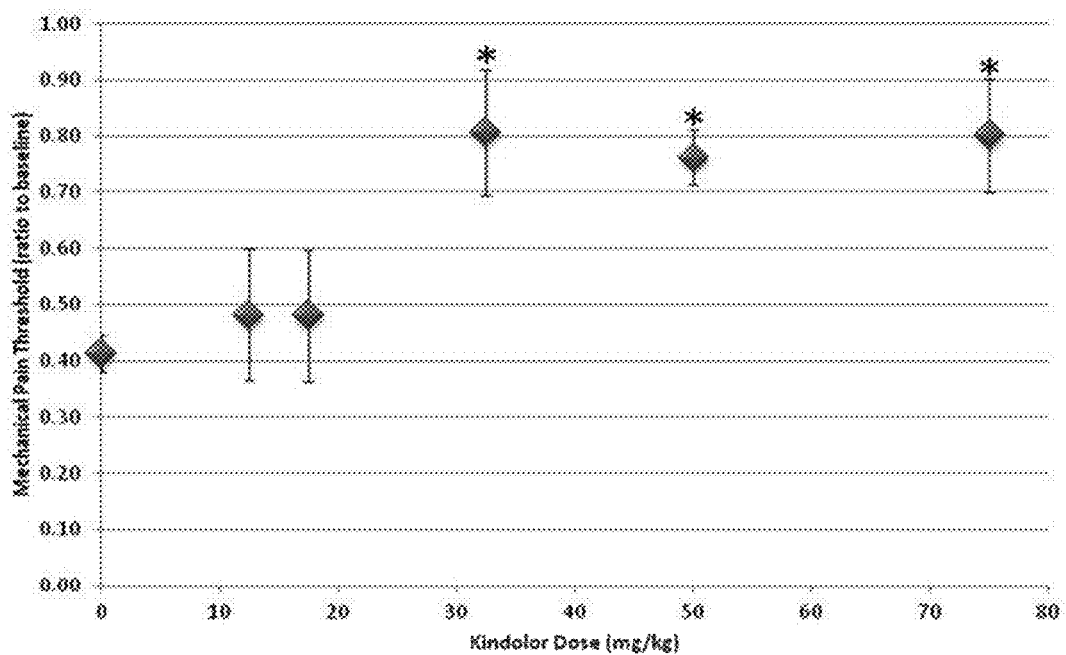
FIG. 9 shows the results of a meta analysis of experiments to determine the dose dependent effect of DCUKA to reverse CFA-induced neuropathic pain. Mechanical pain threshold for each animal is represented by the ratio to baseline for the injected paw only. The mean mechanical pain threshold ±1 standard error is plotted for each treatment group. This is based on treatment means from the 5 studies included in the meta analysis. *P<0.05 compared to the vehicle (0 mg/kg) treatment group.

The dose dependence of the effects of DCUKA on neuropathic pain produced by CFA was determined using a meta-analysis approach. The results are shown in FIG. 9. In all experiments with CFA, the baseline mechanical pain threshold was measured with an electronic von Frey anesthesiometer. CFA was injected into the plantar surface of the left hind paw and, at 48 hours after injection, rats were given oral vehicle (gelatin/canola oil) or DCUKA. The mechanical pain threshold was again measured at 60 min after vehicle or DCUKA administration. For an experiment to be included in the meta-analysis, the requirements were: 1) CFA treatment produced at least a 25% decrease in the mechanical pain threshold; 2) the pain threshold was measured at 60 min after DCUKA or vehicle administration. Five experiments, in which different doses of DCUKA were tested, met these requirements. The mechanical pain threshold, as a ratio to the baseline mechanical pain threshold, is shown as mean±SEM. There was a significant overall effect of DCUKA ($F(5,125)=7.71$, $P<0.0001$). CFA treatment reduced the mechanical pain threshold by approximately 60%, and this effect was significantly reversed by DCUKA doses of 30 mg/kg and higher, i.e., the pain threshold returned to the baseline level.

Figure 10:
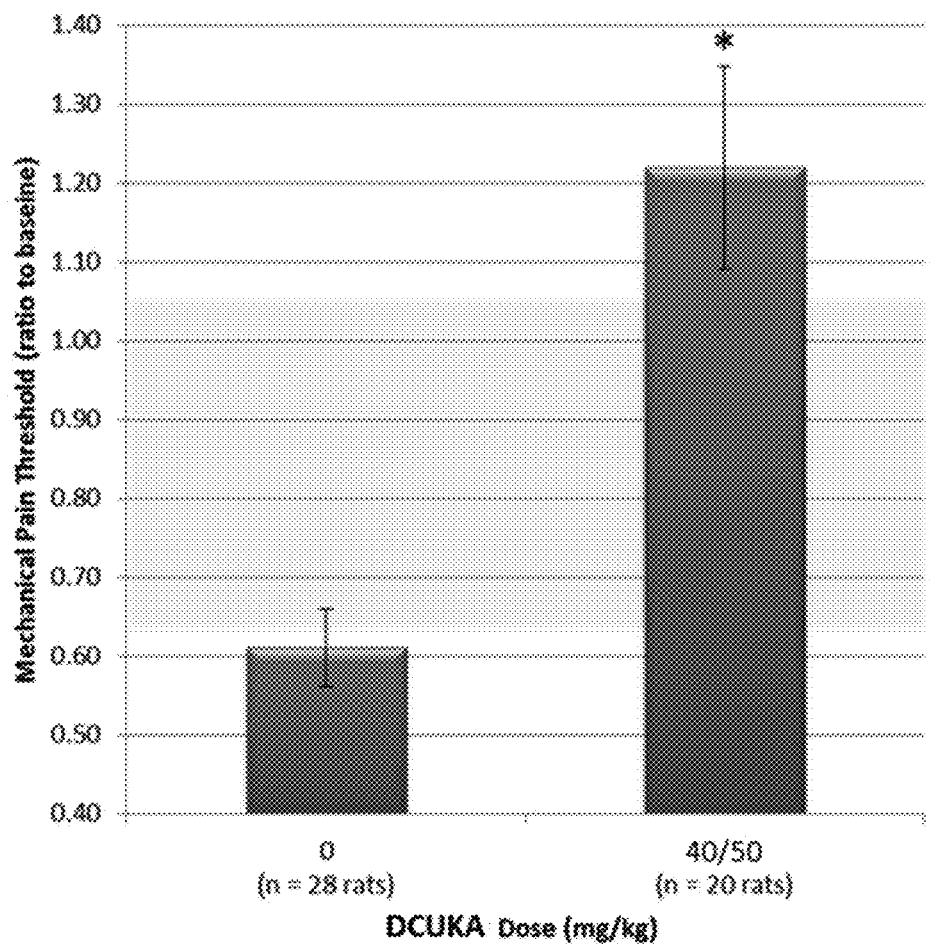
FIG. 10 graphically illustrates the reversal by DCUKA (50 mg/kg) of pain caused by diabetic neuropathy. Rats were treated with streptozotocin (STZ) to induce diabetes, which reduced the mechanical pain threshold in comparison to baseline (pre-STZ treatment). DCUKA treatment reversed the mechanical pain threshold to baseline. The data show the ratio of the mechanical pain threshold after STZ or STZ plus DCUKA treatment to the pre-STZ mechanical pain threshold. A post-hoc Fisher's LSD t-test for pairwise comparisons, showed a significant (*) difference between 50 mg/kg DCUKA and 0 mg/kg DCUKA (difference=0.60, p-value<0.0001).

FIG. 10 illustrates that DCUKA reverses the neuropathic pain that accompanies diabetes. Diabetes is induced in rats by injection of streptozotocin (STZ) as described earlier. Combined data from three experiments are shown. In each experiment, baseline mechanical pain threshold was tested using an electronic von Frey anesthesiometer. Fourteen days after STZ treatment, vehicle (gelatin/canola oil) or 40 or 50 mg/kg DCUKA (these doses did not have significantly different effects) was administered orally and mechanical pain was assessed 90 minutes later. The results show the ratio of the mechanical pain threshold following vehicle/DCUKA treatment to the baseline mechanical pain threshold. STZ reduced the mechanical pain threshold by approximately 40%, and this effect was reversed to the baseline level by DCUKA treatment.

The dose-dependence of the effects of DCUKA on STZ-induced neuropathic pain was determined by a meta-analysis approach. Requirements for an experiment to be included in the meta-analysis were: 1) STZ treatment induced neuropathic pain, as measured by a decrease in mechanical pain threshold of at least 25%; 2) pain was measured 90 minutes after vehicle or DCUKA treatment. Four experiments that met these criteria were included in the meta-analysis.

Figure 11:
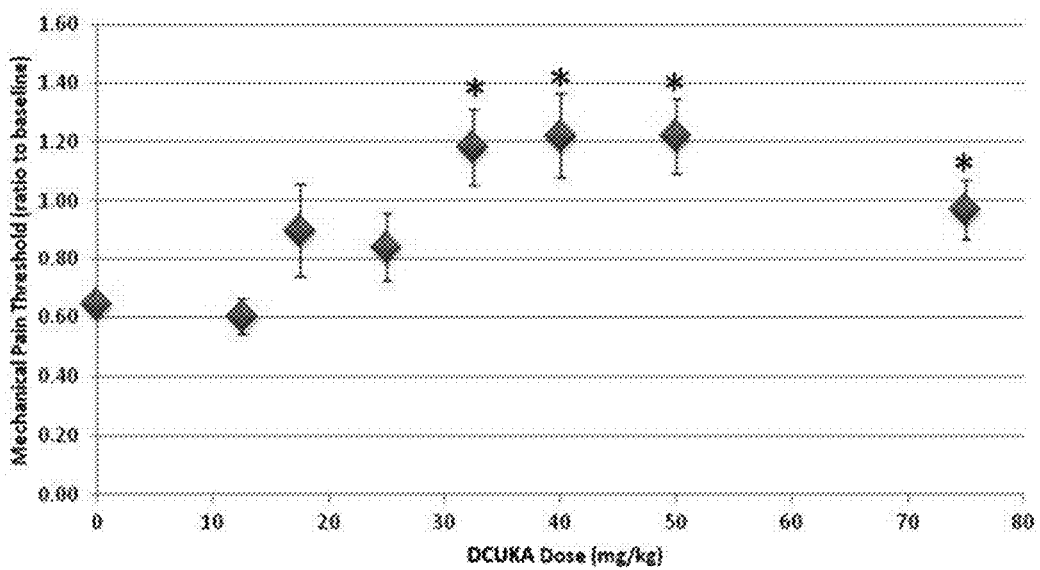
FIG. 11 shows the results of a meta-analysis of experiments to determine the dose-dependent effect of DCUKA to reverse STZ-induced neuropathic pain. Data are the ratio of the mechanical pain threshold measured after DCUKA treatment to the baseline mechanical pain threshold measured on the same paw. *P<0.05 compared to the vehicle treatment group.

FIG. 11 shows the dose-dependence of the effect of DCUKA to reduce STZ-induced neuropathic pain. The data are reported as the ratio of the mechanical pain threshold after vehicle or DCUKA treatment to the baseline pain threshold. There was an overall significant effect of DCUKA on mechanical pain threshold ($F(7, 115)=8.48$, $p<0.0001$). STZ treatment induced approximately a 40% reduction in the pain threshold, and doses of DCUKA of 30 mg/kg and higher reversed the effect of STZ and increased the pain threshold back to the baseline level.

Example 6 Naltrindole Reversal of the Effect of DCUKA on CFA-Induced Neuropathic Pain This example demonstrates that the anti-allodynic response to administration of DCUKA can be reversed by introducing naltrindole (a delta opiate receptor antagonist) to the site of inflammation.

Rats were tested for baseline mechanical pain threshold (von Frey test) and given an intraplantar injection of Complete Freunds Adjuvant (CFA) in the left hind paw. After two days, rats were treated with either vehicle or 50 mg/kg DCUKA, orally, and 45 min after DCUKA/vehicle treatment, rats received either Naltrindole (10 µg per 50 µl per paw) or saline (50 µl per paw) s.c., in the plantar surface of left paw. At 15 minutes after Naltrindole or saline injection, the pain threshold was assessed.

Figure 12:
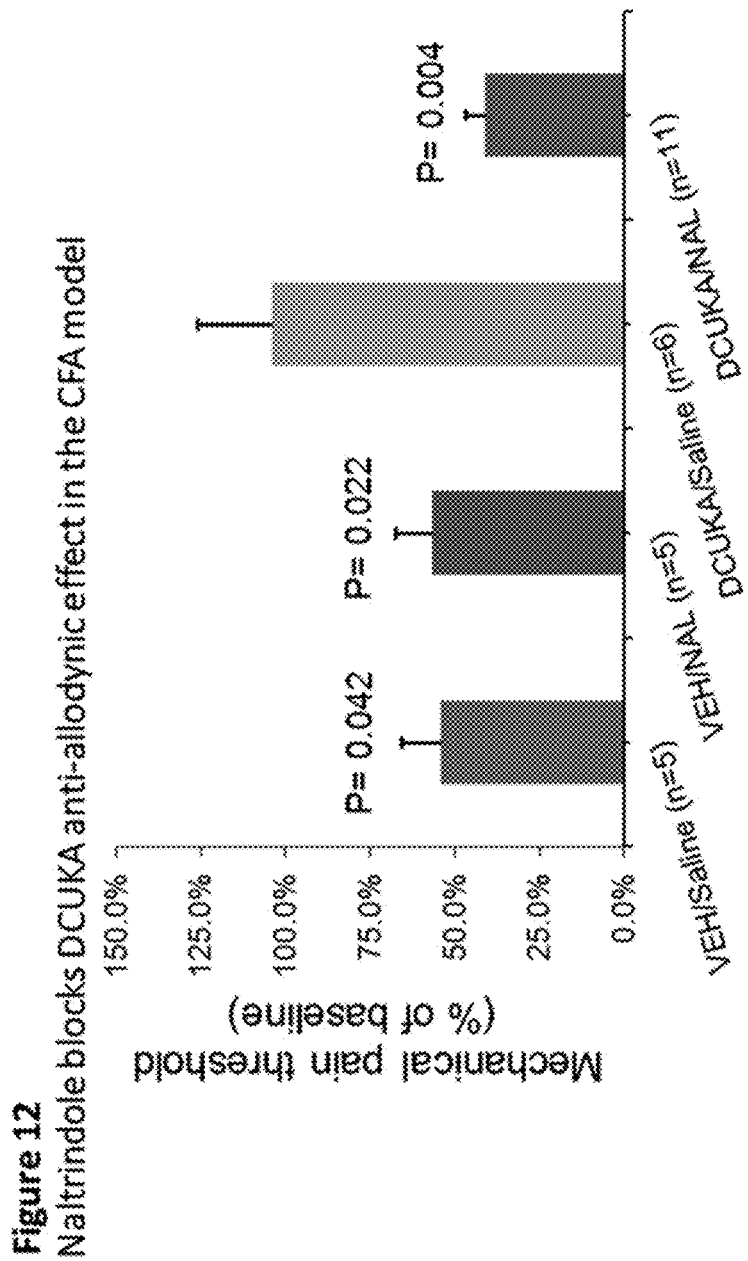
FIG. 12 shows that the ability of DCUKA to reverse CFA-induced neuropathic pain is reversed by the delta opiate receptor antagonist, naltrindole, which is injected into the inflamed paw. Data are presented as mean±SEM percent of baseline paw withdrawal threshold. P-values are compared to the DCUKA/Saline group (one way ANOVA and post hoc Student-Newman-Keuls test). Nal, Naltrindole.

FIG. 12 illustrates that the presence of naltrindole at the site of inflammation reversed the anti-allodynic effect of DCUKA. CFA treatment reduced the mechanical pain threshold by about 50%, and DCUKA/saline increased the pain threshold back to baseline level. In the presence of naltrindole and DCUKA, the allodynic response was no different from that in animals injected with just the vehicle, and naltrindole had no effect on its own. These results underscore the importance of delta opiate receptors in the actions of DCUKA, in vivo, as was indicated by the in vitro binding and functional assays.

Example 7 Prevention of Cisplatin- and CFA-Induced Neuropathic Pain by DCUKA

This example illustrates that treatment of animals with DCUKA following insult, but prior to development of neuropathic pain, can prevent the development of the pain. Rats were treated with cisplatin or CFA, and mechanical pain threshold was measured, as described under Example 5.

Prevention of CFA-Induced Neuropathic Pain by DCUKA. After baseline measurement of the mechanical pain threshold, rats were treated with CFA as described earlier. Following the CFA injection, rats were given vehicle (canola oil/gelatin) (n=7) or 50 mg/kg DCUKA (n=7) orally by intragastric gavage. Rats then received three more treatments with vehicle or DCUKA at 12-hour intervals. At 60 hours after CFA treatment, the mechanical pain threshold was again tested.

Prevention of Cisplatin-Induced Neuropathic Pain by DCUKA. One day after baseline measurement of the mechanical pain threshold, rats were injected i.p. with cisplatin. Cisplatin injections were again given on days 4, 8, and 12. Starting one hour after the first cisplatin injection, rats were given 50 mg/kg DCUKA or vehicle via intragastric gavage twice daily for 14 days. After the last treatment (day 15) the mechanical pain threshold was again tested. The pain threshold was then tested once weekly for 4 weeks, with no further treatments.

Figure 13:
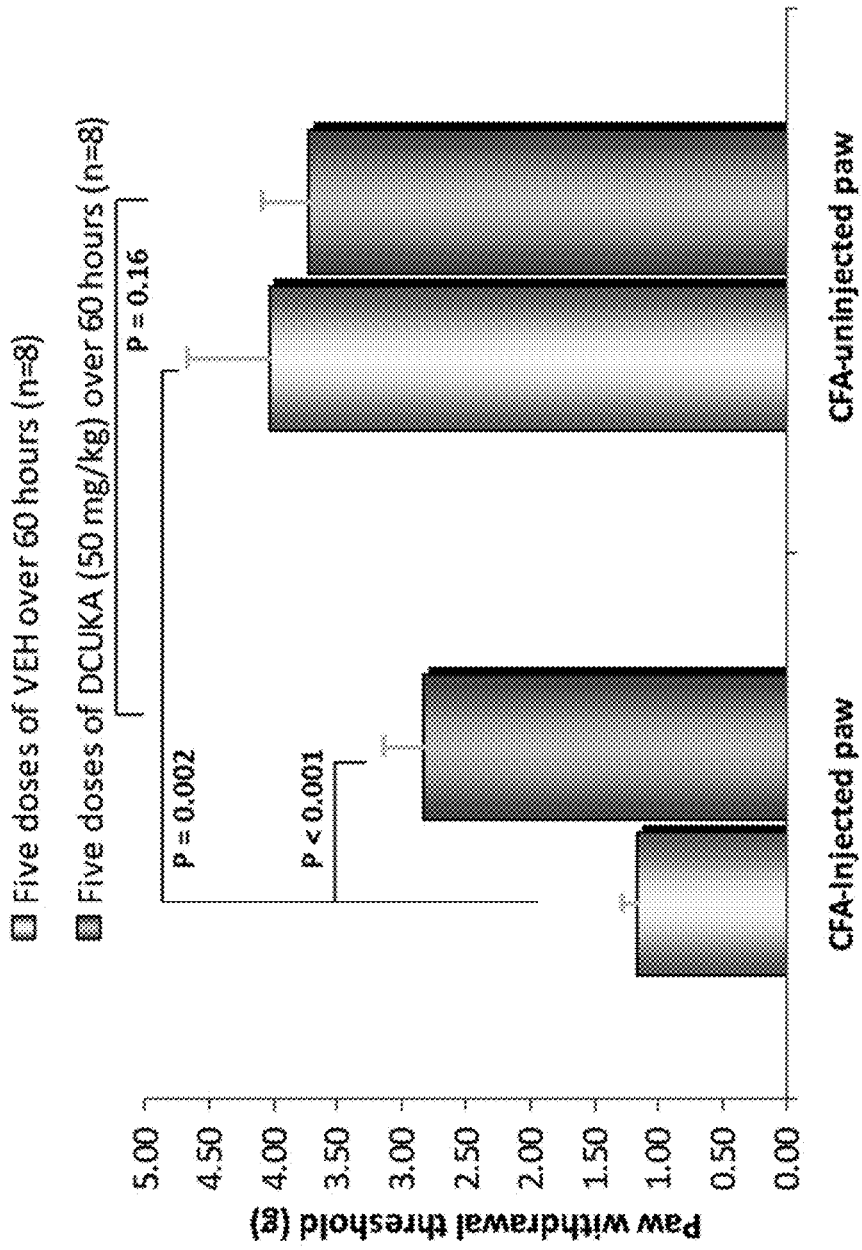
FIG. 13 illustrates graphically that administration of DCUKA following CFA injection prevents the development of CFA-induced neuropathic pain, measured by changes in the mechanical pain threshold. Note: Student's t-test is used to compare the pain threshold between group, and paired t-test is used to compare the pain threshold within group.

FIG. 13 shows that DCUKA can prevent the development of neuropathic pain caused by CFA. Data show the ratio of the mechanical pain threshold at 60 hours after CFA treatment to the pre-CFA baseline mechanical pain threshold. CFA treatment significantly reduced the pain threshold by approximately 70%. However, when animals were given DCUKA daily prior to testing, the threshold was not reduced (P=0.16), and remained close to the baseline pain threshold, i.e., DCUKA has the ability to prevent the development of inflammatory pain, when given after administration of an inflammatory agent.

Figure 14:
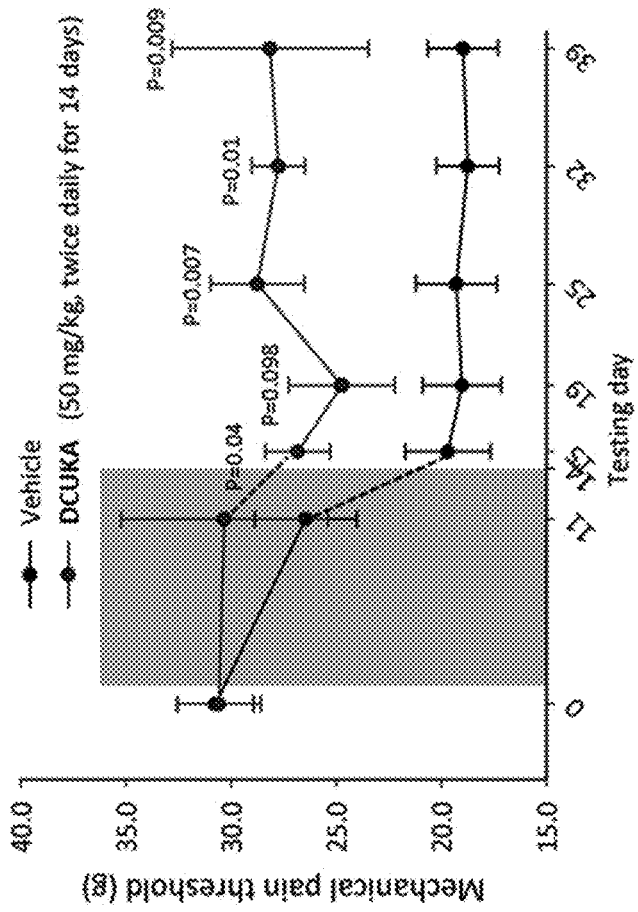
FIG. 14 illustrates graphically that administration of DCUKA simultaneously with the cancer chemotherapy agent cisplatin prevents the development of cisplatin-induced neuropathic pain, measured by changes in the mechanical pain threshold. Two way repeated measure ANOVA revealed a statistically significant difference (P=0.023) between the two treatments, DCUKA and vehicle. The individual p values shown in the graph are for DCUKA versus vehicle and are calculated by the multiple comparison method. There are also significant differences detected in the pain threshold in the cisplatin and vehicle group (day 15, 19, 25, 32) compared to day 0, before cisplatin, but no significant differences in pain threshold between the cisplatin and DCUKA group compared to the Day 0 values (prior to cisplatin injection).

FIG. 14 illustrates that repeated DCUKA treatments during the period between the administration of cisplatin and pain testing, prevented the development of pain in the rat cisplatin-induced neuropathic pain model. Data are presented as mean±SEM of the mechanical pain threshold (paw withdrawal threshold). Injection of Cisplatin resulted in a significant decrease in mechanical pain threshold over days in the rats treated chronically with vehicle. With repeated DCUKA treatments, there was no statistically significant decrease of pain threshold compared to the pre-cisplatin baseline. The results show that DCUKA has the ability to prevent the development of chemotherapy-induced neuropathic pain, when given after the administration of the chemotherapeutic agent.

Example 8 DCUKA and DCUK-OEt Enhance the Effect of Morphine on CFA-Induced Neuropathic Pain Example 8 demonstrates that combining low doses of DCUKA and morphine results in a synergistic effect on reduction of mechanical allodynic and thermal hyperalgesic pain produced by an inflammatory agent.

CFA treatment and measurement of mechanical pain threshold are described under Example 5. In this experiment, mechanical pain threshold was tested at baseline. At 48 hours after CFA treatment, vehicle, DCUKA or morphine, or the combination of DCUKA and morphine, were injected 30 minutes prior to measurement of the mechanical pain threshold.

Thermal Hypersensitivity Test (Radiant Heat Paw Withdrawal Test). Rats were placed in clear plastic chambers on a glass surface and were habituated for 15 minutes before testing. Thermal sensitivity was measured by using paw withdrawal latency to a radiant heat stimulus. A radiant heat source (i.e., infrared) was activated with a timer and focused onto the plantar surface of the left hind paw. A motion detector that halted both lamp and timer when the paw was withdrawn determined paw withdrawal latency. The latencies were measured before and after drug or vehicle administration. A maximum cutoff of 33 seconds was used to prevent tissue damage. In this experiment, rats were injected with DCUK-OEt, immediately followed by morphine at increasing dose ratios, and tested 30 minutes later.

Figure 15:
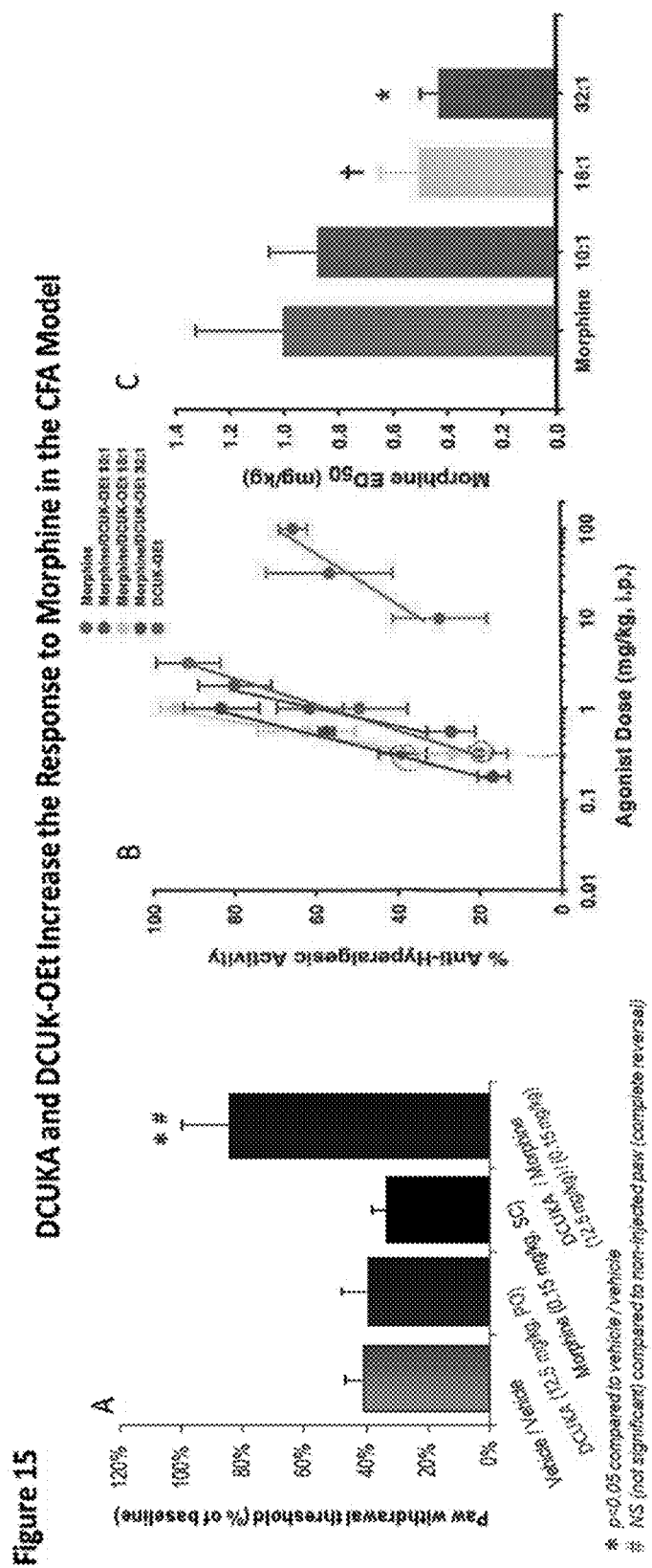
FIG. 15 shows graphically that administration of DCUKA or DCUK-OEt enhances the ability of morphine to reverse CFA-induced neuropathic pain, measured by changes in paw withdrawal threshold in a test of thermal hyperalgesia; DCUKA-OEt significantly decreased the half-maximal effective dose of morphine needed to reverse pain. DCUK-OEt decreased the ED50 for the anti-hyperalgesic actions of morphine at 18:1 (†P<0.05). DCUK-OEt/morphine dose ratios compared to Morphine alone by one-way ANOVA with post-hoc Dunnett's test).

FIG. 15, Panel A, demonstrates that combining doses of DCUKA and morphine, that in themselves, are ineffective in producing analgesia, results in a complete reversal of inflammation-induced chronic pain. FIG. 15, Panels B and C, provides evidence that the combination of DCUK-OEt and morphine provides a supra-additive effect, as compared to either agent given alone. In this case, thermal hyperalgesia produced by CFA treatment was tested. The $ED_{50}$ for the anti-hyperalgesic response to morphine was significantly reduced by administering DCUK-OEt in a dose ratio to morphine of >30:1. For instance, a dose of 0.2 mg/kg morphine produces approximately a 20% antihyperalgesic response. Combined with 6.4 mg of DCUK-OEt, the response is increased to 40%.

Example 9 DCUKA Enhances the Effect of Aspirin on STZ-Induced Neuropathic Pain

Example 9 demonstrates that in another model of chronic pain, the STZ diabetic neuropathy model, DCUKA can synergize with another analgesic (aspirin) to reduce allodynia.

After administration of streptozotocin (STZ) as described in Example 5, rats were tested for allodynia using a von Frey apparatus. Sixty minutes prior to testing, rats were divided into four groups. Group 1 received vehicle; group 2 received DCUKA; group 3 received aspirin; and group 4 received a combination of DCUKA and aspirin.

Figure 16:
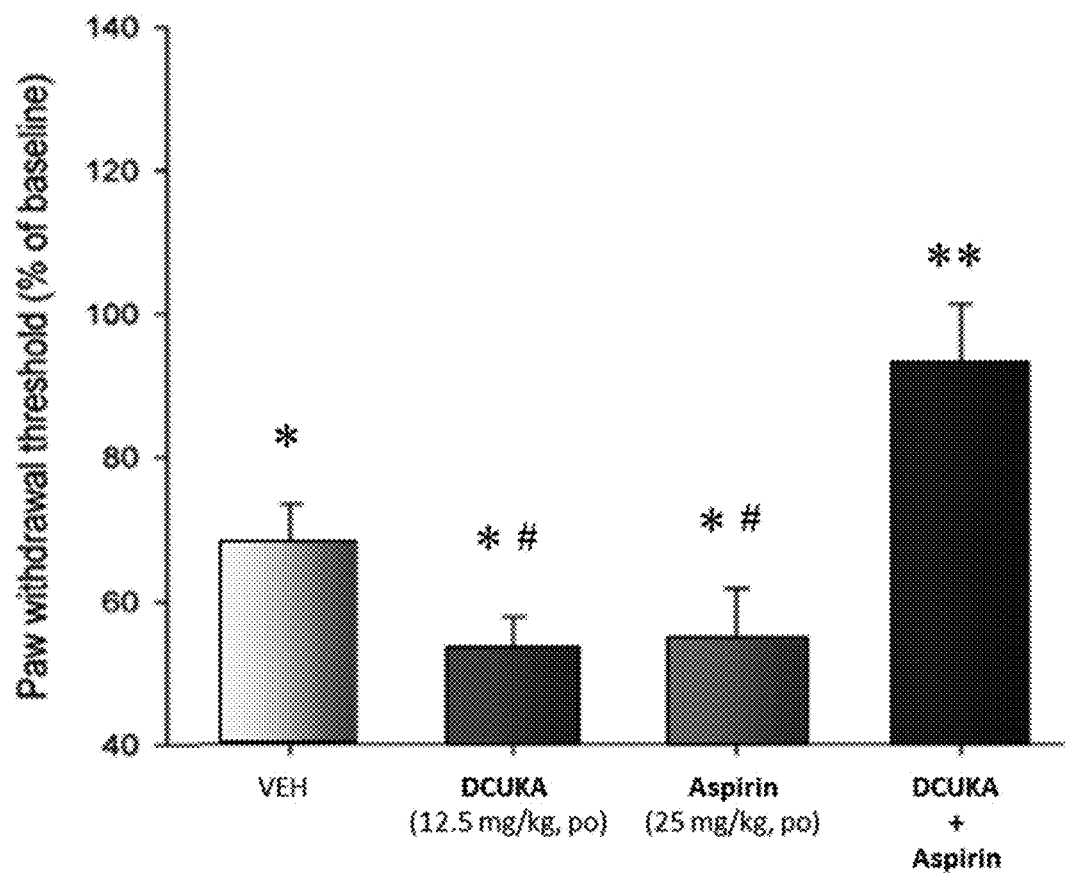
FIG. 16 illustrates that DCUKA enhances the ability of aspirin to reverse STZ-induced neuropathic pain (diabetic neuropathy). *p<0.05 compared to control group (no STZ treatment). #NS compared to vehicle treatment group. **NS compared to no STZ treatment.

FIG. 16 demonstrates that doses of DCUKA (12.5 mg/kg) or aspirin (25 mg/kg) which by themselves do not have any significant effect on allodynia, when combined, completely reverse the hyper-responsiveness, i.e., return the pain threshold to the baseline level.

Example 10 Effect of DCUK-OEt on "Relapse" Alcohol Consumption by Alcohol-Dependent Rats This example illustrates the use of an animal model of alcohol deprivation in alcohol dependent animals to produce relapse drinking, and shows that DCUK-OEt can prevent relapse in those animals.

This model is thoroughly described in a paper by (Spanagel and Holter, 1999). The model consists of a conditioning phase where individually housed male Wistar rats are allowed ad libitum access to food and 0, 5, 10 and 20% alcohol solutions in a four-bottle choice paradigm. The rats are weighed every $3^{rd}$ and $4^{th}$ day and food and fluid consumption is measured. The positions of bottles are changed once a week and after two months of continuous alcohol access, rats are deprived of alcohol for two weeks. After the deprivation phase, all alcohol solutions are presented again for 5 weeks and the procedure is repeated for ~1 year. At this point an alcohol deprivation phase is instituted. Pre-deprivation (baseline) drinking is recorded for 3-4 days and then all alcohol is taken from the animals and they are only given water to drink for two weeks. Following alcohol deprivation, alcohol intake (total grams of ethanol/kg body weight) and water intake (ml/kg body weight) are measured daily. The alcohol preference ratio is calculated as (ethanol consumption [g/kg])/(water consumption [ml/kg]).

For this experiment, animals were divided into groups of 6-8 rats such that the mean baseline total alcohol intake was approximately the same (~2.8 g/kg/day) across all groups. Baseline drinking was monitored followed by 14 days of alcohol deprivation. Each animal then received i.p. injections of DCUK-OEt twice daily at 12 hour intervals starting at 7 PM prior to the reintroduction of ethanol for a total of 3 (20 mg/kg) or 5 injections (75 mg/kg). Acamprosate, an already marketed agent for reducing relapse, was used as a positive control and four doses of 50 mg/kg or 200 mg/kg were injected over a two-day period. Alcohol bottles were re-introduced after the first (acamprosate) or second (DCUK-OEt) injection.

Figure 17:
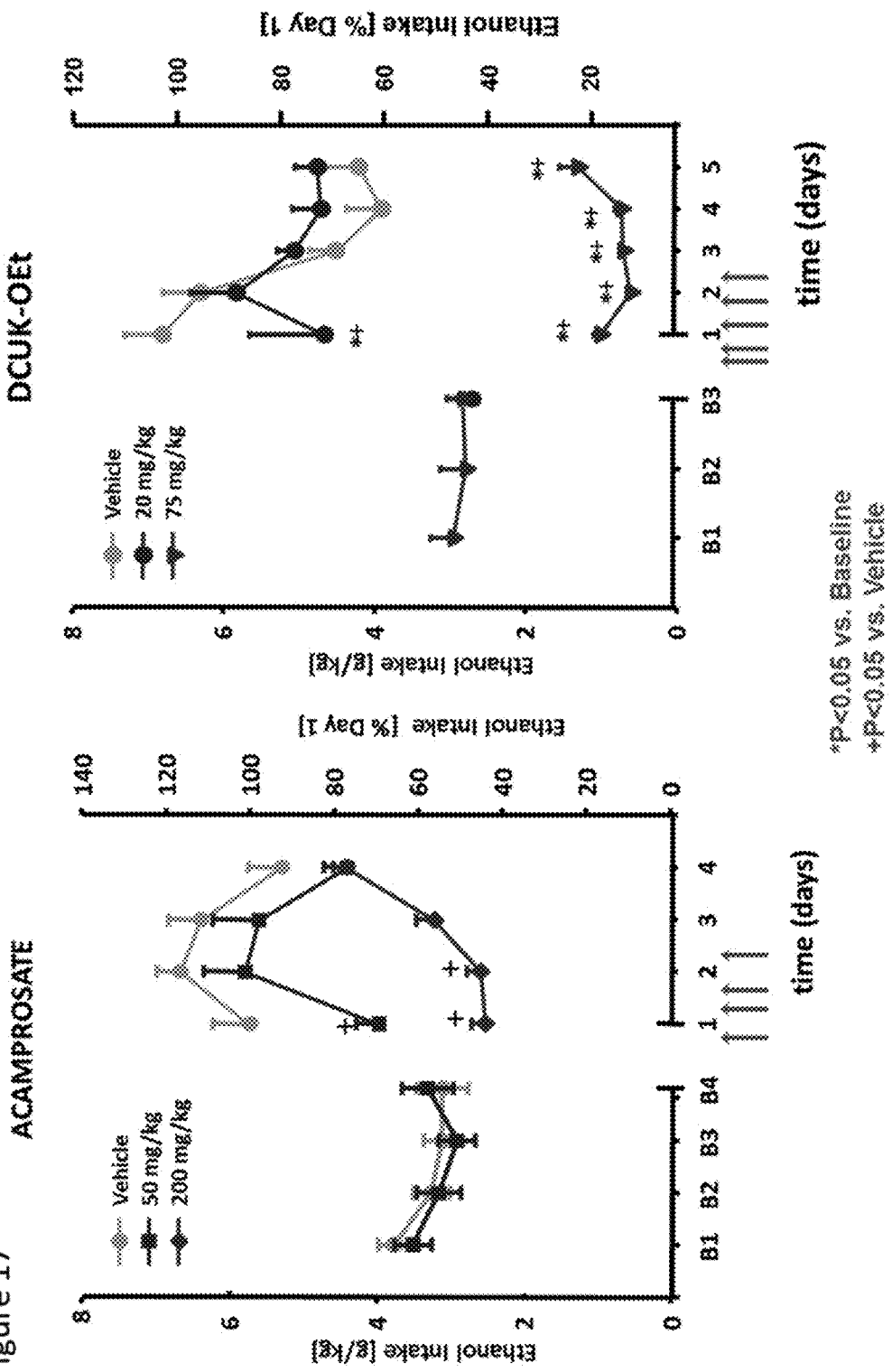
FIG. 17 illustrates the reduction in abstinence-induced alcohol consumption (relapse) by DCUK-OEt in animals made physically dependent on alcohol by long term ethanol consumption.

The results in FIG. 17 demonstrate that a 20 mg/kg dose of DCUK-OEt produced a transient, but significant, reduction in relapse drinking, similar to a larger dose of acamprosate (50 mg/kg). A 75 mg/kg dose of DCUK-OEt produced an almost complete abolition of alcohol intake even though the animals had alcohol available in a free-choice situation. This reduction in drinking was evident even several days after the administration of DCUK-OEt was stopped. The reduction of ethanol consumption was compensated by an increased consumption of water by these animals, greatly reducing the preference ratio (data not shown). By comparison to acamprosate, the effects of DCUK-OEt were greater in magnitude and were longer lasting even though the dose of DCUK-OEt was more than two fold lower overall. This indicates that DCUK-OEt would be an effective medication in preventing/reducing relapse drinking in addicted individuals.

Example 11. Effect of DCUK-OEt on Operant Responding for Alcohol by Alcohol Dependent Rats This example illustrates that ethanol dependent rats are motivated to work for ethanol reward during a period of forced abstinence and that DCUK-OEt reduces responding for the alcohol reward.

The methods used in this study are extensively described in (Vendruscolo et al., 2012). The rats were first trained to self-administer ethanol in an operant chamber. The rats were given free-choice access to alcohol (10% w/v) and water for 1 day in their home cages to habituate them to the taste of alcohol. The rats were then subjected to an overnight session in the operant chambers with access to one lever that delivered water (FR1). Food was available ad libitum during this training. After 1 day off, the rats were subjected to a 2 hour session (FR1) for 1 day and a 1 hour session (FR1) the next day, with one lever delivering alcohol. All of the subsequent sessions lasted 30 minutes, and two levers were available (left lever: water; right lever: alcohol). Once trained, the rats were made dependent by chronic, intermittent exposure to alcohol vapors (Gilpin et al., 2008). They underwent cycles of 14 hours of ethanol exposure (blood alcohol levels during vapor exposure ranged between 150 and 250 mg %) and 10 hours in the absence of ethanol vapor, during which behavioral testing for acute withdrawal occurred (i.e., 6-8 hours after vapor was turned off, when brain and blood alcohol levels were negligible). Nondependent rats were those not exposed to alcohol vapor. Pharmacological testing occurred after at least 2 months of vapor exposure, when full dependence was observed. DCUKA-OEt was administered i.p. at the doses specified in FIG. 18, sixty minutes prior to placing the animal in the operant chamber. The vehicle for DCUK-OEt was injected in certain animals as a control.

Figure 18:
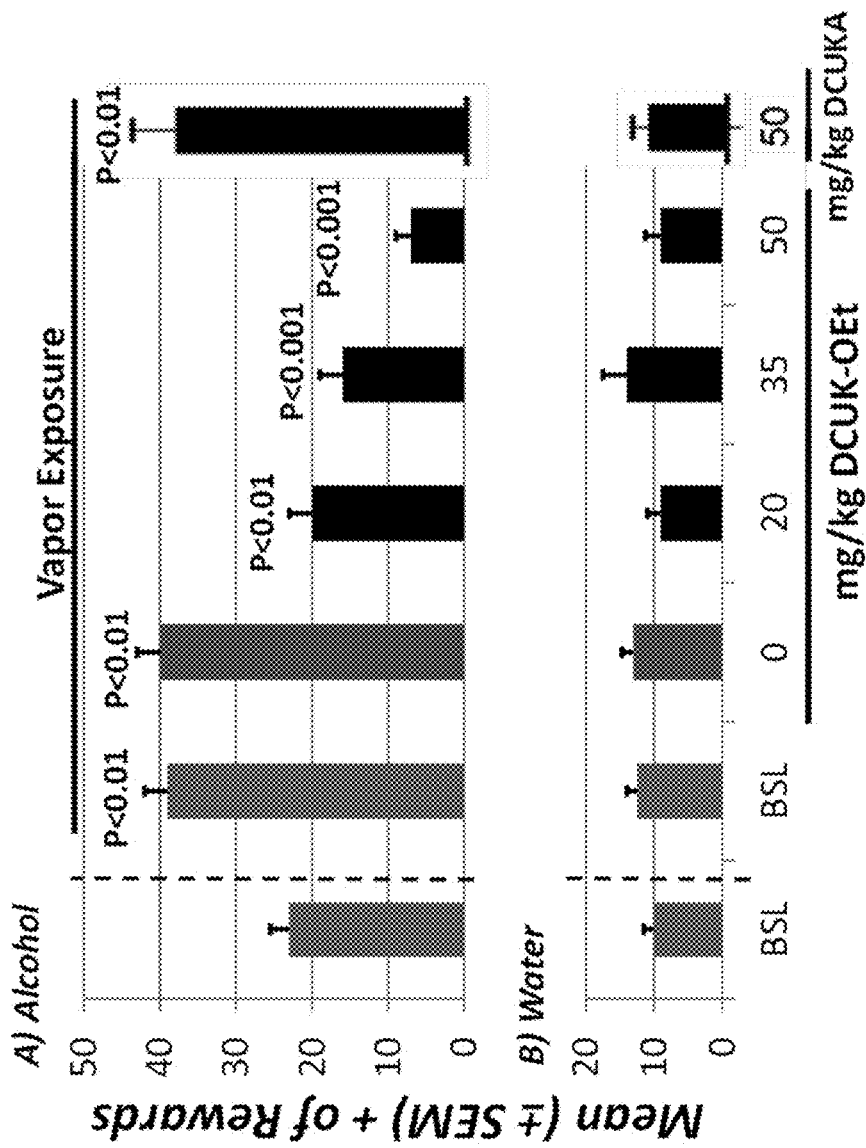
FIG. 18 illustrates the effects of DCUK-OEt and DCUKA in an operant responding paradigm on alcohol self-administration in ethanol dependent rats, demonstrating that DCUKA has no significant effect compared to baseline (BSL) in ethanol vapor-exposed alcohol dependent rats, while DCUK-OEt at 20 mg/kg brought responding level of the ethanol vapor-exposed rats down to the same level of self-administration non-ethanol pretreated control rats. No effect of DCUK-OEt was observed lever pressing for water by the alcohol dependent rats.

FIG. 18 illustrates the effects of DCUK-OEt and DCUKA on alcohol self-administration in ethanol dependent rats exposed to either ethanol (alcohol) vapor or water vapor. The data in FIG. 18 demonstrate that DCUKA has no significant effect on repressing alcohol self-administration compared to baseline (BSL) in ethanol vapor-exposed rats, while DCUK-OEt at 20 mg/kg brought the ethanol vapor exposed rats down to the same level of self-administration as non-ethanol pretreated control rats. Higher doses of DCUK-OEt (35 and 50 mg/kg) reduced lever pressing for ethanol to even lower levels in the alcohol-dependent rats. None of the doses of DCUK-OEt tested had any effect on water intake.

References Each document listed below is incorporated herein by reference in its entirety. Belkouch M, Dansereau M A, Tetreault P, Biet M, Beaudet N, Dumaine R, Chraibi A, Melik-Parsadaniantz S, Sarret P (2014) Functional up-regulation of $Na_v1.8$ sodium channel in Abeta afferent fibers subjected to chronic peripheral inflammation. Journal of neuroinflammation 11:45. Bie B, Zhu W, Pan ZZ (2009a) Rewarding morphine-induced synaptic function of delta-opioid receptors on central glutamate synapses. The Journal of pharmacology and experimental therapeutics 329 (1): 290-6. Borghese C M, Hicks J A, Lapid D J, Trudell J R, Harris R A (2014) GABA(A) receptor transmembrane amino acids are critical for alcohol action: disulfide cross-linking and alkyl methanethiosulfonate labeling reveal relative location of binding sites. Journal of neurochemistry 128 (3):363-75. Cahill C M, Morinville A, Hoffert C, O'Donnell D, Beaudet A (2003) Up-regulation and trafficking of delta opioid receptor in a model of chronic inflammation: implications for pain control. Pain 101 (1-2): 199-208. Chattopadhyay M, Mata M, Fink D J (2008) Continuous delta-opioid receptor activation reduces neuronal voltage-gated sodium channel (NaV1.7) levels through activation of protein kinase C in painful diabetic neuropathy. The Journal of neuroscience: the official journal of the Society for Neuroscience 28 (26):6652-8. Chattopadhyay M, Mata M, Fink D J (2011) Vector-mediated release of GABA attenuates pain-related behaviors and reduces Na(V)1.7 in DRG neurons. European journal of pain 15 (9):913-20. Chen C, Okayama H (1987) High-efficiency transformation of mammalian cells by plasmid DNA. Molecular and cellular biology 7 (8):2745-52. Cheng Y, Prusoff W H (1973) Relationship between the inhibition constant (K1) and the concentration of inhibitor which causes 50 percent inhibition (150) of an enzymatic reaction. Biochemical pharmacology 22 (23): 3099-108. Cichewicz D L (2004) Synergistic interactions between cannabinoid and opioid analgesics. Life sciences 74 (11):1317-24. Clapp P, Bhave S V, Hoffman P L (2008) How Adaptation of the Brain to Alcohol Leads to Dependence: A Pharmacological Perspective. Alcohol research & health: the journal of the National Institute on Alcohol Abuse and Alcoholism 31 (4):310-339. Csermely P, Agoston V, Pongor S (2005) The efficiency of multi-target drugs: the network approach might help drug design. Trends in pharmacological sciences 26 (4): 178-82. Egli M, Koob G F, Edwards S (2012) Alcohol dependence as a chronic pain disorder. Neuroscience and biobehavioral reviews 36 (10):2179-92. Enoch M A, Baghal B, Yuan Q, Goldman D (2013) A factor analysis of global GABAergic gene expression in human brain identifies specificity in response to chronic alcohol and cocaine exposure. PloS one 8 (5):e64014. Femenia T, Garcia-Gutierrez M S, Manzanares J (2010) CB1 receptor blockade decreases ethanol intake and associated neurochemical changes in fawn-hooded rats. Alcoholism, clinical and experimental research 34 (1): 131-41. Gaveriaux-Ruff C, Nozaki C, Nadal X, Hever X C, Weibel R, Matifas A, Reiss D, Filliol D, Nassar M A, Wood I N, Maldonado R, Kieffer B L (2011) Genetic ablation of delta opioid receptors in nociceptive sensory neurons increases chronic pain and abolishes opioid analgesia. Pain 152 (6):1238-48. Gilpin N W, Richardson H N, Lumeng L, Koob G F (2008) Dependence-induced alcohol drinking by alcohol-preferring (P) rats and outbred Wistar rats. Alcoholism, clinical and experimental research 32 (9): 1688-96. Grant B F, Hasin D S, Stinson F S, Dawson D A, Chou S P, Ruan W J, Pickering R P (2004) Prevalence, correlates, and disability of personality disorders in the United States: results from the national epidemiologic survey on alcohol and related conditions. The Journal of clinical psychiatry 65 (7):948-58. Grzyb J A, Shen M, Yoshina-Ishii C, Chi W, Brown R S, Batey R A (2005) Carbamoylimidazolium and thiocarbamoylimidazolium salts: novel reagents for the synthesis of ureas, thioureas, carbamates, thiocarbamates and amides. Tetrahedron 61 (30):7153-7175. Guo J L, Lee V M (2014) Cell-to-cell transmission of pathogenic proteins in neurodegenerative diseases. Nature medicine 20 (2): 130-8. Harvey R J, Yee B K (2013) Glycine transporters as novel therapeutic targets in schizophrenia, alcohol dependence and pain. Nature reviews. Drug discovery 12 (11):866-85. Howlett A C, Barth F, Bonner T I, Cabral G, Casellas P, Devane W A, Felder C C, Herkenham M, Mackie K, Martin B R, Mechoulam R, Pertwee R G (2002) International Union of Pharmacology. XXVII. Classification of cannabinoid receptors. Pharmacological reviews 54 (2): 161-202. Institute of Medicine (2011)

Relieving pain in America, ed'eds). Joseph E K, Levine J D (2009) Comparison of oxaliplatin- and cisplatin-induced painful peripheral neuropathy in the rat. The journal of pain: official journal of the American Pain Society 10 (5):534-41. Kang-Park M H, Kieffer B L, Roberts A J, Siggins G R, Moore S D (2007) Presynaptic delta opioid receptors regulate ethanol actions in central amygdala. The Journal of pharmacology and experimental therapeutics 320 (2):917-25. Kehlet H, Jensen T S, Woolf C J (2006) Persistent postsurgical pain: risk factors and prevention. Lancet 367 (9522): 1618-25. Kou J, Yoshimura M (2007) Isoform-specific enhancement of adenylyl cyclase activity by n-alkanols. Alcoholism, clinical and experimental research 31 (9): 1467-72. Kumar S, Fleming R L, Morrow A L (2004) Ethanol regulation of gamma-aminobutyric acid A receptors: genomic and nongenomic mechanisms. Pharmacology & therapeutics 101 (3):211-26. Lu J J, Pan W, Hu Y J, Wang Y T (2012) Multi-target drugs: the trend of drug research and development. PloS one 7 (6):e40262. Manzanares J, Corchero J, Romero J, Fernandez-Ruiz J J, Ramos J A, Fuentes J A (1999) Pharmacological and biochemical interactions between opioids and cannabinoids. Trends in pharmacological sciences 20 (7):287-94. Margolis E B, Mitchell J M, Hjelmstad G O, Fields H L (2011) A novel opioid receptor-mediated enhancement of GABAA receptor function induced by stress in ventral tegmental area neurons. The Journal of physiology 589(Pt 17):4229-42. Mason BJ, Quello S, Goodell V, Shadan F, Kyle M, Begovic A (2014) Gabapentin treatment for alcohol dependence: a randomized clinical trial. JAMA internal medicine 174 (1):70-7. Moore R A, Wiffen P J, Derry S, Toelle T, Rice A S (2014) Gabapentin for chronic neuropathic pain and fibromyalgia in adults. The Cochrane database of systematic reviews 4:CD007938. Normandin A, Luccarini P, Molat J L, Gendron L, Dallel R (2013) Spinal mu and delta opioids inhibit both thermal and mechanical pain in rats. The Journal of neuroscience: the official journal of the Society for Neuroscience 33 (28): 11703-14. Olive MF (2010) Pharmacotherapies for alcoholism: the old and the new. CNS & neurological disorders drug targets 9 (1):2-4. Pang M H, Kim Y, Jung K W, Cho S, Lee D H (2012) A series of case studies: practical methodology for identifying antinociceptive multi-target drugs. Drug discovery today 17 (9-10):425-34. Perl E R (2011) Pain mechanisms: a commentary on concepts and issues. Progress in neurobiology 94 (1):20-38. Pernia-Andrade A J, Kato A, Witschi R, Nyilas R, Katona I, Freund T F, Watanabe M, Filitz J, Koppert W, Schuttler J, Ji G, Neugebauer V, Marsicano G, Lutz B, Vanegas H, Zeilhofer H U (2009) Spinal endocannabinoids and CB1 receptors mediate C-fiber-induced heterosynaptic pain sensitization. Science 325 (5941):760-4. Rios C, Gomes I, Devi L A (2006) mu opioid and CB1 cannabinoid receptor interactions: reciprocal inhibition of receptor signaling and neuritogenesis. British journal of pharmacology 148 (4):387-95. Salomon Y, Londos C, Rodbell M (1974) A highly sensitive adenylate cyclase assay. Analytical biochemistry 58 (2):541-8. Sams-Dodd F (2005) Target-based drug discovery: is something wrong? Drug discovery today 10 (2): 139-47. Snell L D, Claffey D J, Ruth J A, Valenzuela C F, Cardoso R, Wang Z, Levinson S R, Sather W A, Williamson A V, Ingersoll N C, Ovchinnikova L, Bhave S V, Hoffman P L, Tabakoff B (2000) Novel structure having antagonist actions at both the glycine site of the N-methyl-D-aspartate receptor and neuronal voltage-sensitive sodium channels: biochemical, electrophysiological, and behavioral characterization. The Journal of pharmacology and experimental therapeutics 292 (1):215-27. Spanagel R, Holter SM (1999) Long-term alcohol self-administration with repeated alcohol deprivation phases: an animal model of alcoholism? Alcohol and alcoholism 34 (2):231-43. Strickland I T, Martindale J C, Woodhams P L, Reeve A J, Chessell I P, McQueen DS (2008) Changes in the expression of NaV1.7, NaV1.8 and NaV1.9 in a distinct population of dorsal root ganglia innervating the rat knee joint in a model of chronic inflammatory joint pain. European journal of pain 12 (5):564-72. Tabakoff B, Hoffman P L (2013) The neurobiology of alcohol consumption and alcoholism: an integrative history. Pharmacology, biochemistry, and behavior 113:20-37. Taylor B K (2009) Spinal inhibitory neurotransmission in neuropathic pain. Current pain and headache reports 13 (3):208-14. Van de Ven T J, John Hsia H L (2012) Causes and prevention of chronic postsurgical pain. Current opinion in critical care 18 (4):366-71. van Rijn R M, Brissett D I, Whistler J L (2010) Dual efficacy of delta opioid receptor-selective ligands for ethanol drinking and anxiety. The Journal of pharmacology and experimental therapeutics 335 (1):133-9. van Rijn R M, Brissett D I, Whistler J L (2012) Emergence of functional spinal delta opioid receptors after chronic ethanol exposure. Biological psychiatry 71 (3):232-8. van Rijn R M, Defriel J N, Whistler J L (2013) Pharmacological traits of delta opioid receptors: pitfalls or opportunities? Psychopharmacology 228 (1): 1-18. Vendruscolo L F, Barbier E, Schlosburg J E, Misra K K, Whitfield T W, Jr., Logrip M L, Rivier C, Repunte-Canonigo V, Zorrilla E P, Sanna PP, Heilig M, Koob G F (2012) Corticosteroid-dependent plasticity mediates compulsive alcohol drinking in rats. The Journal of neuroscience: the official journal of the Society for Neuroscience 32 (22):7563-71. Vigano D, Rubino T, Parolaro D (2005) Molecular and cellular basis of cannabinoid and opioid interactions. Pharmacology, biochemistry, and behavior 81 (2):360-8. Zeilhofer H U, Wildner H, Yevenes G E (2012) Fast synaptic inhibition in spinal sensory processing and pain control. Physiological reviews 92 (1): 193-235. Zhang X, Bao L, Guan JS (2006) Role of delivery and trafficking of delta-opioid peptide receptors in opioid analgesia and tolerance. Trends in pharmacological sciences 27 (6):324-9.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of Formula (VI) or a pharmacologically acceptable salt thereof:

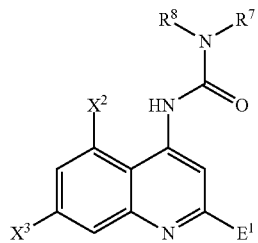

wherein:
R$^7$ is alkyl, cycloalkyl, aminoalkyl, or phenyl; wherein each is optionally substituted one or more times with an alkyl group or an alkyloxy group;
R$^8$ is H, alkyl, cycloalkyl, aminoalkyl, or phenyl; wherein each is optionally substituted one or more times with an alkyl group or an alkyloxy group;
E$^1$ is —C(=O)OR$^9$, —C(=O)R$^9$, —C(=O)N(R$^9$)$_2$, or —(C(R$^9$)$_2$)$_n$—OR$^9$;
n is 1, 2, 3, or 4;
R$^9$ is H, C$_1$-C$_4$ alkyl, or C$_1$-C$_4$ alkyl substituted with one or more moiety selected from the group consisting of C$_1$-C$_4$ alkyl, C$_2$-C$_4$ alkenyl, C$_2$-C$_4$ alkynyl, halo, heteroaryl, Z$^5$R$^{24}$, and N(R$^{25}$)(R$^{26}$);
Z$^5$ is O, S, C(=O)O or O—C(=O);
R$^{24}$, R$^{25}$, and R$^{26}$ are each independently C$_1$-C$_4$ alkyl; and
X$^2$ and X$^3$ are each independently halogen or nitro; provided that when E$^1$ is C(=O)OR$^9$, then at least one of R$^7$ and R$^8$ is not phenyl or alkyl.

2. The compound of claim 1, wherein:
R$^7$ is alkyl, cycloalkyl, aminoalkyl, or phenyl;
R$^8$ is H, alkyl, cycloalkyl, aminoalkyl, or phenyl;
E$^1$ is —C(=O)OR$^9$, —C(=O)R$^9$, —C(=O)N(R$^9$)$_2$, or —(C(R$^9$)$_2$)$_n$—OR$^9$;
n is 1, 2, 3, or 4;
R$^9$ is H, C$_1$-C$_4$ alkyl; and
X$^2$ and X$^3$ are each independently halogen or nitro; provided that when E$^1$ is C(=O)OR$^9$, then at least one of R$^7$ and R$^8$ is not phenyl or alkyl.

3. The compound of claim 1, wherein:
R$^7$ is alkyl, cycloalkyl, aminoalkyl, or phenyl; wherein each is optionally substituted one or more times with an alkyl group or an alkyloxy group;
R$^8$ is H, alkyl, cycloalkyl, aminoalkyl, or phenyl; wherein each is optionally substituted one or more times with an alkyl group or an alkyloxy group;
E$^1$ is —C(=O)OR$^9$ or —C(=O)R$^9$;
R$^9$ is H, C$_1$-C$_4$ alkyl, or C$_1$-C$_4$ alkyl substituted with one or more moiety selected from the group consisting of C$_1$-C$_4$ alkyl, C$_2$-C$_4$ alkenyl, C$_2$-C$_4$ alkynyl, halo, heteroaryl, Z$^5$R$^{24}$, and N(R$^{25}$)(R$^{26}$);
Z$^5$ is O, S, C(=O)O or O—C(=O);
R$^{24}$, R$^{25}$, and R$^{26}$ are each independently C$_1$-C$_4$ alkyl; and
X$^2$ and X$^3$ are each independently halogen or nitro; provided that when E$^1$ is C(=O)OR$^9$, then at least one of R$^7$ and R$^8$ is not phenyl or alkyl.

4. The compound of claim 1, wherein R$^7$ is alkyl, cycloalkyl, aminoalkyl, or phenyl;
R$^8$ is H, alkyl, cycloalkyl, aminoalkyl, or phenyl; E$^1$ is —C(=O)OR$^9$ or —C(=O)R$^9$; R$^9$ is H or C$_1$-C$_4$ alkyl;

X$^2$ and X$^3$ are each independently halogen; provided that when E$^1$ is C(=O)OR$^9$, then at least one of R$^7$ and R$^8$ is not phenyl or alkyl.

5. A method of treating or preventing alcohol addiction relapse in a subject in need thereof, the method comprising administering to the subject a therapeutically effective amount of the compound of claim 1; wherein the subject is abstinent from alcohol.

6. A method of treating pain in a subject in need thereof, the method comprising administering to a subject a therapeutically effective amount of the compound of claim 1 to treat the pain.

7. The method of claim 6, wherein the pain is chronic pain.

8. The method of claim 6, wherein the pain is neuropathic pain.

9. The method of claim 6, wherein the pain is peripheral neuropathic pain.

10. A method of treating pain in a subject in need thereof, the method comprising administering to a subject a therapeutically effective amount of (N, N-dibutyl)-4-ureido-5,7-dichloro-2-carboxy-quinoline or a pharmacologically acceptable salt thereof to treat the pain.

11. The method of claim 10, wherein the pain is chronic pain.

12. The method of claim 10, wherein the pain is neuropathic pain.

13. The method of claim 10, wherein the pain is peripheral neuropathic pain.

14. A method of treating or preventing alcohol addiction relapse in a subject in need thereof, the method comprising administering to the subject a therapeutically effective amount of a compound of Formula (VI) or a pharmacologically acceptable salt thereof; wherein the subject is abstinent from alcohol; and wherein the compound of Formula (VI) is:

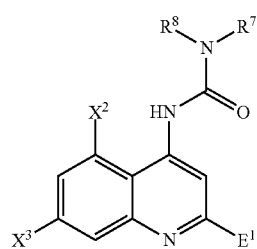

wherein:
R$^7$ is alkyl, cycloalkyl, aminoalkyl, or phenyl; wherein each is optionally substituted one or more times with an alkyl group or an alkyloxy group;
R$^8$ is H, alkyl, cycloalkyl, aminoalkyl, or phenyl; wherein each is optionally substituted one or more times with an alkyl group or an alkyloxy group;
E$^1$ is —C(=O)OR$^9$, —C(=O)R$^9$, —C(=O)N(R$^9$)$_2$, or —(C(R$^9$)$_2$)$_n$—OR$^9$;
n is 1, 2, 3, or 4;
R$^9$ is H, C$_1$-C$_4$ alkyl, or C$_1$-C$_4$ alkyl substituted with one or more moiety selected from the group consisting of C$_1$-C$_4$ alkyl, C$_2$-C$_4$ alkenyl, C$_2$-C$_4$ alkynyl, halo, heteroaryl, Z$^5$R$^{24}$, and N(R$^{25}$)(R$^{26}$);
Z$^5$ is O, S, C(=O)O or O—C(=O);
R$^{24}$, R$^{25}$, and R$^{26}$ are each independently C$_1$-C$_4$ alkyl; and
X$^2$ and X$^3$ are each independently halogen or nitro.

15. The method of claim 14, wherein:
$R^7$ is alkyl, cycloalkyl, aminoalkyl, or phenyl; wherein each is optionally substituted one or more times with an alkyl group or an alkyloxy group;
$R^8$ is H, alkyl, cycloalkyl, aminoalkyl, or phenyl; wherein each is optionally substituted one or more times with an alkyl group or an alkyloxy group;
$E^1$ is —C(=O)OR$^9$ or —C(=O)R$^9$;
n is 1, 2, 3, or 4;
$R^9$ is H, $C_1$-$C_4$ alkyl, or $C_1$-$C_4$ alkyl substituted with one or more moiety selected from the group consisting of $C_1$-$C_4$ alkyl, $C_2$-$C_4$ alkenyl, $C_2$-$C_4$ alkynyl, halo, heteroaryl, $Z^5R^{24}$, and $N(R^{25})(R^{26})$;
$Z^5$ is O, S, C(=O)O or O—C(=O);
$R^{24}$, $R^{25}$, and $R^{26}$ are each independently $C_1$-$C_4$ alkyl; and
$X^2$ and $X^3$ are each independently halogen or nitro.

16. The method of claim 14, wherein:
$R^7$ is alkyl, cycloalkyl, aminoalkyl, or phenyl;
$R^8$ is H, alkyl, cycloalkyl, aminoalkyl, or phenyl;
$E^1$ is —C(=O)OR$^9$ or —C(=O)R$^9$;
n is 1, 2, 3, or 4;
$R^9$ is H, $C_1$-$C_4$ alkyl; and
$X^2$ and $X^3$ are each independently halogen or nitro;
provided that when $E^1$ is C(=O)OR$^9$, then at least one of $R^7$ and $R^8$ is not phenyl or alkyl.

17. The method of claim 14, wherein $R^7$ is alkyl, cycloalkyl, aminoalkyl, or phenyl; $R^8$ is H, alkyl, cycloalkyl, aminoalkyl, or phenyl; $E^1$ is —C(=O)OR$^9$ or —C(=O)R$^9$; $R^9$ is H or $C_1$-$C_4$ alkyl; and $X^2$ and $X^3$ are each independently halogen.

18. The method of claim 14, wherein $R^7$ is phenyl; $R^8$ is phenyl; $E^1$ is —C(=O)OR$^9$ or —C(=O)R$^9$; $R^9$ is H or $C_1$-$C_4$ alkyl; and $X^2$ and $X^3$ are each independently halogen.

19. The method of claim 14, wherein: $R^7$ is alkyl; $R^8$ is alkyl; $E^1$ is —C(=O)OR$^9$; $R^9$ is H or $C_1$-$C_4$ alkyl; and $X^2$ and $X^3$ are each independently halogen.

20. A method of treating or preventing alcohol addiction relapse in a subject in need thereof, the method comprising administering to the subject a therapeutically effective amount of a positive allosteric modulator of a GABA-A receptor which comprises $\alpha_1\beta_2\gamma_2$ subunits, $\alpha_1\beta_3\gamma_2$ subunits, $\alpha_1\beta_3\delta$ subunits, or $\alpha_1\beta_3\delta$ subunits; and wherein the modulator acts at the interface of the alpha and beta subunits of the GABA-A receptor.

21. The method of claim 6, further comprising administering a therapeutically effective amount of an opioid agonist, a non-steroidal anti-inflammatory drug, a corticosteroid, a serotonin reuptake inhibitor, a calcium channel blocker, an anticonvulsant, or a combination of two or more thereof.

22. The method of claim 6, further comprising administering a therapeutically effective amount of morphine, oxycodone, aspirin, ibuprofen, naproxen, duloxetine, fluoxetine, gabapentin, clonidine, or pregabalin.

23. The method of claim 10, further comprising administering a therapeutically effective amount of an opioid agonist, a non-steroidal anti-inflammatory drug, a corticosteroid, a serotonin reuptake inhibitor, a calcium channel blocker, an anticonvulsant, or a combination of two or more thereof.

24. The method of claim 10, further comprising administering a therapeutically effective amount of morphine, oxycodone, aspirin, ibuprofen, naproxen, duloxetine, fluoxetine, gabapentin, clonidine, or pregabalin.

* * * * *